US007367933B2

(12) United States Patent
Eldridge et al.

(10) Patent No.: US 7,367,933 B2
(45) Date of Patent: May 6, 2008

(54) SCREENING OF CHEMICAL COMPOUNDS PURIFIED FROM BIOLOGICAL SOURCES

(75) Inventors: Gary Eldridge, San Diego, CA (US); Lu Zeng, San Diego, CA (US); Peader Cremin, San Diego, CA (US); Chris Lee, Yorba Linda, CA (US); Helene C. Vervoort, Chelmsford, MA (US); Marilyn Ghanem, St. Louis, MO (US)

(73) Assignee: Sequoia Sciences, Inc., St. Louis, MO (US)

( * ) Notice: Subject to any disclaimer, the term of this patent is extended or adjusted under 35 U.S.C. 154(b) by 111 days.

(21) Appl. No.: 11/358,815

(22) Filed: Feb. 21, 2006

(65) Prior Publication Data

US 2006/0223118 A1 Oct. 5, 2006

Related U.S. Application Data

(60) Division of application No. 10/115,741, filed on Apr. 3, 2002, which is a continuation-in-part of application No. PCT/US00/30195, filed on Nov. 2, 2000.

(60) Provisional application No. 60/280,739, filed on Apr. 3, 2001, provisional application No. 60/328,788, filed on Oct. 15, 2001, provisional application No. 60/189,872, filed on Mar. 16, 2000, provisional application No. 60/209,636, filed on Jun. 6, 2000, provisional application No. 60/163,070, filed on Nov. 2, 1999.

(51) Int. Cl.
*C40B 50/00* (2006.01)
*G01N 33/53* (2006.01)

(52) U.S. Cl. .......................................... 506/23; 435/7.1
(58) Field of Classification Search ................. 506/23; 435/7.1
See application file for complete search history.

(56) References Cited

U.S. PATENT DOCUMENTS

| 5,886,155 A | 3/1999 | Armah et al. |
| 5,908,960 A | 6/1999 | Newlander |
| 5,955,269 A | 9/1999 | Ghai et al. |
| 5,962,736 A | 10/1999 | Zambias et al. |
| 6,066,848 A | 5/2000 | Kassel et al. |
| 6,129,924 A | 10/2000 | Maurel et al. |
| 6,524,863 B1 | 2/2003 | Abedi |

FOREIGN PATENT DOCUMENTS

| WO | WO 99/20291 A | 4/1999 |
| WO | PCT/US00/30195 | 5/2001 |
| WO | WO 01/33193 | 5/2001 |

OTHER PUBLICATIONS

Borris, Robert P., Natural Products Research: Perspectives From A Major Pharmaceutical Company; Dept. of Natural Products Chemistry, Merck Research Laboratories, Journal of Ethno-Pharmacology, 1996, pp. 29-38, vol. 51.

Cardellina, John H. II, et al., A Chemical Screening Strategy For The Dereplication and Prioritization of HIV-Inhibitory Aqueous Natural Products Extracts; Journal of Natural Products, Jul. 1993, pp. 1123-1129, vol. 56, No. 7.

Claeson et al., Fractionation Protocol for the Isolation of Polypeptides from Plant Biomass, The American Chemical Society and the American Society of Pharmacognosy, Journal of National Products, Jan. 1998, pp. 77-81, vol. 61, No. 1.

Doi, H. and Yanagawa, H.; *Combinatorial Chemistry & High Throughput Screening*, Genotype-Phenotype Linkage for Directed Evolution and Screening of Combinatorial Protein Libraries; Jul. 1993, vol. 56, No. 7, pp. 1123-1129 (Abstract).

Ghose et al., J. Comb. Chem., pp. 55-68, 1999.

Haberlein, Hanns et al., Chelidonium Majus L.: Components With In Vitro Affinity for the GABAa Receptor. Positive Cooperation of Alkaloids, Planta Medica, 1996, pp. 227-231, vol. 2, Georg Thieme Verlag Stuttgart, New York.

Ingkaninan, K., et al., Interference of Linoleic Acid Fraction in Some Receptor Binding Assays, American Chemical Society and American Society of Pharmacognosy, Div. of Pharmacognosy and Div. of Medicinal Chemistry, Journal of Natural Products, 1999, pp. 912-914, vol. 62.

Kang, Jing X., et al., Biochem Journal, 1994, pp. 795-802, vol. 303.

Kato, Junzo, Arachidonic Acid As A Possible Modulator of Estrogen, Progestin, Androgen, and Glucocorticoid Receptors In the Central and Peripheral Tissues; Dept. of Obstetrics and Gynecology, Yamanashi Medical University; J. Steroid Biochem, 1989, pp. 219-227, vol. 34, No. 1-6.

Lee, Kit K., et al., Isolation and Structure Elucidation of New PKCa Inhibitors from Pinus flexilus; Journal of Natural Products, 1999, pp. 1407-1409, vol. 61.

(Continued)

*Primary Examiner*—Mark L. Shibuya
(74) *Attorney, Agent, or Firm*—Gallop, Johnson & Neuman, L.C.

(57) ABSTRACT

A method of producing a chemical compound library comprises extracting at least one extract from at least one species of plant; processing at least one of the extract(s) to remove at least one type of chemical interference to produce a processed extract; chromatographically separating the processed extract into a plurality of chromatographic fractions, each containing an amount of chemical compounds; determining the amount of chemical compounds in at least one of the chromatographic fractions; and normalizing the chromatographic fractions in which the amounts were determined to produce normalized chromatographic fractions, each such fraction comprising from about 1 microgram to about 500 micrograms of each of from one to seven chemical compounds that were present in lower concentrations in the extract and that each have a log P of from about −1 to about 5 and a molecular weight less than about 1000 Daltons; thereby to produce a chemical compound library from at least one species of plant.

22 Claims, 20 Drawing Sheets

OTHER PUBLICATIONS

Matter, Hans, et al.; Computation Approaches Towards the Rational Design of Drug-like Compound Libraries, Combinatorial Chemistry & High Throughput Screening, 2001, vol. 4, No. 6 (Abstract).

Menzies, John R. W., et al., Opioid Activity of Alkaloids Extracted From Picralima Nitida (fam. Apocynaceae); European Journal Of Pharmacology, 1998, pp. 101-108, vol. 350.

Patil, Ashok D. et al., Daleformis, a New Phyloalexin from the Roots of Dalea filiciformis: An Inhibitor of Endothelin Converting Enzyme; Journal of Natural Products, 1997, pp. 306-308, vol. 60.

Phillipson, J. David, Radioligand-receptor Binding Assays in the Search for Bioactive Principles from Plants, Pharm. Pharmacol, 1999, vol. 51; pp. 493-503.

Pickett et al., J. Chem Inf. Comput. Sci., 2000, pp. 263-272, vol. 40.

Tan, Ghee T. et al., Evaluation of Natural Products as Inhibitors of Human Immunodeficiency virus Type 1 (HIV-1) Reverse Transcriptase; Journal of Natural Products, Jan.-Feb. 1991, pp. 143-154, vol. 54, No. 1.

Tice, Pest Management Science, Jan. 2001, pp. 3-16, vol. 57.

Turner, David M., Journal of Ethno-Pharmacology, Natural Product Source Material Use In The Pharmaceutical industry: The Glaxo Experience, 1996, pp. 39-44, External Scientific Affairs, Glaxo Research and Development Ltd., vol. 5.

Vallette, Genevieve et al., Modulatory Effects of Unsaturated Fatty Acids on the Binding of Glucocorticoids to Rat Liver Glucocorticoid Receptors, he Endocrine Society, 1991, pp. 1363-1369, vol. 129. No. 3.

Wolfender et al., J. Mass Spectr. Rapid Commun. In Mass Spectr., 1995, S35-S46.

The RoMa placing a 96 column array and vacuum plate over a microtiter collection plate

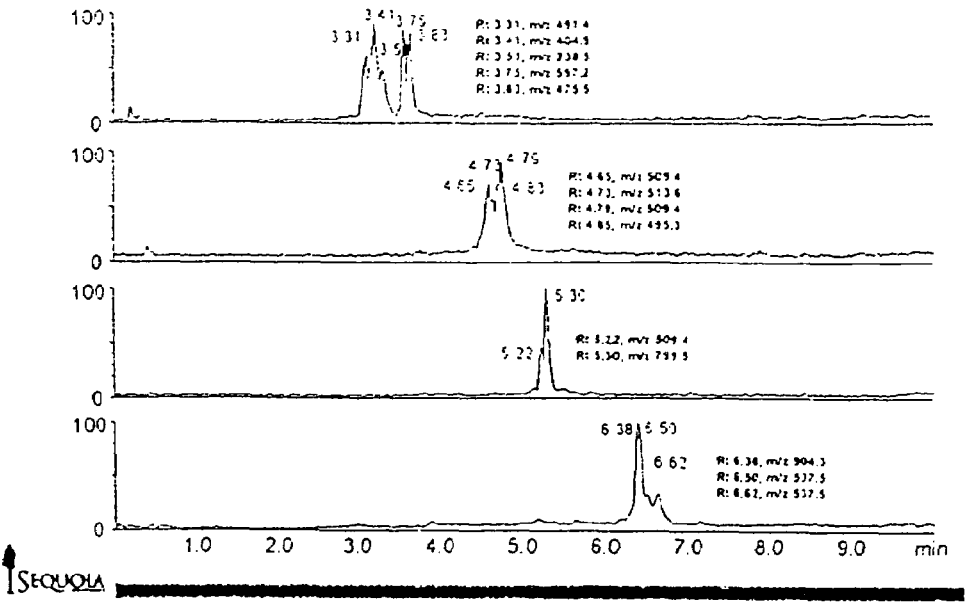
Figure 9
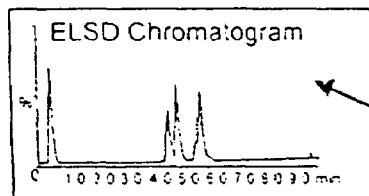
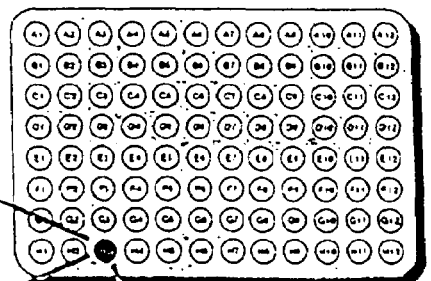
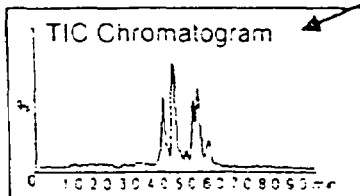
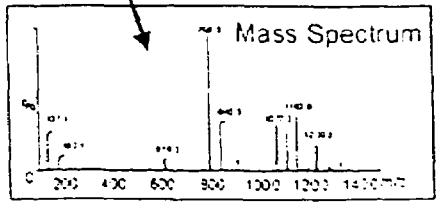

Figure 13

| Well No. | LCMS File Name | Components | Retention time | M+H | Relative pecentage |
|---|---|---|---|---|---|
| G1 | s12-f5-11 | 5 | 4.08 | 523.5 | 22% |
| G1 | s12-f5-11 | 5 | 4.14 | 361.4 | 16% |
| G1 | s12-f5-11 | 5 | 4.18 | 371.5 | 35% |
| G1 | s12-f5-11 | 5 | 4.26 | 371.5 | 15% |
| G1 | s12-f5-11 | 5 | 4.46 | 246.5 | 12% |
| G2 | s12-f5-12 | 4 | 4.28 | 527.4 | 14% |
| G2 | s12-f5-12 | 4 | 4.46 | 309.5 | 43% |
| G2 | s12-f5-12 | 4 | 4.46 | 449.5 | 30% |
| G2 | s12-f5-12 | 4 | 4.48 | 246.6 | 13% |
| G3 | s12-f5-13 | 2 | 4.43 | 399.5 | 36% |
| G3 | s12-f5-13 | 2 | 4.63 | 527.4 | 64% |
| G4 | s12-f5-14 | 5 | 4.63 | 509.4 | 11% |
| G4 | s12-f5-14 | 5 | 4.67 | 511.4 | 26% |
| G4 | s12-f5-14 | 5 | 4.71 | 513.4 | 40% |
| G4 | s12-f5-14 | 5 | 4.75 | 495.4 | 10% |
| G4 | s12-f5-14 | 5 | 4.81 | 509.4 | 13% |
| G5 | s12-f5-15 | 3 | 4.75 | 495.4 | 39% |
| G5 | s12-f5-15 | 3 | 4.75 | 513.7 | 28% |
| G5 | s12-f5-15 | 3 | 4.83 | 799.2 | 20% |
| G5 | s12-f5-16 | 2 | 5.07 | 397.4 | 44% |
| G5 | s12-f5-16 | 2 | 5.61 | 351.5 | 56% |
| G6 | s12-f5-17 | 4 | 5.22 | 509.4 | 14% |
| G6 | s12-f5-17 | 4 | 5.34 | 495.5 | 12% |
| G6 | s12-f5-17 | 4 | 5.34 | 799.2 | 63% |
| G6 | s12-f5-17 | 4 | 5.64 | 695.4 | 11% |

SCREENING OF CHEMICAL COMPOUNDS PURIFIED FROM BIOLOGICAL SOURCES

CROSS REFERENCE TO RELATED APPLICATION

This is a divisional of U.S. Ser. No. 10/115,741, filed Apr. 3, 2002, which claims the benefit of U.S. provisional applications Ser. No. 60/280,739, filed Apr. 3, 2001, and Ser. No. 60/328,788, filed Oct. 15, 2001; and which is also a continuation-in-part of PCT Application No. PCT/US00/30195, filed Nov. 2, 2000, which claims the benefits of U.S. provisional applications Ser. No. 60/163,070, filed Nov. 2, 1999, Ser. No. 60/189,872, filed Mar. 16, 2000, and Ser. No. 60/209,636, filed Jun. 6, 2000.

FIELD OF THE INVENTION

The present invention is directed to screening of chemical compounds purified from plants or other biological materials for testing in biological assays, and more particularly to such screening for high throughput testing of chemical compounds present in biological sources in low concentrations.

BACKGROUND

It is well known in the art of discovering novel chemical compounds with therapeutic effects that plants have yielded some of the most important molecules in history. Civilizations around the globe have exploited the medicinal benefits of plants for millennia. Today, private, public, and government institutions devote extensive resources searching for molecules in plants that may have a potential economic and humanitarian impact. Technological advances in laboratory automation, biochemistry, and molecular biology enable us to currently screen hundreds of thousands of molecules for biological activity every day.

Cragg, et al., in "The search for new pharmaceutical crops: Drug discovery and development at the National Cancer Institute," 161-167, describe the extensive natural library testing program of the National Cancer Institute (NCI) and the methods used to prepare plant extracts for screening. Cardellina II, et al., in J. Nat. Prod., 56(7), 1123-1129 (1993), describe the screening program of the NCI and also specifically discuss the chemical interferences ubiquitous within plants and current techniques used to remove these chemicals before screening or after screening. Turner, in J. Ethnopharm., 51, 39-44 (1996), describes screening plants at a large pharmaceutical company. Borris, in J. Ethnopharm., 51, 29-38 (1996), describes the increased complexities that come with screening plant extracts using a competitive screening program that requires a structured approach and the latest scientific techniques. Shu, in J. Nat. Prod., 61, 1053-1071 (1998), promotes the value of novel chemicals that have been isolated from plants, and lists points a screening laboratory must achieve to improve the success rate when testing plant extracts. The points on the list are not easily accomplished and include challenges such as making a screen suitable for natural libraries, removing all interferences, and accelerating dereplication.

Preparing plant extracts for screening has always been recognized as laborious, and published literature suggests that the method of preparation is more important than previously and currently understood. Plants have numerous ubiquitous compounds that may mask an effect or interfere with the mechanism of action of a biological assay. Ingkaninan, J. Nat. Prod., 62(6), 912-914 (1999), Kato, J. Steroid Biochem., 34(1), 219-227 (1989), Vallete et al., in Endocrin., 129(3), 1363-1369 (1991), and Kang et al, in Biochem J., 303, 795-802 (1994), have reported that fatty acids, phospholipids, and tri-, di-, and monoglycerides cause noncompetitive or mixed noncompetitive inhibition on some receptors or modify the structure or confirmation of receptors in cell-based assays. Numerous plant solvent extracts have high molecular weight compounds that make up greater than 70% of the mass of the extract and that never could be approved drugs. Numerous laboratories do not remove or have not removed these compounds before screening. This may result in false positives or false negatives during subsequent biological assays. Tan, et al., in J. Nat. Prod., 54(1), 143-154 (1991), Cardellina II, et al., in J. Nat. Prod., 56(7), 1123-1129 (1993), Claeson, et al., in J. Nat. Prod., 61(1), 77-81 (1998), Lee, et al., in J. Nat. Prod., 61(11), 1407-1409 (1998), and Patil, et al., in J. Nat. Prod., 60(3), 306-308 (1997), describe false positives that may be attributed to polyphenols and tannins. Some laboratories remove these compounds before screening, while others remove these compounds only after a potential false positive has occurred, believing that these compounds cannot cause a false negative. Phillipson, in J. Pharm. Pharmacol. 51:493-503 (1999), has suggested further that partially purified plant extracts without common metabolites may prove attractive to screening laboratories.

A general mantra in preparing plant extracts states, "it is not what you miss, but what you hit." This approach has led laboratories to put ease of preparation and number of plant extracts prepared and screened ahead of a scientifically based approach for success. Laboratories typically prepare one to three extracts per plant for screening. These extracts may contain one hundred to thousands of chemical compounds per extract.

Because the collision frequency and proper orientation of a ligand and its receptor play a role in binding, screening plant extracts with numerous compounds may interfere with the detection of potential biological effects. In addition, increased dipole-dipole interactions, hydrogen bonding, or steric effects that exist in physiological conditions could also contribute to the disruption of ligand binding. Haberlein, in Planta Medica, 62(3):227-31 (1996), indicate that two different concentrations of the same ethanolic plant extract cause positive and negative allosteric regulation of a GABA receptor. In contrast to accepted principles, interferences may result in false positives as well as false negatives. Menzies, in Eur. J. Pharm., 350(1), 101-108 (1998), suggests that the bioactivity of a known compound in a plant extract is not observed in an opioid assay because of an interfering compound canceling out its activity. Phillipson, in J. Pharm. Pharmacol. 51:493503 (1999), states that the activity of an isolated compound is not always directly comparable to the plant extract from which it was isolated. These suggestions, empirical data, and hypotheses show that many variables exist in the screening process. Because the process of scientific investigation and discovery should reduce the number of variables and operate in a closed system, the removal of all potential interferences from a plant extract before entering a biological screen and further separation of the drug-like chemical compounds to further reduce interference and enable each chemical compound to be tested at its detectable screening concentration are essential.

SUMMARY OF THE INVENTION

In one embodiment, the present invention is directed to a method of producing a chemical compound library comprising extracting at least one extract from at least one species of plant; processing at least one of the extract(s) to remove at least one type of chemical interference to produce a processed extract; chromatographically separating the processed extract into a plurality of chromatographic fractions, each containing an amount of chemical compounds; determining the amount of chemical compounds in at least one of the chromatographic fractions; and normalizing the chromatographic fractions in which the amounts were determined to produce normalized chromatographic fractions, each such fraction comprising from about 1 microgram to about 500 micrograms of each of from one to seven chemical compounds that were present in lower concentrations in the extract and that each have a log P of from about −1 to about 5 and a molecular weight less than about 1000 Daltons; thereby to produce a chemical compound library from at least one species of plant.

In another embodiment, the present invention is directed to a chemical compound library comprising a plurality of chromatographic fractions from at least one biological source. The fractions are substantially free of compounds that interfere with biological assays. The majority of the chromatographic fractions comprising a normalized quantity of from about 1 microgram to about 500 micrograms of seven or fewer chemical compounds. The majority of said chemical compounds having log P of from about −1 to about 5 and a molecular weight less than about 6,000 Daltons.

The present invention is further directed to a subset of such library comprising chemical compounds having similar predetermined molecular ions.

The present invention is further directed to a method of preparing a sublibrary of such library wherein the fractions have associated data comprising at least one of molecular ion data, chromatographic elution data, NMR spectra, MS/MS fragmentation patterns, comprising selecting fractions having at least one set of similar data.

The present invention is also directed to a method of preparing a diverse chemical compound library comprising providing such library wherein each of the chromatographic fractions have associated data comprising at least one of molecular ion data for said chemical compounds, chromatographic elution data for said fractions, NMR spectra for said fractions and MS/MS fragmentation patterns for the chemical compounds selecting fractions having at least one characteristic selected from
   (a) similar molecular ions;
   (b) similar chromatographic elution data;
   (c) similar log Ps; and
   (d) a plurality of biological sources.

The present invention is further directed to a method of identifying biologically active chemical compounds comprising screening such library for biological activity of said chemical compounds.

The present invention is also directed to a chemical compound library comprising: a plurality of arrayed chromatographic fractions derived from one or more biological sources, the majority of the fractions comprising seven or fewer individual nonproteinaceous chemical compounds, and each of the isolates being free of compounds that interfere with biological testing of said individual compounds. In this embodiment of the invention, each of said individual compounds is present in a normalized quantity and has a log P suitable for biological testing of said individual compound, the normalized quantity being sufficient to prepare a sample from said isolate having a concentration of each of the individual compounds suitable for biological testing.

The present invention is also directed to a method for preparing an array of compounds of normalized concentrations from a natural product comprising a mixture of compounds of various concentrations. The method comprises normalizing concentrations of the compounds; and producing an array of samples of the compounds of normalized concentrations. The invention is also directed to that array itself.

The present invention is further directed to a method for screening a natural product comprising a mixture of compounds of various concentrations. The method comprises normalizing concentrations of the compounds; producing an array of samples of the compounds of normalized concentrations; and screening the array.

Further objectives and advantages will become apparent from a consideration of the description, drawings, and examples.

BRIEF DESCRIPTION OF THE DRAWINGS

The invention is better understood by reading the following detailed description with reference to the accompanying figures, in which like reference numerals refer to like elements throughout, and in which:

FIG. 9 is a schematic representation of fractions of chemical compounds in a microtiter plate with mass spectrum and evaporative light scattering chromatogram of an individual fraction within the collection of chemical compounds;

FIG. 13 is a schematic representation of a data table used to compare molecular ions and chromatographic elution conditions of the entire collection of chemical compounds;

DETAILED DESCRIPTION OF THE INVENTION

Figure 1:
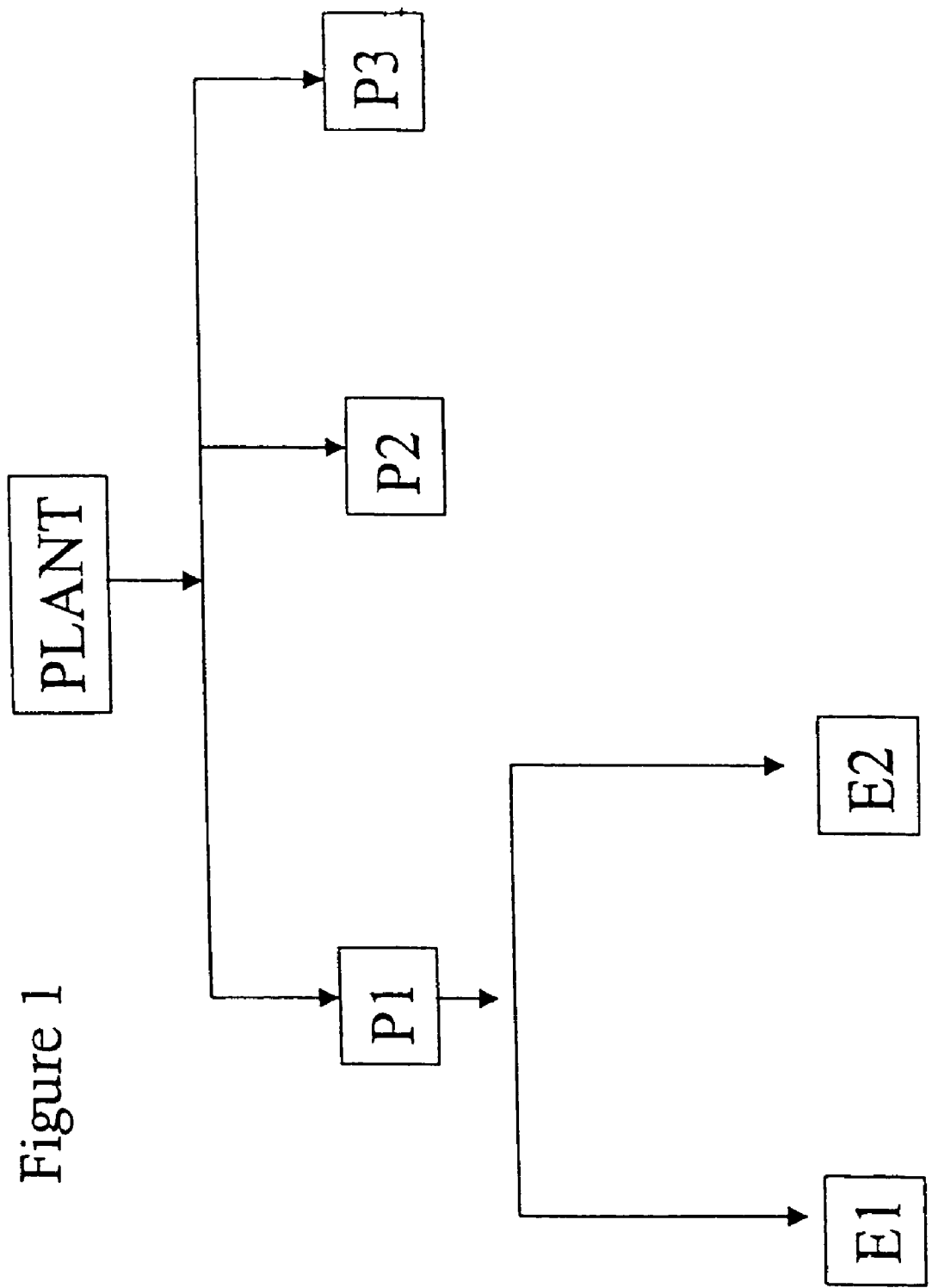
FIG. 1 is a schematic representation of liquid extraction.
Figure 2:
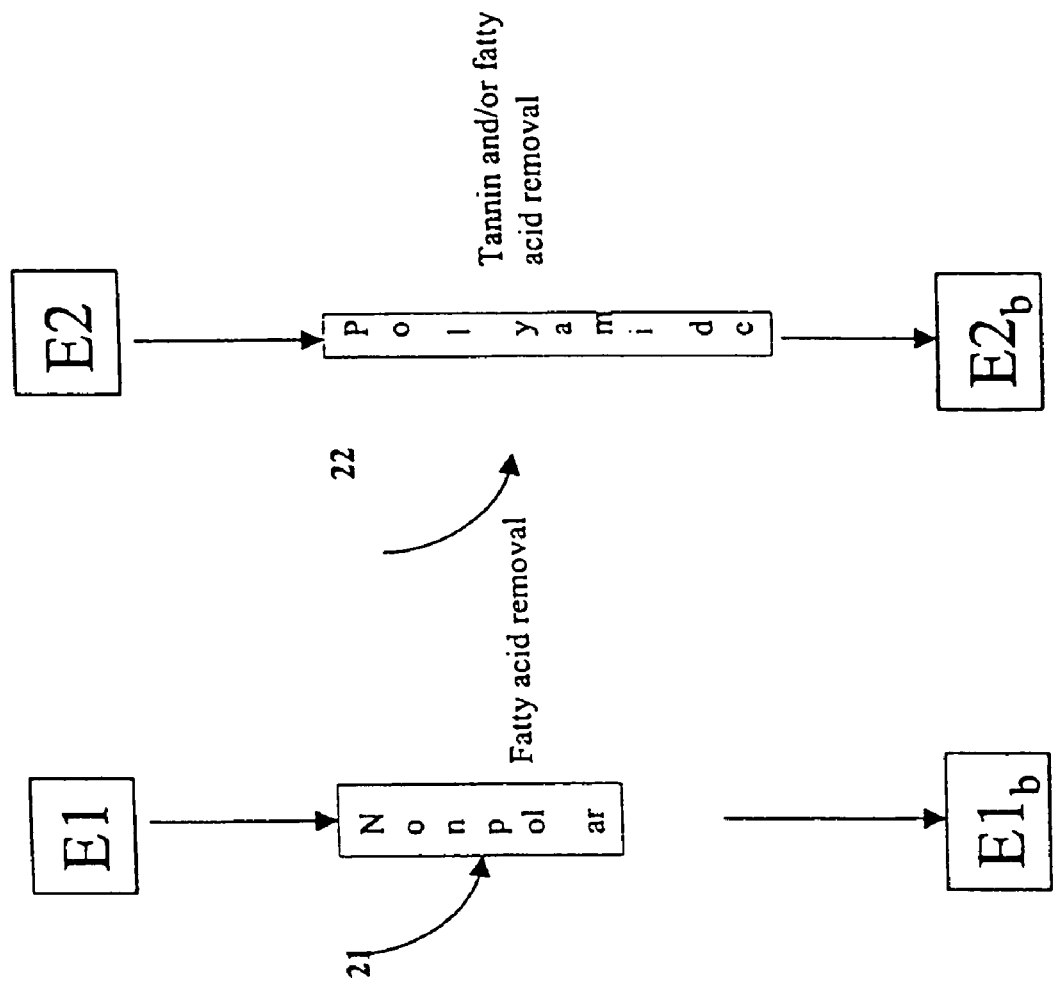
FIG. 2 is a schematic representation of the removal of interferences.
Figure 3:
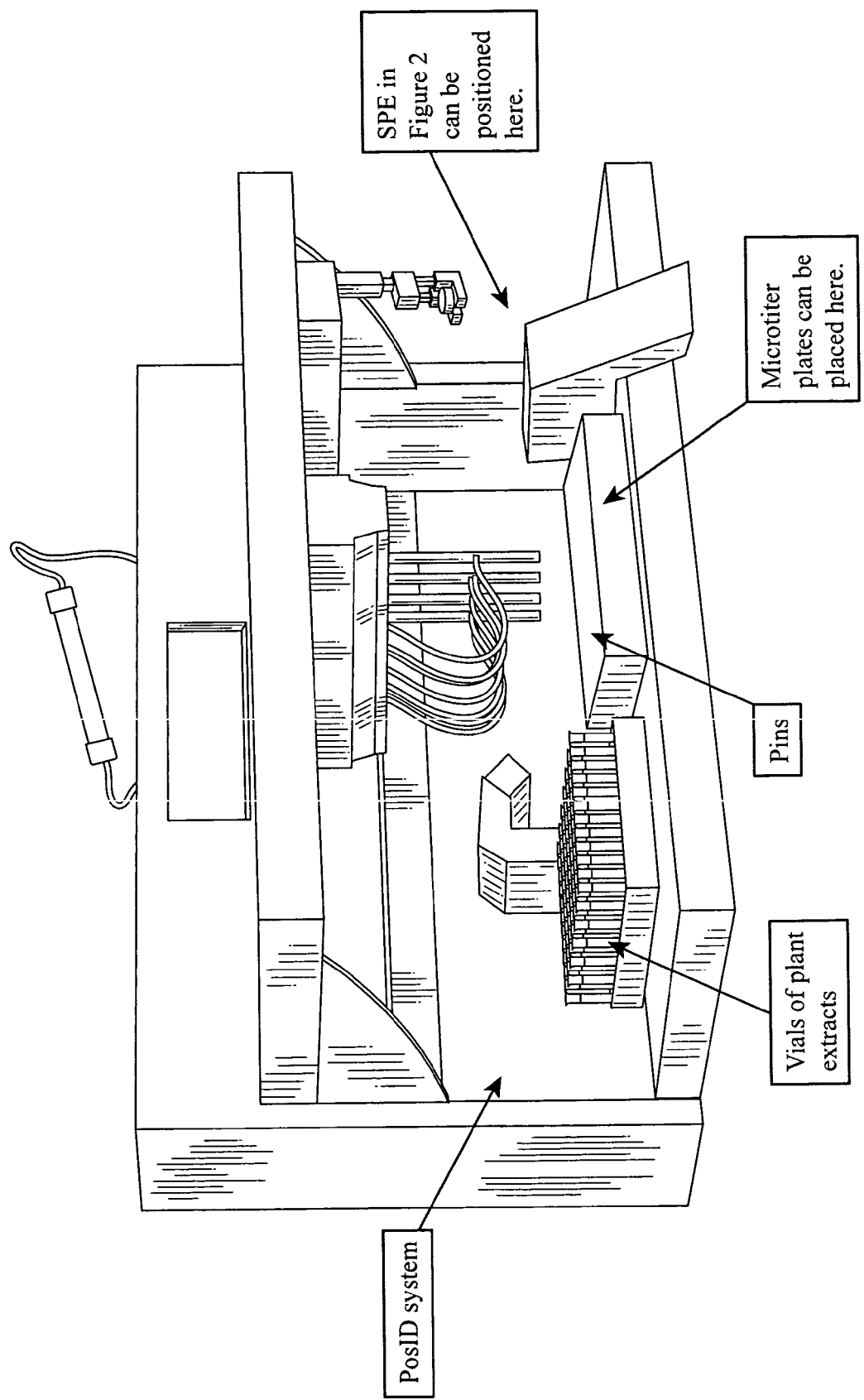
FIG. 3 is a picture of an example of a suitable liquid handling system.
Figure 4:
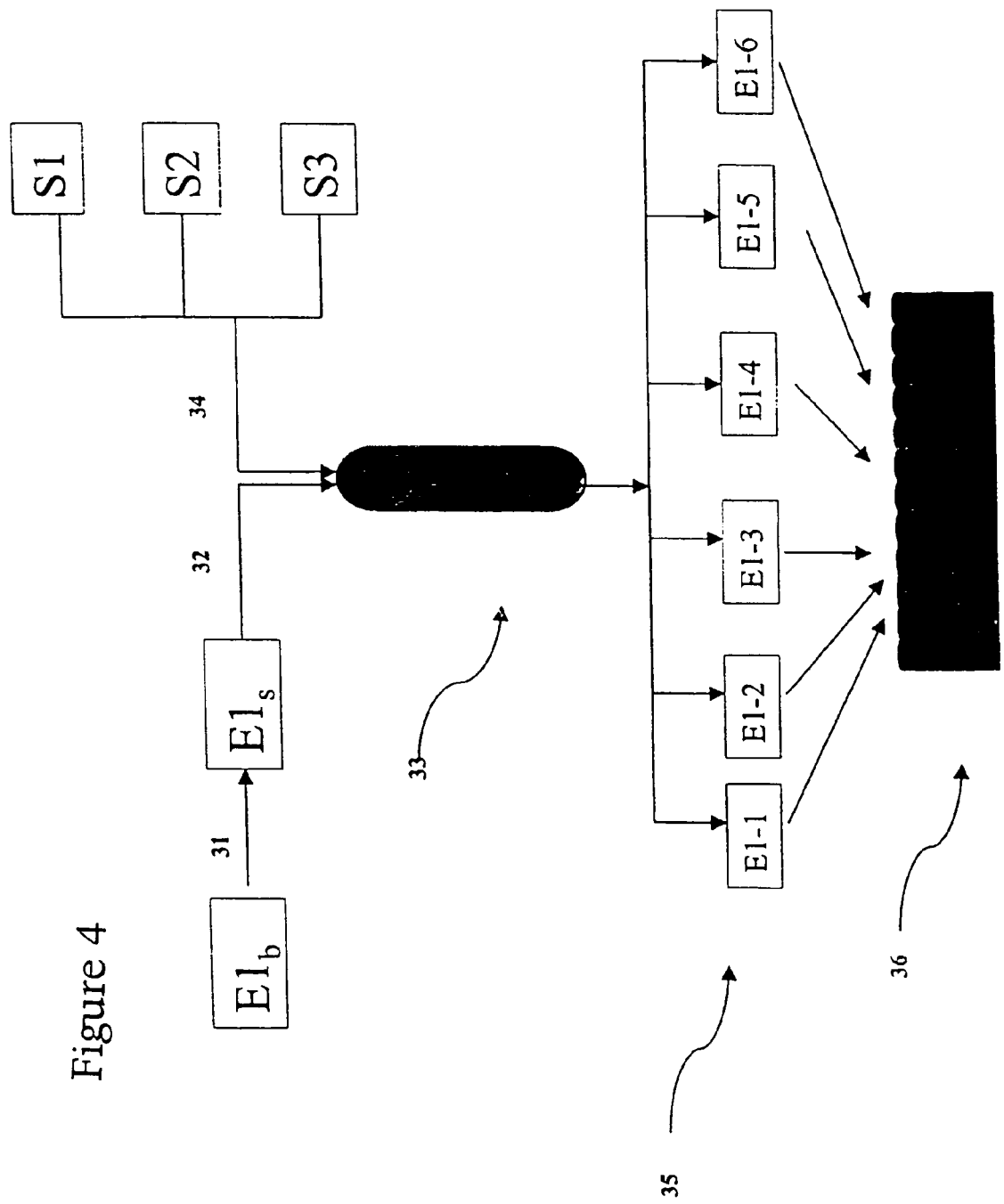
FIG. 4 is a schematic representation of solid phase extraction as a first chromatography step.
Figure 5:
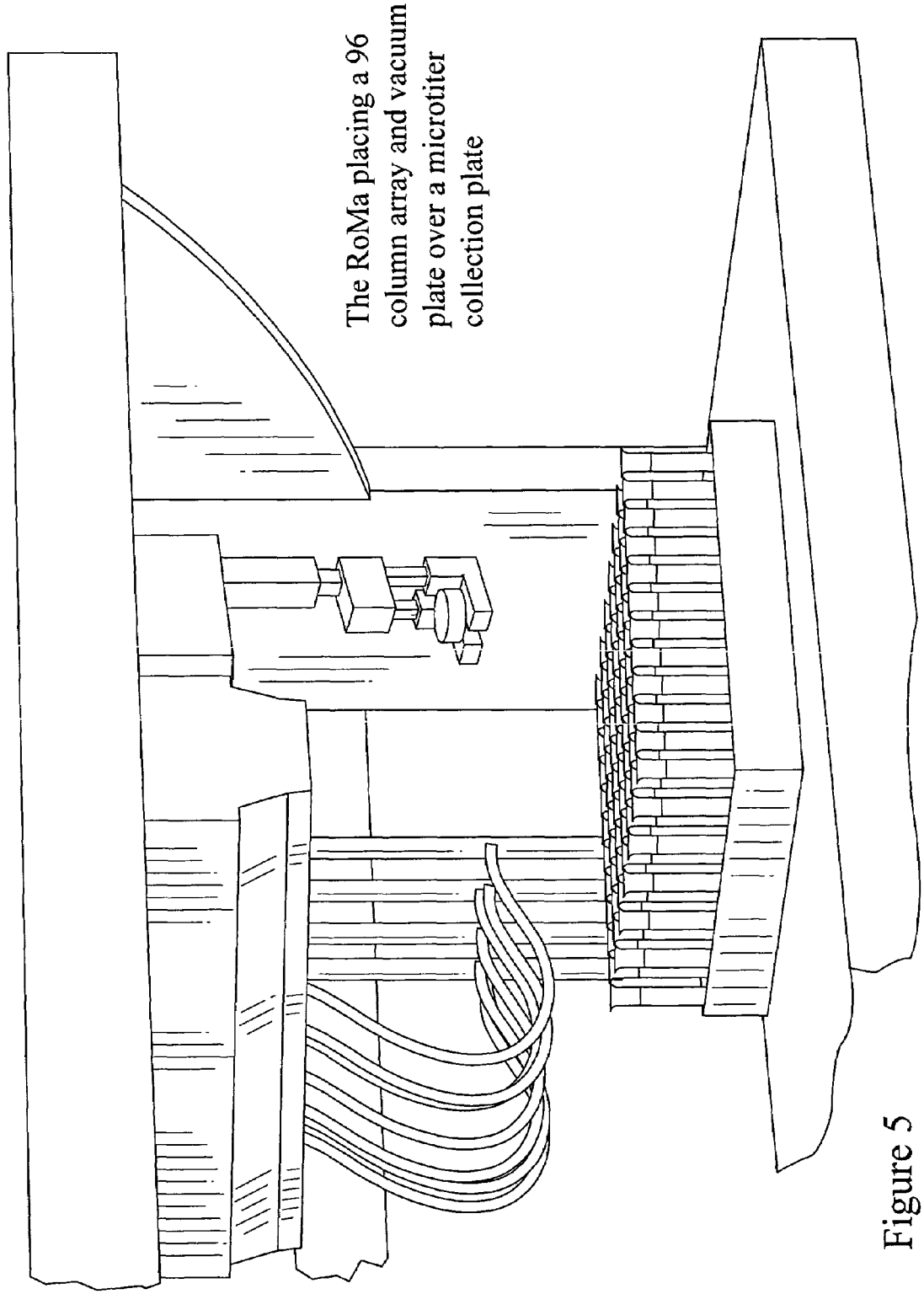
FIG. 5 is a picture of a Robotic Manipulator Arm placing an array of 96 solid phase extraction columns and a vacuum plate over a microtiter plate in a preferred embodiment of the invention.
Figure 6:
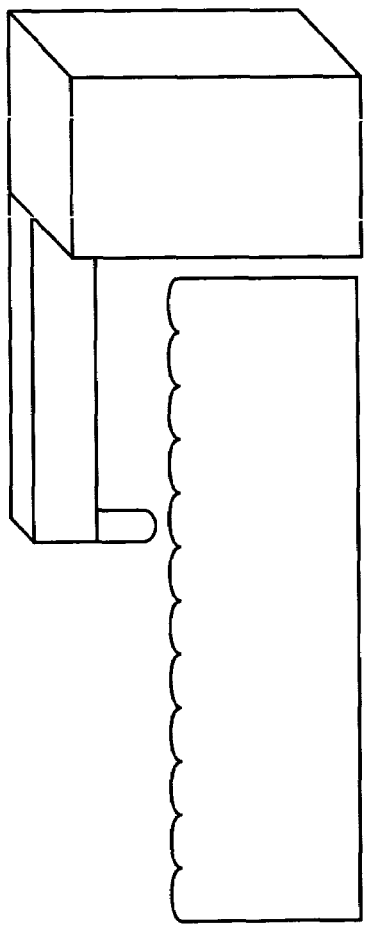
FIG. 6 is a diagram showing the fraction collector system that may comprise part of the solid phase extraction apparatus or the purification apparatus, and explaining the spectroscopic control of fraction collection, including monitoring of multiple wavelengths and setting of thresholds, and the presence of a diode array spectrum for each pure sample in the wells of the collection plate.
Figure 7:
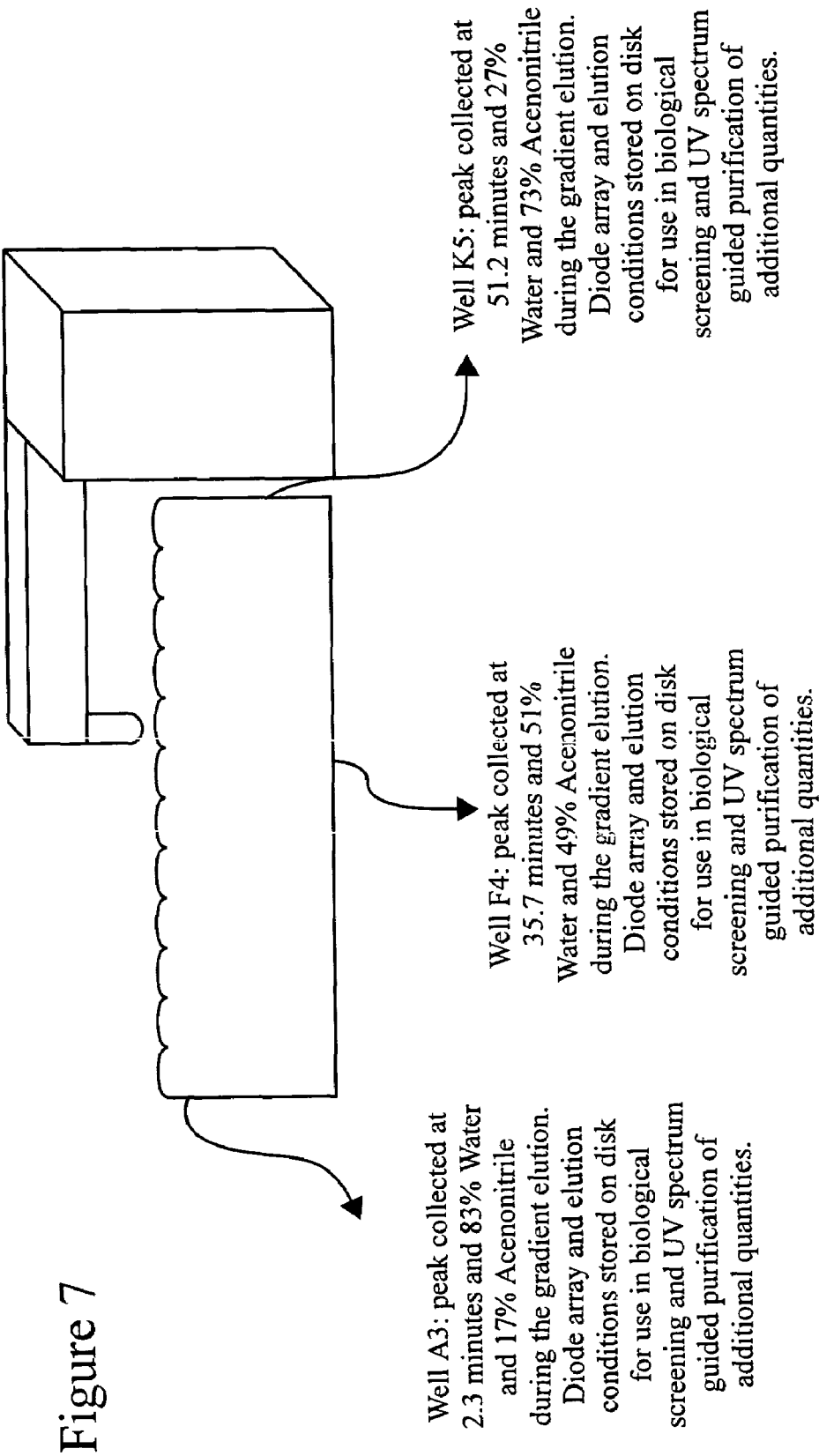
FIG. 7 is a diagram of the contents in wells of a collection plate containing isolates of the invention, wherein the contents of three randomly selected wells is described.
Figure 8:
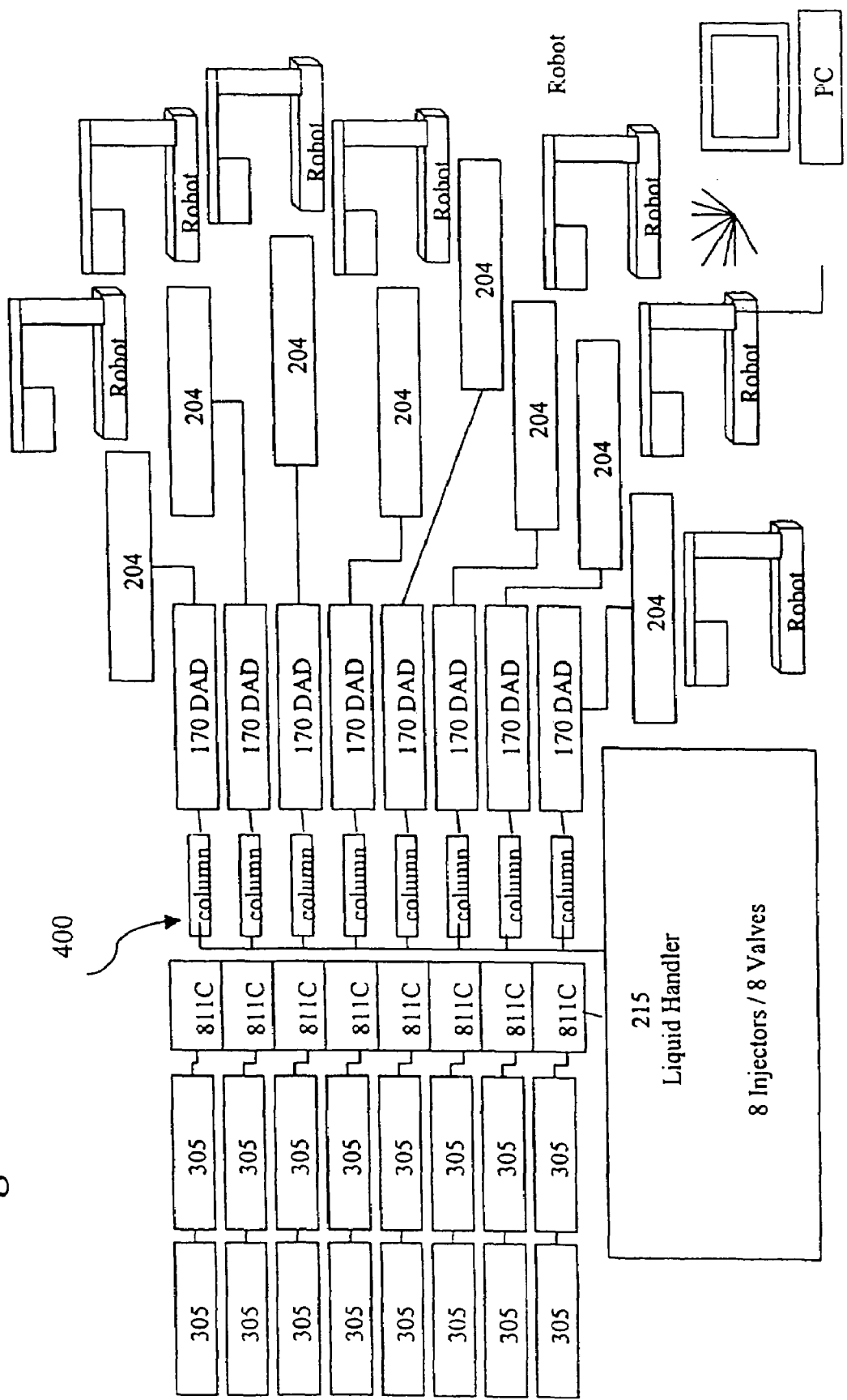
FIG. 8 is a schematic representation of a second chromatography or purification step.

This application is related to PCT application PCT/US00/30195, published as WO 01/33193, and U.S. patent application Ser. Nos. 60/280,739 and 60/328,788, all of which are incorporated by reference in their entirety in the present specification.

In accordance with the present invention, it has been discovered that by removing from a mixture of compounds, such as a biological sample, certain components that tend to be present in relatively high concentrations but are of little interest and normalizing the concentration of compounds in the mixture that are of potential interest, and normalizing the concentrations of those compounds of potential interest, an array of samples of the normalized compounds can be produced that is suitable for high-throughput screening of the array for identification of activity of compounds of potential interest that are otherwise missed by such screening techniques either due to masking by the components of little interest or the low ambient concentrations of the compounds of potential interest. Remarkably, such techniques have been discovered to permit the detection of desirable properties for thousands of compounds that are missed by conventional screening techniques.

Accordingly, the present invention allows hundreds of chemical compounds per biological source to be tested in biological systems at optimal screening concentrations. Prior to the present invention, this remarkable advantage was not attainable. Because extracts from biological sources being tested typically have constituted approximately 80% by weight of non-drug-like chemical compounds, conventional techniques have allowed only the major drug-like chemical compounds from the extract to be tested at screening concentrations familiar to those skilled in the art of biological screening for the discovery of new medicines or agricultural products.

Thus, the present invention solves problems inherent in the prior art of preparing compounds from biological sources for biological screening and, in contrast to the prior art, may be used to produce from a biological source large numbers of chromatographic fractions that contain chemical compounds of potential usefulness, but that are predominately free of non-drug-like chemical compounds. The fractions not only may include scientifically useful information, but are organized in a logical manner. Moreover, by identifying duplicate chemical compounds in biological collections, thus removing the possibility of discovering the same chemical compound from a different biological source, the invention also provides further advantages that were not previously appreciated. Results obtained using the invention also provide for rapid isolation and structural elucidation of therapeutically useful compounds.

This invention also achieves a goal previously thought to be unattainable, that of harnessing plant biodiversity with the high-throughput approaches of combinatorial chemistry and automated screening. Combinatorial chemists have typically viewed plant material as too complex to use as starting material for the structural variation that is typical in generating combinatorial libraries. By providing an ordered collection of relatively pure phytochemicals, the invention permits the study of a vast new array of phytochemical structures and their evaluation for biological activity such as in treating diseases or providing useful agricultural traits. The present invention has aspects in the mature art of collections of chemical compounds from biological sources and other aspects in the crowded field of high throughput screening, none of which aspects had been combined before.

The separation method of the present invention, therefore, produces a library that contains a much greater number of purified, relevant drug-like chemical compounds per plant for biological screening than currently used by those skilled in the art. The library allows hundreds of chemical compounds per plant to be tested in parallel in biological assays at optimal screening concentrations and is particularly amenable for use in the high-throughput screening of chemical compounds purified from plants in biological assays.

This invention is contrary to the teachings of the prior art and differs from the prior art in several modifications neither previously known nor suggested. For example, prior art plant extraction methods have generally relied on liquid extraction of plant biomass to provide a single extract or a few (generally less than four) extracts into different solvents. The general belief is that a single extract or small number of extracts is adequate for biological assays because of the sensitivity of bioassays, and, in addition, it is easy and routine to process plant material in this fashion. The National Cancer Institute and many commercial pharmaceutical research laboratories follow this approach. There has traditionally been no motivation to provide further fractionation of the extracts before screening, the philosophy being that if an extract provides a hit, bio-assay guided fractionation can be performed thereafter. To the extent more than one extract was desired, the effort has been to accomplish this goal by selective liquid extraction (e.g. low polarity first, then increasingly high polarity extraction solvents), in the belief that this would provide different populations of phytochemicals.

The prior art has avoided pre-screening chromatography presumably because it was seen as complicated and unnecessary. Counter to the accepted view, it has been found that the prior extraction-based approach to providing fractions of phytochemicals is flawed because concentrations of most chemical compounds in such fractions are below optimal screening concentrations and are not present in normalized quantities. Moreover, numerous non-drug-like chemical compounds in such fractions reduce the effective concentrations of drug-like chemical compounds and interfere with the activities of the drug-like compounds.

The library of the present invention, therefore, provides advantages that were not enjoyed in the prior art. For example, the library of the present invention can provide a comprehensive purified collection of the potentially biologically-active phytochemicals from plants, without significant concentrations of non-selectively interfering chemical compounds from the plants, thus resulting in a population of the potential, selective biologically-active phytochemicals susceptible to testing and screening by conventional techniques. The separation of the chemical compounds in the collection surprisingly according to the present invention reduces problems in high-throughput screening, such as masking of biological activities of one chemical by another and allosteric regulation of receptors by multiple components. The compounds are present in the library of the present invention in normalized amounts, and have a tight range of molecular weights, yielding a tight range of concentrations suitable for assays. The association with data allows for rapid extraction of meaningful date from the biological assays. The library of the present invention contains chemical compounds having a higher yield of phytochemicals of interest as compared to conventional methods, both in terms of chemical diversity and higher total mass.

Also, the library of the present invention solves problems encountered in prior art methods with solubilities of phytochemicals, because the solubilities of phytochemicals are revealed, facilitating the design of the screening system (e.g. identification and selection of solvents to use) and greatly accelerates preparation and purification of a compound that provides a hit. That is, the invention provides a solubility and fractionation profile for each fraction that can be used both as an initial indicator of the chemical nature of the isolated chromatographic fraction, can help as a first step in elucidating the structure of the compound, and the fractionation data can be used to refractionate a larger quantity of the material for further analysis in the event it becomes a lead by virtue of a positive result in a biological assay. The small scale fractionation and chromatography producing a small mass chromatographic fraction can be readily scaled up with more plant material and a larger column to provide the same chromatographic fraction in larger yield, thereby shortening the time needed to design a purification procedure and hasten structure elucidation.

This invention also satisfies a long felt need for a biologically-suitable, efficient way to test the potentially selective biologically-active chemical compounds from a wide variety of different types of biomass with associated data useful in further research on the chemical compounds.

In summary, the present invention provides an array of chromatographic fractions from biological sources with properties selected for efficient high throughput screening. The selected fraction properties include fractions that, for example:

contain predominately compounds having low molecular weights in a range where biological activity is likely to be found. This range may be, for example, molecular weights less than 6000, 3000, 1,000, 600 or even 300 daltons, as desired;

are free of—or at least free of significant amounts of—compounds likely to interfere with biological assays by nonspecific binding, such as compounds with molecular weights greater than about 3000 or 6000 daltons, for instance, tannins and tetramers or greater of phenolics, and compounds having log P's greater than about 5 or 6 or less than about −1 or −2;

contain a limited number of compounds, for example, less than about 5 or 7 compounds;

contain a known, normalized mass quantity of each chemical compound suitable for preparing a sample that may be used for biological screening (which quantity may be between 1 microgram and about 100 to 500 micrograms to be suitable for presently available screening methodologies);

fall within a predetermined range of molecular weights (typically about 300 to about 1000 daltons, such as from about 250 to about 600 daltons), so that a normalized mass gives a normalized molar concentration; and may have associated data used to identify specific compounds and/or replicate the isolation to allow accumulation of additional fractions with the same characteristics.

The present invention thus provides a chemical compound library comprising of a plurality of chromatographic fractions, wherein said chromatographic fractions contain from about 1 microgram to 100 micrograms of primarily of one to five chemical compounds; wherein said chemical compounds have log Ps of greater than −1 and less than 5 and molecular weights less than 3,000 Daltons; wherein said library comprises of said chemical compounds produced from at least fifty different biological sources; and wherein said library contains at least 200 (such as from about 200 to about 700) of said different chemical compounds from each different biological source.

The library may comprise at least 80, 100, or 150 chromatographic fractions from each different biological source and each chemical compound within the fractions may have a molecular weight of less than 10,000 Daltons. The library also may include associated data sufficient to identify the relative amounts of said chemical compounds in said chromatographic fractions and the associated data may be used to increase the diversity of chemical structures of said chemical compounds, and for analysis to select the biological sources for the library. In preferred embodiments, the chromatographic fractions are free of tetramers or greater of polyphenolics, and the weight of the chemical compounds of each chromatographic fraction is approximately 100 micrograms to about 500 micrograms of solid material of primarily of one to five chemical compounds.

The following definitions apply to the indicated terms as used in the present specification:

Definitions:

As used herein, the term "natural product" means a product obtained from biological sources such as plants and animals. A natural product may be single compound or a mixture of compounds derived from biological sources.

As used herein, the terms "screening" and "biological screening" means any method used to detect biological activity of a sample. These terms include in vivo and in vitro testing, including bioassays.

As used herein, the terms "chemical interference" and "interference" generally refer to one or more chemicals or other material present in natural products that may give rise to an inaccurate result during screening. An inaccurate result may be a false positive or a false negative.

As used herein, the term "hit" is a positive result in screening given by a compound, fraction or other sample.

As used herein, the term "high throughput screening" means a screening method able to test invitro a relatively large number of samples in a relatively short period of time to detect samples that exhibit a biological effect. Generally, high throughput systems are automated and require little human intervention.

As used herein, the term "progeny" refers to compounds derived from a common source (e.g. biological resource).

Progeny may be derived from the original source through one or more purification steps.

As used herein, the term "fraction" means any sample that is part of a larger whole.

As used herein, the term "isolate" means a chromatographic fraction containing a mixture of one to five drug-like compounds. It is a final sample suitable for testing. An isolate may be derived by one or many purification steps. A set of isolates arranged in an array of the invention may comprise progeny having a common ancestor source. All isolates are fractions. Fractions may be used as final samples and when used as such may be referred to as isolates.

As used herein, the terms "automation" and "automated system" refer to a means or apparatus that functions with a minimum of human intervention. Usually automation requires computer control. A system is considered automated even though it requires some human control, input and/or programming.

As used herein, the term "chromatography" specifically includes normal and reverse phase systems, solid phase extraction and other methods conducted using a column, including high pressure systems and vacuum systems. The definition of chromatography as used herein is not otherwise limited, but has the general meaning that is well understood in the art.

As used herein, the term "identifying system" is any system capable of correlating a physical entity and information or data related to that physical data. An identifying system may have a physical manifestation, such as a bar code or may be only data stored electronically. Thus, while an identifying system must track a physical entity, it need not have a component physically attached to the entity.

As used herein, the term "assay concentration" refers to the amount of a compound in a given volume of sample that has been prepared for a biological assay.

As used herein, the term "normalized assay concentrations" refers to concentrations of compounds that are orders of magnitude—typically, from tens to thousands of times—larger than the original concentration of a major component in the extract from a biological source material when a crude extract of the biological source materials is prepared for biological testing, but within an order of magnitude of each of the concentrations of the other major components in the isolate prepared from the extract.

As used herein, the term "major component" refers to any of the most prevalent of the potentially selectively bio-active compounds in a crude extract, at a concentration typically sufficient to exhibit a primary biological activity. A typical plant, for example, may contain about 10-20 major components, typically 12-15 major components, using conventional screening assays.

As used herein, the term "detectable compound" refers to a compound that is detectable by mass spectrometry or evaporative light scattering detection.

As used herein, the term "potentially selective bio-active compounds" refers to such compounds as described above and elsewhere herein as having the possibility for usefulness as a drug or other agent that induces a biological response, and typically includes certain classes of organic compounds in the catalog of isolates known to those of skill in the art. The classes are broad, and may for example include some or all of the following, or others:

| | | |
|---|---|---|
| Acetylene | Alkaloid | Alkaloid glycoside |
| Benzofuran | Benzophenone | Cardenolide |
| Chalcone | Coumarin | Cyclic peptide |
| Diketopiperazine | Diterpene | Flavan |
| Flavone | Flavonoid | Flavinoid Alkaloid |
| Furanoquinoline Alkaloid | Geranylstilbene | Hydroquinone |
| Indolequinone | Isoflavanone | Isoflavanoid |
| Isomalabaricane diterpene | Lactone | Lignan |
| Macrolide | Monoterpene | Napthoquinone |
| Phenyl Glycoside | Pyranocoumarin | Quassinoid |
| Quinoline | Sesquiterpene | Sesquiterpene Quinone |
| Steroid | Steroidal Saponin | |
| Triterpene | | |

As used herein, an "array" is a set of fractions or isolates arranged in a particular format, such as a group of chromatographic fractions from a single biological source, a group of fractions from different biological sources, a group of fractions selected for having similar or diverse molecular ion, partition coefficient (log P), and so forth. An array is typically a microtiter plate useful for high throughput screening, or an intermediate format useful for preparing such a plate. At least a useful proportion of fractions in an array include chemical compounds in an amount suitable for high throughput screening. For end-user arrays, all the fractions contain "normalized" amounts of compounds, as will be defined below.

As used herein, the term "suitable for high throughput screening" means an amount, number and format that takes into account automated screening methodology and/or economics. For example, using currently available methodology, a suitable amount of each compound may comprise at least about one microgram per assay, and/or an amount which is suitable to prepare samples of about one micromolar solution. Thus, a well with 20 micrograms of compound per well may be sufficient to conduct about 20 biological assays. It is understood that, as technology changes, the amount of a chemical compound corresponding to a suitable amount may increase or decrease. The economics involved require having a suitable diversity of compounds, and large enough quantity of material available to run a number of biological tests so as to justify the cost of the isolation and disposable materials on which the fractions are dispersed and the load factor for running a biological assay.

As used herein, the term "chromatographic fractions" includes subfractions derived from a first chromatographic fraction.

As used herein, the term "small number" in reference to compounds is a number that allows biological activity from any one compound in the mixture to be detected without interference from any other compound in the mixture. A number of compounds that is small enough to prevent interference due to competition and to minimize collision frequency is typically less than about 7 compounds or about 5 compounds. The small number provides a substantial purity, e.g. at least about 80%, or 90%, or 95% of the mass of the compounds in a given well is in seven or fewer, or even five or fewer compounds. A person of ordinary skill will recognize that for all the characteristics of the compound isolates, there is a range of characteristics. For the number of compounds, generally there will be fewer than about 5% of isolates that include 6-7 detectable compounds, and fewer than 1% that contain 8 or 9 detectable compounds.

As used herein, the terms "substantially free of compounds that interfere with biological testing" and "substantially free of interferences" in reference to a fraction or isolate mean that the fraction or isolate is substantially free of compounds that may non-selectively compete with the compounds of interest for the active site of potential targets of biological activity. "Substantially free," as used herein, refers to a non-interfering amount. In other words, in a fraction that is substantially free of compounds that interfere with biological testing or substantially free of interferences, any compound present that may so interfere by non-selectively compete with the compounds of interest for the active site of potential targets of biological activity is present at a concentration too low to cause such interference. Such compounds or "interferences" that are removed include: (a) compounds having a high molecular weight, for example a molecular weight greater than 25,000; 10,000; 6,000; or 3,000 dalton; depending on the situation and the molecular weights of the compounds of interest; (b) tetramers or greater of phenolics; (c) tannins; (d) proteins; and (e) peptides. Such fractions are "non-proteinaceous," meaning that the chemical compounds do not comprise proteins or peptides. Proteins may interfere with biological testing of the individual compounds.

As used herein, the term "an amount sufficient to prepare a sample of a concentration suitable for biological testing" means an amount of compound sufficient to prepare a sample having a concentration of that compound useful for bioassays; that is, an amount detectable or responsive in the bioassay to be employed. Typical amounts required for current known bioassays are about 1-100 micrograms. This amount can be used to prepare samples from the fraction having a concentration of at least about one micromolar. As bioassay techniques improve and become more sensitive, the amount of compound and the concentration may be reduced.

As used herein, the term "drug-like compounds" refers to compounds exhibiting molecular weights less than 1000 daltons and lipophilicities (log P) less than 5 and approximately greater than 0. These specifications were derived from the analysis of drugs by researchers at Pfizer which demonstrate good permeability across a membrane bi-layer. See, for example, Lipinski, et. al., Experimental and computational approaches to estimate solubility and permeability in drug discovery and development settings. Advanced Drug Delivery Reviews 46 (2001) 3-26. Preferably, the drug-like compounds have molecular weights less than 500 daltons.

As used herein, therefore, the term "non-drug-like compounds" refers to compounds that do not correspond to the definition of "drug-like compounds." Applicants' analytical data demonstrate that approximately 80% of a plant extract by weight consists of non-drug-like compounds. Applicants' purification procedure was specifically developed to remove most of the non-drug-like compounds during its process and collect the drug-like compounds into chromatographic fractions.

As used herein, the term "a log P suitable for biological testing" means a log P (partition coefficient) within a range typical of biologically active compounds: −2 to 6 or −1 to 5. This is determined by the chromatographic parameters. Compounds such as fatty acids, log P 6-11, are desirably excluded. As methods change, this range may increase. It may also be possible that the biological activity of compounds with log P's outside this range may be measured and the 15 active compounds chemically modified to bring the log P within a suitable range.

As used herein, the term "normalized quantity" means a known mass that may be used to prepare a sample having a known concentration. A normalized quantity of a compound is ten to thousands of times greater than that found in an extract, but is within a single order of magnitude with respect to the concentration of other normalized concentrations from that extract. A "normalized quantity" of a chemical compound or compounds is a known amount of material removed from the fractions of the original "mother" plate or intermediate plate as needed so that the known amount of the compounds on the end-user plate is within a predetermined concentration range and suitable for high throughput screening. The predetermined concentration range allows specific activity to be detected directly from a biological assay of the fraction. It also ensures that the amount of compound is suitable to provide a positive result from a biological assay if the compound is biologically active. A normalized quantity may be prepared using approximate mass data collected by ELSD which gives information about the total mass in each fraction. A normalized quantity may be prepared in a separate plate by taking an aliquot from the fraction sufficient to transfer the predetermined mass necessary to give a desirable concentration when diluted in the array, e.g. between about 1 micromolar and 20 micromolar. The approximations involved are well within the degree of precision required by persons of ordinary skill in the art to which the invention relates. Mass spectral data gives information about the approximate molecular weight of compounds in the fraction. Coupling such information with the mass permits compound by-compound calculations of molar concentration.

As used herein, forms of the term "normalizing"(e.g., "normalization" and "normalized: as well as "normalizing") in reference to quantities or concentrations of a group of compounds, such as compounds within a fraction or extract, means increasing and adjusting the quantities or concentrations of the compounds such that each of the normalized quantities or concentrations is an amount sufficient to prepare a sample of a concentration suitable for biological testing—a concentration generally tens to thousands of times greater than the concentration in the original extracts—and such that each of the normalized quantities or concentrations is within about an order of magnitude of each of the other normalized quantities or concentrations in the group. Preferably, the quantities or concentrations are such as to be suitable for high throughput screening.

As used herein, the term "organism" refers generally to a plant but can also be, for example, bacteria, insect, marine microorganisms, and fungi, etc. Different organisms may be, for example, different genera species of a plant or different types of microorganisms, for example a plant and a fungus, or combinations thereof.

With these definitions in mind, therefore, according to one embodiment of the present invention, a sample is extracted from a biological source such as by liquid extraction, interferences are removed from the sample, fractions are derived from the resulting interference-free sample such as by automated distribution and solid phase extraction, the resulting fractions are purified, concentrations of compounds of potential interest are normalized, and the normalized compounds are distributed on a screening plate suitable for screening by high-throughput screening techniques.

The screening plate as described is a physical array of progeny isolates obtained by fractionating a single biological source, each isolate comprising from one to five compounds of about 250 to about 600 Daltons (typically not protein or nucleic acid) collected on a physical supporting medium, and associated therewith a data array including the identity of the biological source, the location of each isolate, the fractionation conditions by which each isolate was obtained and preferably physical and/or chemical information regarding the compound, most preferably including its elucidated structure. The invention thus provides both a physical/chemical catalog and a data catalog of the organic compounds found in the biological source. These organic compounds may be separated into ultraviolet absorbing and non-ultraviolet absorbing arrays. The physical array and the data array each have independent value and usefulness for screening in vitro and "in silico" (virtual screening using computer modeling), but they are most useful when combined. In short, screening plate is a physical array of isolate samples wherein each isolate sample comprises a small number of components at or near the assay concentration. The small number of components may be less that 100, is preferably less than about 15 and is most preferably no more than about five. The isolate sample may be prepared from one or more extracts that have been subjected to one or more chromatography steps.

For greater clarity, reference is now made to a non-limiting illustration of the process of the present invention. According to the present invention, a plant may be processed to produce an extract from which a sample is loaded onto a flash column, producing a small number of fractions—say for the sake of discussion, five solvent fractions labeled E1-F1 (meaning fraction 1 from extract 1), E1-F2 (fraction 2 from extract 1), E1-F3 (fraction 3 from extract 1), E1-F4 (fraction 4 from extract 1), and E1-F5 (fraction 5 from extract 1). Fraction E1-F1, which is very lipophilic, is discarded, and some material is lost due to irreversible bonding to the very hydrophilic column. Because the discarded and lost materials do not fall within the lipophilicity range associated with drugs, they are not considered potential drugs and in prior art processes are interferences that inhibit detection of legitimate drug possibilities in the sample. Fraction E1-F2 is loaded onto a preparative HPLC column and numerous fractions are collected. To distinguish such fractions from the mother fraction E1-F2, these will be referred to as daughter fractions. For the sake of discussion, say forty daughter fractions are collected from mother fraction E1-F2. The same procedure is followed with fractions E1-F3, E1-F4 and E1-F5, thereby producing more daughter fractions. Each of the daughter fractions is then transferred to a well, one daughter fraction per well, and analyzed by a combination of HPLC, MS and ELSD. The total mass or weight of each daughter fraction is determined by ELSD. The amounts in the wells are then normalized. Normalization may be carried out by transferring approximately the same mass of material (preferably each mass should be within about twenty percentage points of each of the other masses) from each well to a corresponding well on a screening plate. This may be carried out in a two-step procedure by diluting each daughter fraction, the greater the material the greater the degree of dilution, and transferring the diluted daughter fractions from their wells to corresponding wells on a screening plate. The volume of each diluted daughter fraction that is transferred is such as to result in approximately the same mass of material in each well, that mass being "an amount sufficient to prepare a sample of a concentration suitable for biological testing" as that term is defined above. Thus, typically such amount is about 1 to about 100 micrograms. Generally, about 20 micrograms may be desirable.

In greater detail, normalization may be carried out as follows. After preparative HPLC the HPLC fractions are transferred to 96 well plates for HPLC/ELSD/MS analysis. The results of the ELSD estimated weight for each well are processed by software and sent electronically to a Packard Multiprobe II Liquid Handling system. The software categorizes mass of the well into one of four categories. The well of each preparative HPLC fraction will nominally contain 0, 200, 500 or 1000 μg of a preparative HPLC fraction. Wells with 0 mass are excluded the final plate map prepared by the Extractor software. Plates prepared for screening typically contain 10, 20 or 50 μg of isolates/well.

Before processing with the liquid handling robot, a new excel spreadsheet is prepared. This spreadsheet is called a client plate map and contains data from the Extractor spreadsheet, and four additional columns. The columns are 'fill volume' and one column each for the amount of volume needed to remove the proper mass (10, 20 or 50 μg). The fill volumes and 'aspirate volumes' are prepared via Microsoft Excel® VBA code. The code uses simple algebra to calculate the fill volume and aspirate volumes. For example; if the source well contained 200 μg and the client required 50 μg (¼ of the mass) the fill volume would be 300 μl and the aspirate volume would be 75 μl (¼ of the volume). Technically if the source well contained 1000 μg and the client plate required only 10 μg (1% of the mass) then the fill volume would be 500 μl and the aspirate volume would be 5 μl; however, the liquid handling system is not precise below 10 μl. In the case of 1000 μl, samples and 10 μg requirements the spreadsheet is programmed to calculate a fill volume of 500 μl and an aspirate volume of 10 μl. This allows for more precise liquid handling, but creates a situation where some wells have 2× concentration of sample.

In any event, the amounts should be suitable for high throughput screening. This screening plate is therefore an array that is a library of the characteristics and advantages as discussed above. The library is suitable for high throughput screening that allows an investigation of the characteristics of individual compounds or groups of compounds on the plate whose characteristics are missed by conventional screening techniques due to the presence of the interferences removed with fraction E1-F1, above, low concentration of compound or group of compounds, or a combination of the two.

In more detail, the steps of a process of an embodiment of the present invention is as follows: Extraction may be carried out by grinding dried plant material to a homogenous powder and sonicating the powder in an organic solvent, such as a mixture of EtOH:EtOAc (50:50), and shaking the resulting mixture vigorously for exhaustive extractions.

Next, flash chromatographic separation may be carried out by dissolving the organic extract in 5 mL of a solvent such as MeOH:EtOAc (50:50), adsorbing it onto silica powder and bringing the dried powder onto a silica column and eluted on the flash chromatography system using a step gradient of 1) 75% hexanes, 25% EtOAc, 2) 50% hexanes, 50% EtOAc, 3) 100% EtOAc, 4) 75% EtOAc, 25% MeOH, 5) 50% EtOAc, 50% MeOH. The flash fraction containing highly lipophilic material unsuitable for drug possibilities may be discarded, whereas the ramaining fractions may be dried, such as by rotary evaporation. One or more flash fraction may be screened for the presence of tannins by LC-MS and passed over a polyamide column if results are positive. See Anderson, K. J.; Teuber, S. S.; Gobeille, A.; Cremin, P. A.; Waterhouse, A. L.; Steinberg, F. M. *J. Nutr.* 2001, 131, 2837-2842.

An aqueous extract may be dissolved in water and the resulting mixture centrifuged. The resulting aqueous layer may be brought onto a C18 column (pre-rinsed with 1 column volume methanol and 5 column volumes water). Any insoluble material may again be dissolved in water using sonication and the suspension may be centrifuged again. The aqueous layer may also be brought onto the column. The column then may be rinsed with water and the effluent discarded. The remaining insoluble material subsequently may be taken into methanol and the methanol layer brought onto the column. The column may be eluted with methanol to remove water from the column and a polyamide cartridge in methanol may be attached to the bottom of the column. The column then may be eluted with methanol. The resulting fraction may be dissolved in MeOH:H2O (60:40) and filtered with a molecular weight cut-off of 3000 amu. The retentate, typically 1-2 mL, may be discarded. Analytical size exclusion chromatography has shown that the content of high molecular weight constituents (>3000 amu) in the filtrate is reduced significantly from up to 75% to less than 10% of the total amount of material using ELSD detection.

Preparative HPLC separation may then be carried out. Flash fraction material may be dissolved into either MeOH:EtOAc (70:30) or 100% MeOH and filtered where necessary. The fractions are separated into several dozen, such as 40, fractions using a device such as a parallel four-channel preparative HPLC system. A different gradient may be applied to each flash fraction for adequate separation; for example, flash fraction 2: 40-80% acetonitrile in water, flash fraction 3: 30-70% acetonitrile in water, flash fraction 4: 20-60% acetonitrile in water, flash fractions 5 and 6: 10-50% acetonitrile in water. The tubes (e.g., 40 tubes for 40 fractions) containing HPLC fractions may be dried in an evaporator. The HPLC fractions then may be transferred to plates such as 96-deep-well plates using a liquid handling system (e.g., Packard MultiProbe II).

The mass or weight and the molecular weights of the materials in the samples may be determined by a parallel eight-channel LC-ELSD-MS system with chromatographic conditions of 5% acetonitrile in water for the first minute, a linear gradient of acetonitrile from 5% to 95% in eight minutes, followed by 95% acetonitrile in water for a minute. Under such chromatographic conditions, the column is equilibrated at 5% acetonitrile in water after each analysis. Data processing for determining the appropriate dilution for each sample for normalization may be performed automatically with computer software to extract all graphic information, such as retention times, mass spectra, and peak integrations, and to convert such information to text to allow it to be transferred to a database for storage and analysis.

Based on the knowledge of the amounts of material present, normalization may be carried out so that the mass of material in each well is about the same (i.e., within about an order of magnitude, preferably within about 20 percentage points of each other), and the mass of each significant compound within each well is about the same as the other significant compound in that well (i.e., within about an order of magnitude, preferably within about 20 percentage points of each other). The reference to "significant" compounds as opposed to all compounds is in recognition that in addition to the small number of compounds to be studied in the well, there may be additional compounds present in relatively tiny amounts and those may be ignored. For example, a well might contain three or four compounds varying in mass from about, say, 30 micrograms to 50 micrograms, as well as extraneous compounds of mass on the order of, say, 1 to 2 micrograms.

Such well may be considered normalized notwithstanding the presence of low amounts of the extraneous compounds. Although a logically ordered preparation of arrays of synthetic compounds from certain scaffolds has been previously described, for example in U.S. Pat. No. 5,962,736, the present invention provides a systematic method for providing arrays of plant isolates or isolated pure compounds that are fundamentally different from all known prior art. For example, although prior art methods prepare an ordered array of known target compounds, the invention is fundamentally different in providing an array of unknown, non-target compounds for testing. In addition, although the prior art arrays were generated by isolation or synthesis of single compounds, arrays of the present invention are generated through fractionation of complex mixtures of compounds. Although the identifying system of the invention removes the necessity for preparing orderly arrays, providing for the ordering of the arrays of isolates in a logical manner is preferred. These arrays may be constructed from a wide variety of fractionated plant isolates, but other fractionated natural product isolates or isolated compounds, including but not limited to marine organisms, microorganisms, and insects, are within the scope of the invention.

In a preferred embodiment, the invention provides a layout of arrays of isolates in microtiter plates that contain various unknown compounds for screening in biological systems. The invention provides that the solubility profile of each isolate is known. The arrays are preferably ordered in such a fashion as to expedite collection of the isolates and provide insights into the solubility of the compounds specific to each array. This method has great utility in accelerating the discovery of compounds by providing information about the physical properties of the chemicals in the isolates before the screening process.

The preferred arrays are constructed from ordered gradient elution schemes developed with consideration of the origin of the solvent fractionated isolate and the solid phase extraction sorbent that may retain compounds in the mixtures. Each group of arrays consists of sets of solubility related isolates which may contain approximately one to fifty compounds per isolate with a common solubility profile and various structural diversity when a purification step is included in the method, isolates typically contain one to three compounds. These arrays may be arranged in larger groups of arrays consisting of sets of arrays and tested to provide information regarding all of the isolates in the arrays. For example, the larger groups of arrays may originate from different regions of the same plant and be ordered by the plant from which the isolates originate. A set of such arrays would thus represent a parent plant and a set of isolates that are the progeny of that plant.

For a serial fractionation chromatography system having one or more independent columns (such as eight as described with the Gilson liquid handling system), the first fraction is collected e.g. in column 2, row A, the second fraction is collected in plate 1, column 3, row A, and so on until column 11, row A, then the fractions would be collected in row B from column 11 back to column 2, and so on. An extract being separated might have from 5 to 150 compounds that can be separately isolated. When the last compound of a sample is collected, the collector then takes another extract and begins chromatography on that extract, collecting in the well after the last fraction of the previous extract. Thus, a plate might have the extracts from several plants arrayed on it, or a plant might require several plates to capture all the compounds.

The array of fractions or isolates thus comprises a large number of individual isolates that are related as being, for example, the progeny of a single plant or originating from a particular taxonomic division of plants. The large number of isolates in each array is preferably at least about 10 and most preferably at least 50. It may be larger than the number of wells on a plate, in which case the array includes several plates. The number of individual, unique isolates can be represented by M which is a function of P, S, E, F and A in which:

P is the number of plants used to generate the extract samples;

S is the number of samples obtained from different parts of each plant;

E is the number of solvent extracts taken from each sample,

F is the number of fractions obtained from each solvent extract, the fractions F being obtained by a first chromatography step; and A is the number of subfractions collected from a second chromatography step of each fraction. The maximum value of M may be represented as:

$$M = P \times S \times E \times F \times A \quad (1)$$

In equation (1), P is defined as the number of plants used to generate an array of isolates. For a particular set of isolates, P is preferably from one to ten and is most preferably one. S is the number of samples obtained from each plant. For example, if leaves, stem and root are used, S is three. It is preferred that S be from one to five. E is defined as the number of extracts taken from each sample. In a preferred embodiment, E is from one to three. Most preferably, E is two. The number F is defined as the number of fractions collected from each extract. In the preferred method of generating the M isolates that comprise the array, E is the number of fractions collected by solid phase extraction and is preferably from three to twelve. A most frequently represents the number of fractions collected from the further purification system, when utilized. If the further purification system is not utilized, A is assigned the value of one. In a preferred embodiment of practicing the invention that includes the further purification step, A is from one to twelve. Preferably, E*F*A is greater than 10, more preferably greater than 15.

It is contemplated that for each of P, S, E, F, and A, there can be a different number of products. That is, for each plant there can be a different number of samples; for each sample, a different number of extracts; for each extract, a different number of fractions; and for each fraction, a different number of subfractions. For example, for a given plant sample, there may be two solvent extracts (polar and nonpolar), one of which produces three fractions and the other of which produces six fractions, for at total of M=9 isolates.

The ordered arrays of the invention are unique in that (a) they include essentially all of the significant phytochemicals (those having a potential selective bio-activity) because all have been extracted by thorough extraction, and none have been passed to waste due to careful detecting of the chromatography eluent, (b) each well of the ordered array has at least one detected compound (none are blank), and (c) the wells do not have more than a few compounds.

The array of isolates thus represents a physical catalog of related compounds. Associated with each isolate is a data array. Thus, in addition to the novelty and utility of arrays of isolates, each individual isolate and its associated data is also novel and valuable. Each individual isolate has associated therewith data useful for replicating test results and for the isolation of biologically significant compounds. The data array forms a "virtual catalog" of properties that mirrors or shadows the physical array of compounds. Much of the valuable information in the physical catalog is also contained in the virtual catalog. Thus, the data label itself that is associated with each isolate has value, particularly if structural data is associated with such data.

In another embodiment of the invention, isolate samples may be packaged on, for example, sample plates wherein each sample on the sample plate contains a small number of detectable compounds. Preferably, the small number of detectable compounds is less than about 100, more preferably is less than about 15 and most preferably is no more than about five. According to this embodiment, a biological source material is extracted with at least one extraction solvent to give one or more extracts. The interferences are preferably removed from each extract. Each extract is then subjected to at least one automated chromatography as previously described. Fraction collection may be conducted by an automated detection system or by time dependent collection. The individual fractions are then analyzed. Fractions that do not contain detectable compounds may be discarded.

Fractions are then distributed on sample plates such that each isolate sample contains an amount (that is, "quantity" as opposed to number) of detectable compounds which, upon preparation for a biological assay, contain the detectable compounds in an amount equal to or greater than the normalized assay concentration. Thus, fractions that contain detectable compounds in excess of the amount required for preparing a normalized assay concentration may be subdivided into multiple isolate samples and distributed on more than one sample plate. Fractions containing an amount less than the amount required for preparing a normalized assay concentration may be combined with other fractions having a similar composition. Using this method, about four to five sets of sample plates may be prepared in a single sequence.

Thus, in one embodiment, the present invention is an article of manufacture that is a library or collection of chemical compounds with unique and identifiable chromatographic separation parameters. The library of chemical compounds may be distributed, for example, on a plate, particularly a microtiter plate, that is suitable for use in an automated bioassay instrument. In preferred embodiments, a single source material (from one or more organisms) is used to produce the library of chemical compounds. The source material may be divided into greater than 80 fractions with a minimization of overlapping compounds in the various fractions. Thus, most separate fraction includes between about 1 and 5 compounds detectable by mass spectrometry, evaporative light scattering or other detection means. In addition, the chromatographic fractions may be treated to remove or minimize interferences from tannins and polyphenolics. Thus, chemical compounds prepared according to the invention do not contain interferences or polymeric compounds, but may include, for example, non-detectable amounts of other chemical compounds without changing the basic and novel characteristics of the invention.

Although all of the primary (mother) fractions collected may contain material which is detectable using, for example, evaporative light scattering, TIC mass spectral analysis, or other mass spectroscopic detection techniques, in preferred embodiments, the wells or fractions containing detectable compounds are placed in a secondary well or on a secondary plate for further analysis. These thus form secondary (daughter) plates of compounds. The secondary daughter plates may in turn be used as a stockpile or intermediate to prepare normalized end-user plates. In this way, the analytical plate that forms the article of the invention may exclude wells from the original chromatographic separation that do not include detectable organic compounds (blanks).

Thus, the invention provides a library of chemical compounds, typically contained on a microtiter plate, where all of the chemical compounds fall within a predetermined range of chromatographic characteristics. These characteristics may include, for example, solubility, log P, molecular weight, molecular size, polarity, mass, concentration, etc. Moreover, each of the compounds within each single chromatographic fraction have common chromatographic characteristics. For example, typical chromatographic procedures provide chromatographic fractions containing chemical compounds with similar log P and solubility. These chromatographic fractions contain co-elutable compounds under the particular chromatographic conditions used for the separation.

The array may, however, include sets of fractions having differing characteristics such as a broad range of sizes, molecular ions, log P's, polarity, etc. Thus, arrays of the invention may represent a diversity of compounds. This diversity may arise by selecting fractions with diverse characteristics from a single source or by constructing the array from a diversity of biological sources. Diversity increases the likelihood of detecting a biologically active compound. However, the natural diversity of mass and concentration of biological compounds is not helpful in biological screening, and is reduced by normalization as discussed in more detail elsewhere.

In a typical embodiment, the chromatographic separation of the biological source material is conducted in such a way that low molecular weight organic compounds are selectively placed in the wells. Low molecular weight compounds are those having molecular weight of less than 10,000 daltons, more preferably less than about 3,000 daltons, even more preferably less than about 1,000 daltons. The molecular weights of drug-like compounds are typically less than about 600, such as about 250 to about 600, daltons, and average about 400. In addition, the initial chromatography of the biological source material is conducted in a chromatographic system which has been calibrated in such a way that particular fractions elute at different times based on their log P values. Preferably, compounds are selected having a log P of between about −1 and 5. This is the desirable range for biological assays.

In addition to the chromatographic fractions of the invention, compilation of data describing characteristic chromatographic and spectral data regarding the contents of individual wells is contemplated by the invention. For example, each well will have associated with it data sufficient to reproduce the chromatographic conditions used to prepare the chromatographic fraction, including liquid chromatographic data and retention times. In addition, spectral data may include mass spectral data sufficient to identify the M+H ion, that is the molecular ion plus a proton, mass spectral fragmentation data, and NMR spectra. This data is sufficient to allow for a more rapid structure elucidation for various components in the fraction. Structural elucidation is performed manually. Thus, in addition to simply identifying the source material and chromatographic conditions used to isolate the various components from the biological source, the data is generally sufficient to replicate the separation in order to collect additional material for further characterization and identification of the specific compound obtained. Data sufficient for structural elucidation may be compiled during the initial preparation of chromatographic fractions, e.g. chromatography, or after biologically active or potentially biologically active chromatographic fractions are identified.

In a preferred embodiment, compounds from any one particular biological source are compared to data obtained from libraries of compound from different biological sources. The various biological sources may be different species of the same plants, different plants within the same family, or any other combination of biological sources.

Thus, the invention is environmentally useful in establishing the ranges of plant diversity thus encouraging the conservation of plants from as many sources as possible. The invention permits economic value of biological diversity to be realized, thus increasing the value of preserves of high biological diversity such as rainforests, and increasing conservation. The chromatographic and spectral data may be used to form sub-libraries of the parent libraries as separate articles of manufacture. These sub-libraries may be organized so as to include chemical compounds having similar, i.e. more narrow ranges, of log P. In addition, the sub-libraries may be arranged by looking at materials with similar or relatively narrow molecular weight ranges having a common biological source.

The libraries obtained by the present invention are particularly suitable for screening for biological activity. They have an enriched selectively bio-active population of compounds suitable for screening because they can be detected without interference. The libraries are also comprehensive, in that they contain the full range of compounds in a particular plant or other organism. Because the invention provides fractions having sufficient mass for use in the biological assay, for example, about 1 microgram to about 1 milligram of total material or individual compounds, or, more preferably, about 1 microgram to about 100 micrograms of total material or individual compounds, rapid throughput screening is readily applied to the libraries. Examples of biological assays which may be used are those which detect compounds useful for the treatment of disease or compounds useful for the control of biological tests. Thus, the library of chemical compounds are particularly useful when organized in well plates, for example, a microtiter well plate. Biological screening apparatus comprising these well plates are also contemplated by the invention.

After active chromatographic fractions or chemical compounds have been identified, it is within the scope of the invention to further chemically modify those compounds to provide additional libraries. In particular, the techniques of forming combinatorial chemical libraries of compounds may be applied. Thus, from a particular biological source, which may yield several hundred detectable compounds, biological testing will identify chromatographic fractions having biologically active compounds. A particular source may contain one or many of such compounds. Biologically-active compounds may then be further modified using a combinatorial chemistry approach to yield even more compounds suitable for biological screening. Thus the present invention provides not only for chromatographic fractions from biological sources, but derivatives of those chromatographic fractions.

The analysis of the library may be conducted by high throughput screening. Thus, an application of this invention is the rapid screening of isolates containing compounds that have been semi-purified and concentrated. An array of isolates is screened and the optimum isolates may be chosen for further structure elucidation and activity confirmation. The invention is extremely powerful primarily for three reasons, 1) chemicals in the plant extracts are semi-purified and concentrated when compared to traditional methods of preparing plant extracts which provides an increased probability of showing biological activity free from interferences and numerous other secondary interactions with other chemicals in the plant extracts, 2) physical property information about the chemicals in the plant extracts are provided with each extract which will decrease the time of elucidating the structure; and 3) the physical array of isolates can be used in existing high throughput screening systems developed for synthetic combinatorial chemistry applications, extending these systems to the field of biodiversity prospecting.

A method for the screening of foods for nutraceuticals has been previously described in U.S. Pat. No. 5,955,269. Methods for the biological screening of libraries of synthetic chemicals prepared from biologically active scaffolds have been described in U.S. Pat. No. 5,908,960. It is the object of the present invention to provide isolates from natural sources in an ordered array of microtiter plates that is more suitable than known to the prior art for the high throughput screening of biological assays. Steps of the preparation of the isolates have been optimized for plants to increase the success of discovering a chemical that may have a therapeutic value.

The data labels of the present invention may be independently useful screening tools. In addition to bioassays for screening of compounds, the advent of high speed computers and the wealth of knowledge regarding structure-activity relationships in recent years allows for "virtual screening" of chemical compounds. In virtual screening, a computer analyzes possible structure activity relationships in drug discovery. Thus, rather than that in vitro assays, virtual screening provides for "in silico" screening of drug candidates. The compound itself is not necessary for in silico screening, only data.

FIGS. 9 through 13 illustrate examples of the well plates of the invention, the data which may be associated with those well plates, and the file structure which may be used in a database for organizing the data obtained. FIG. 9 is a schematic representation of fractions of chemical compounds in a microtiter plate with mass spectrum and evaporative light scattering chromatograms of an individual fraction within the collection. As shown in FIG. 9, any particular well, shown here as well designated H3, has associated with it an evaporative light scattering detector (ELSD) chromatogram, a total ion current (TIC) chromatogram and a mass spectrum of the bulk material.

Figure 10:
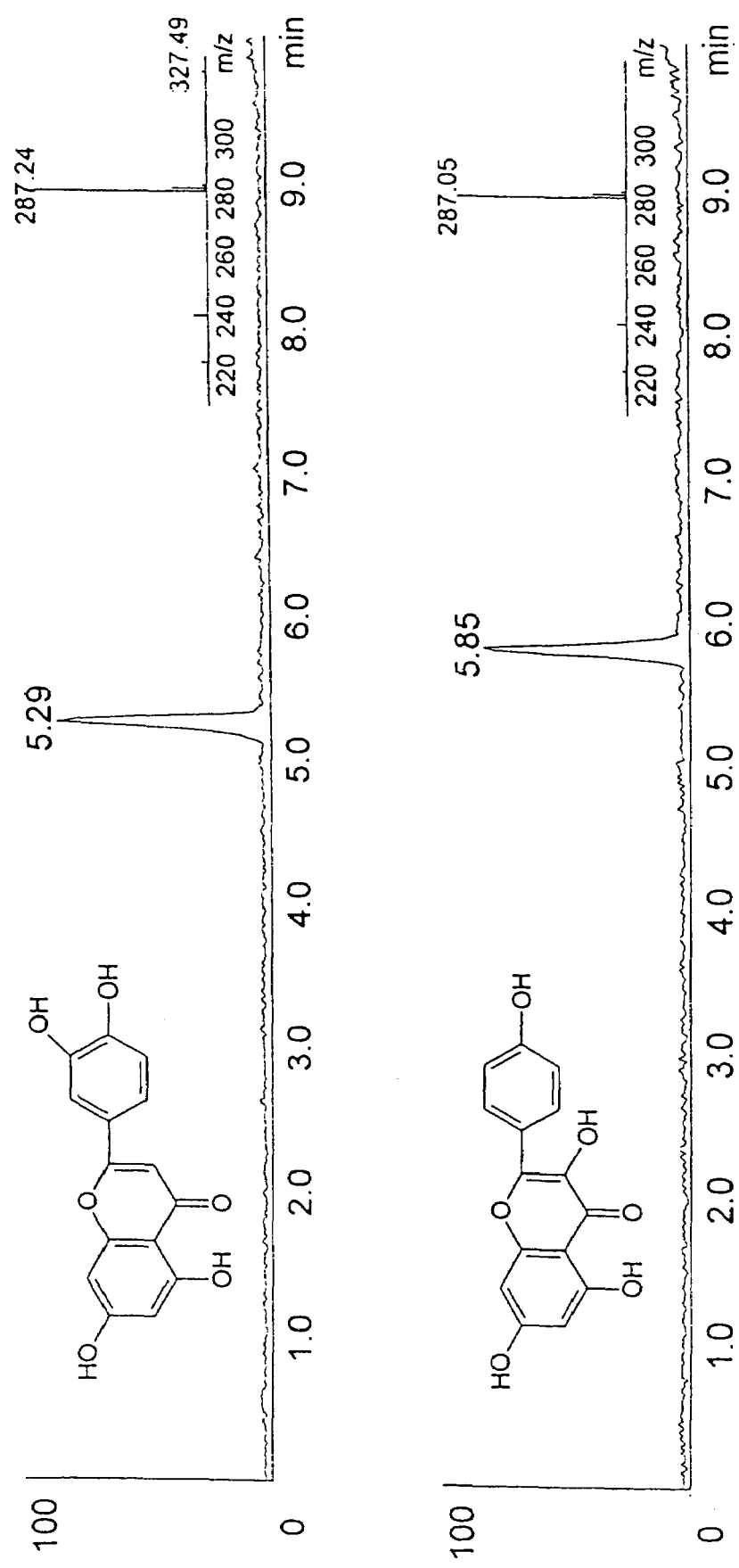
FIG. 10 illustrates spectra of molecular ions and chromatograms of elution conditions of two different isomeric chemical compounds.

FIG. 10 illustrates mass spectra of molecular ions and chromatogram of elution conditions for two different isomeric chemical compounds. As can be seen in FIG. 10, the liquid chromatogram is able to distinguish the two isomeric compounds depicted. The two isomers each have a molecular weight of about 286, and thus, the M+H peak in both chromatograms shows up at approximately 287. As is well known to persons skilled in the art, the mass spectrum can be used to determine not only molecular weight but the molecular formula of compounds. Thus, these chromatograms are useful for detecting replication of particular compounds within separate natural library libraries by comparing chromatographic and/or chemical properties.

Figure 11:
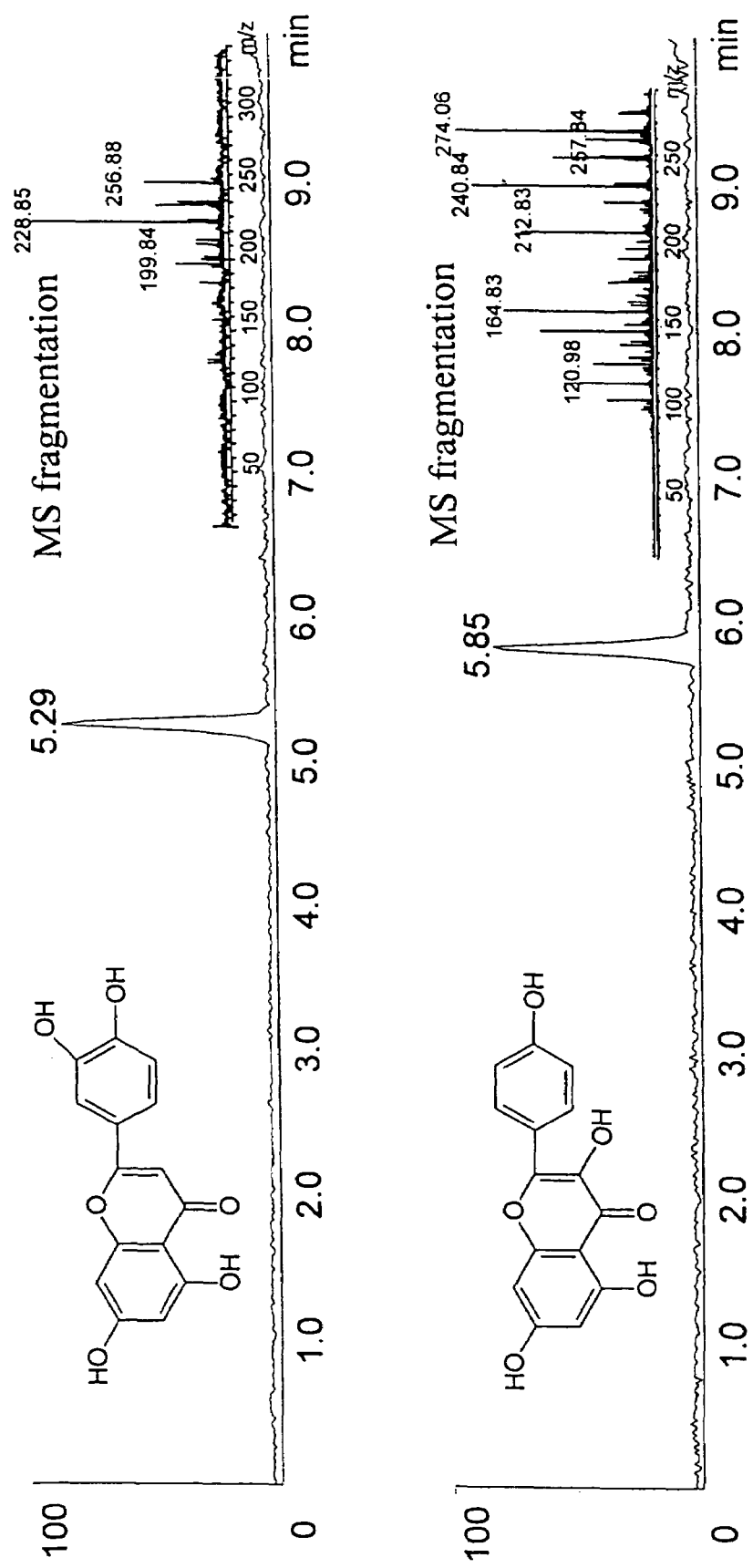
FIG. 11 illustrates chromatograms of elution conditions and MS/MS fragmentation patterns of two different isomeric chemical compounds.

FIG. 11 illustrates chromatograms of elution conditions and mass spectral fragmentation patterns of two different isomeric chemical compounds. Because the fragmentation patterns of different compounds are unique, this particular technique is useful in aiding in structural elucidation and identification of various compounds. As is known, and is further illustrated in FIG. 11, different isomeric compounds have different mass spectral fragmentation patterns. Thus, further evidence of the unique character of the two compounds is obtained and chromatographic and spectral characteristics for the individual compounds are known.

Figure 12:
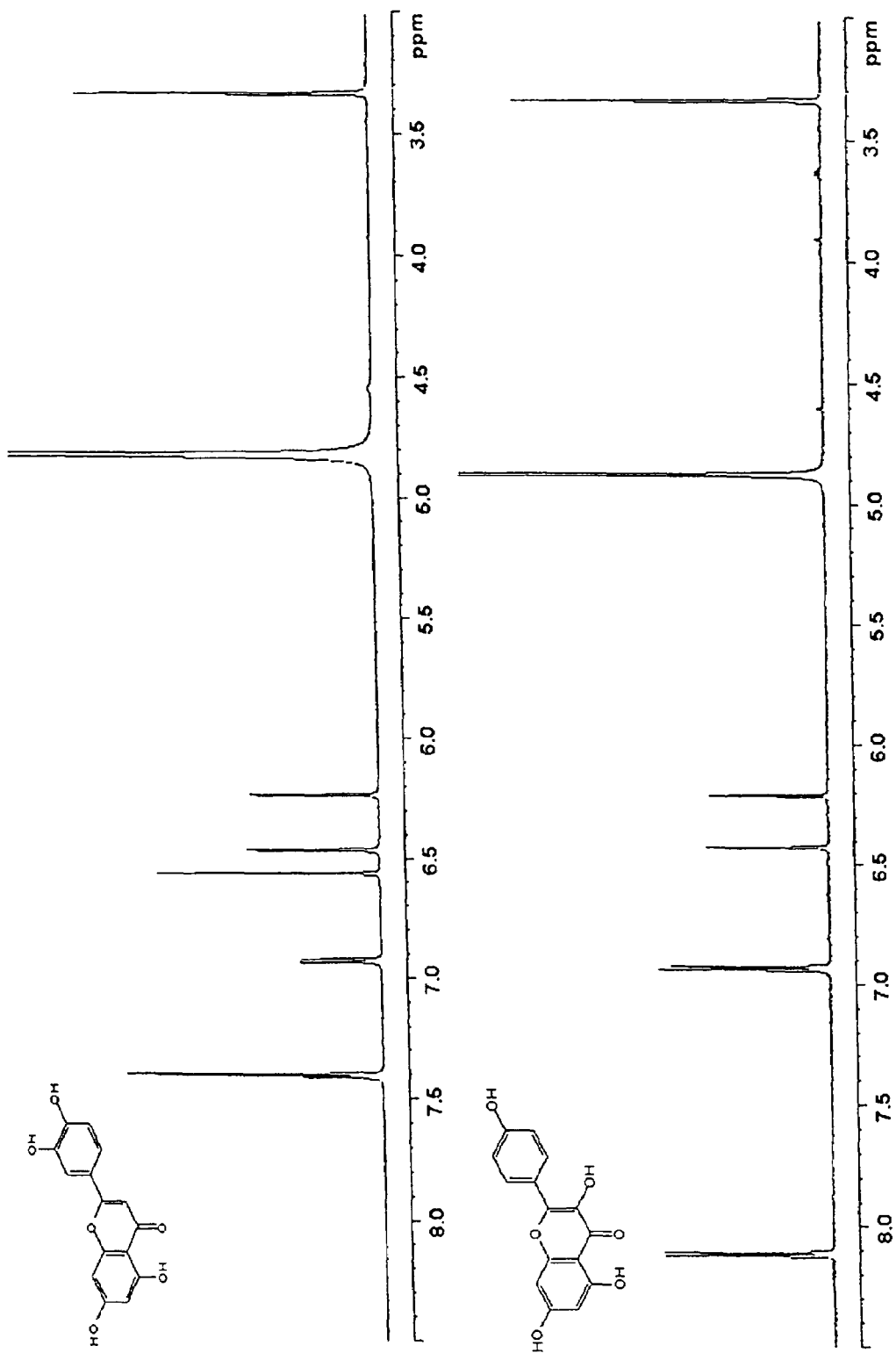
FIG. 12 is a 1D proton NMR spectrum of two different isomeric chemical compounds.

FIG. 12 illustrates a one-dimensional proton NMR spectra of the two different isomeric compounds. Again, the NMR spectra differ and are useful in further elucidating the structure of individual components derived from the same biological material.

FIG. 13 is a schematic representation of a data table that may be used to compare molecular ions and chromatographic elusion conditions for entire collections of chemical compounds derived from the same or different biological sources. The information contained within the data table shows the well from which particular files originate, the liquid chromatography mass spectral file name containing data, the number of components within any particular well, the retention time of individual components, the M+H data value for each of the individual components, and the relative abundance of each component within the particular well. As can be seen, there may be some overlap between individual wells which contain common compounds. In addition to the data depicted in FIG. 13, data can also be collected which describes or identifies overlapping biological sources, i.e. those compounds which appear in more than one biological source.

The examples set forth below further illustrate the process used to produce the invention and the chemical compound library according to the invention. The non-limiting paragraphs which follow the examples, describe and outline various aspects of the present invention.

EXAMPLE 1

Listed below are procedures that have been used with some variations as noted in U.S. Ser. No. 60/280,739 and PCT/US00/30195, to produce a chemical compound library from greater than two hundred plants.

Liquid Extraction Procedure

E1. Ethanol/Ethyl Acetate (50:50): Weigh the plant material. Appropriately grind the plant material to a fine powder. Transfer the ground plant material into a 4 L flask. Transfer 1 L of ethanol/ethyl acetate (50:50) solution to the 4 L flask. Agitate for approximately 18 to 22 hours. Pour the solution through a low ash filter paper and funnel into an appropriate round bottom evaporator flask. Reduce to approximately 20 ml of liquid at less than 40° C. Turn off heat. Repeat and combine with first extract. Reduce to dryness under vacuum. Weigh the dried extract. Combine with the Ethanol Extract (E1). Mix the extract thoroughly. Vials are store under nitrogen at −20° C.

E2. Methanol/Water (70:30): Return any insoluble material in the low ash filter paper and funnel to the original 4 L flask. Transfer 1 L of methanol/water (70:30) solution to the 4 L flask. Agitate for approximately 18 to 22 hours. Pour the solution through a low ash filter paper and funnel into an appropriate round bottom evaporator flask. Reduce to approximately 20 ml of liquid at less than 40° C. Turn off heat. Repeat and combine with first extract. Reduce to dryness under vacuum. Weigh the dried extract. Mix the extract thoroughly. Vials are store under nitrogen at −20° C.

Flash Chromatography Procedure

The Flash Chromatographic separations are performed on Flash Master 11 system, made by Jones Chromatography. The E1 extracts are separated by silica column and E2 extracts are separated by C-18 column. The gradients for Eland E2 are as following:

E1: 1. E1-F1-hexane/ethyl acetate (75/25) fraction
2. E1-F2-hexane/ethyl acetate (50/50) fraction
3. E1-F3-ethyl acetate fraction
4. E1-E4-ethyl acetate/methanol (75/25) fraction
5. E1-F5-ethyl acetate/methanol (50/50) fraction E2: 1. E2-F1-water fraction
2. E2-F2-methanol fraction Procedure for the Removal of Tetramers or Greater of Polyphenolics;

Method 1

1. Column Preparation. (Step 1)

Place a new IST 2.5 g polyamide column cartridge onto the "VacMaster Sample Processing Station" equipped with 20 ml borosilicate collection tubes. Elute the column with 10 ml methanol, then elute with 40 ml of water. Leave the column loaded with additional 20 ml water overnight to swell the resin.

2. Extract Detannification. (Step 2)

2.1 Sample Preparation.

Weight 1 g of the organic or aqueous extract into a labeled vial. Dissolve in 10 mL water (aqueous extract) or methanol (organic extract). Sonicate if necessary. Spin down any insoluble material in the Savant SpeedVac. 2.2 Sample Loading.

Outfit the "VacMaster Sample Processing Station" with clean, empty 20 mL borosilicate collection tubes.

After spinning the sample in the Savant, bring the liquid onto the column. Run the column until the liquid reaches the surface of the frit. Re-dissolve the insoluble material that settled in the Savant using additional water or methanol (aqueous extract) or methanol (organic extract). Bring the liquid onto the column. It may be necessary to sonicate again and if any insoluble material persists to spin the sample. Repeat this process until all extract has been brought onto the column.*

*Some insoluble material may be present in the samples resulting from the grinding and extraction methods. If repeated attempt to dissolve this fail, the material can brought onto the column using methanol. It will be filtered out during elution of the sample.

2.3 Sample Elution.

Rinse the column with 40 to 60 mL methanol. Collect into borosilicate tubes and combine all the eluent into a 1 L round bottom flask for drying. Rotavap the sample to 20 dryness. It is now ready for further processing using Flash Chromatography.

3. Flow Chart of the Process

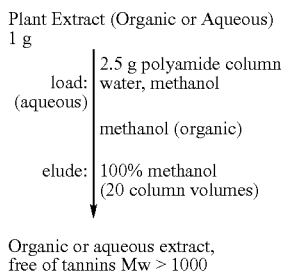

Procedure to Remove Compounds with Molecular Weights Greater than 3000 Daltons

1. Select the -sample for filtration through a Centricon Filter unit.
2. Weigh approximately 100 mg into a scintillation vial. Dissolve into 50 mL methanol. Transfer to outer unit of the Centricon Filter. Replace the inner part of the filter and the cap. Place the filter unit into a centrifuge and spin for 14 hours at 3000 g.
3. Poor out the contents of the inner unit into a clean tarred scintillation vial.
4. Dry the fraction overnight in the SpeedVac.

Parallel Preparative HPLC Procedure

1. Sample Preparation. 50 mg or the total amount of sample, whichever less, is injected.
2. Method
   1. 1000 pl of sample is injected.
   2. 30 minute linear gradients are used for elution. The exact gradient depends on the sample being process (see below). All gradients are followed by a 5 minute wash with 100% acetonitrile.
      a. E1F2: 60-100% water-acetonitrile
      b. E1F3: 30-70% water-acetonitrile
      c. E1F4: 5-40% water-acetonitrile
      d. E1F5 5-40% water-acetonitrile
      e. E2F2: 5-45% water-acetonitrile
   3. Flow rate is 20 ml/minute
   4. Fractions are collected every 1 minute for the 35 minutes of the run.
      a. 18×150 mm glass test tubes are used to collect the fractions
3. Materials and reagents
   1. Equipment
      b. Gilson 215/849 autosampler with 1000 gl injection loops
      c. Gilson 204 fraction collectors
      d. Beckman Coulter 126P pumps and 166 detectors
      e. Beckman Coulter
   2. Reagents
      a. Water and Acetonitrile HPLC grade
      b. Columns C-18 Betasil (Keystone), 20×100mm
      c. Solvents for sample re-suspension are be HPLC grade LC/ELSD/MS Procedure for Analysis of Fractions 1. LC-ELSD-MS Experimental Methods.
   a. HPLC Conditions Liquid flow is provided by a Waters 600 binary pump. The flow is split 8 ways by use of a low dead volume eight way splitter. The separate streams are directed to the Rheodyne injection valves of a Gilson 889 Liquid handler which is mounted on a Gilson 215 multiple injection autosampler. All samples are presented to this system in 96 well microtiter or deep well plates and an injection volume of 20 uL employed throughout. HPLC Separation is achieved on Betabasic C 18 columns (4.6×5 0 mm, 5 µM) obtained from Western Analytical. The gradient profile used for elution is outlined in Table 1.

TABLE 1

HPLC SOP gradient

| Time/min | % A (H$_2$O + 0.1 HCOOH) | % B (CH$_3$CN + 0.1% HCOOH) |
|---|---|---|
| 0 | 95 | 5 |
| 1 | 95 | 5 |
| 8.5 | 25 | 75 |
| 9.0 | 5 | 95 |
| 9.6 | 5 | 95 |
| 10.5 | 95 | 5 |
| 11.0 | 95 | 5 |

A flow rate of 9.6 ml/min is used providing a flow of 1.2 ml/min through each column. The eluent from each column is passed through a four way Valco low dead volume cross which splits the 1.2 ml/min flow into three separate streams of 0 1, 0.4 and 0.7 nil/min. For each column, the 0.1 ml/min stream is presented in a separate line to one inlet of the 8-way multiplexed electrospray source, the 0.4 n-fl/min to the inlet of the Alltech 500 ELSD detector and the 0.7 ml/min stream is routed to waste.

b. MS Analysis

All MS data is acquired on an LCT orthogonal TOF spectrometer (Micromass) fitted with an eight-way multiplexed electrospray interface (MUX). In this analysis each liquid stream is sampled for 0.1 sec. with mass spectra acquired from 200-1000 Da into eight simultaneously open data files synchronized with the spray being sampled. The time taken to move to the adjacent sampling position is 0.05 sec. This cycle produces a data point for each spray every 0.1 sec. The LCT and MUX are operated under MassLynx V3.4.

c. ELSD Analysis

ELSD detection was carried out using Alltech 500 units. For an inlet flow of 0.4 ml/min, the nebulizer gas flow for each unit was optimized between 2.95 and 3.25 SLPM. The drift tube temperature for each unit was similarly optimized between 95-105T for each stream.

2. Completion of Analysis

The plate report is placed in the completed plate section of the LC-ELSD-MS analysis log. The Plate is placed in the "completed plates" section of the plate refrigerator.

3. Data Collection and Organization a. Raw Data

Each plate or collection of plates is assigned a project name in the MassLynx software. The project name is either the name of the plate or the name of a series of plates combined, e.g.

Acqudb: LC-MS acquisition methods (time pages)

Curvedb: quantitation data

Datadb: Raw data (LC-MS and LC-ELSD data)

Methdb:

SampleDB: Sample lists.

b. Post Processing.

Each plate is further processed by entering the required OpenLynx method into the sample list. Result of this processing is to produce a *.rpt file for each sample list or plate. This *.rpt file is then processed to produce a list of masses and retention times. These masses are then entered into a second sample list for each plate and subject to a second OpenLynx method whose final result is also a *.rpt file from which is extracted the retention time, significant ion and ELSD data for each peak detected by LC-ELSD-MS. Data from this *.rpt file is then exported to form part of the final Excel report for each plate which has the following form:

one thousand micrograms of material. The quantity of material in each fraction is determined by evaporative light scattering from the LC/ELSD/MS analysis.

High-throughput Screening

A sufficient quantity of each fraction from the mother plate that contains chemical compounds is added to an individual well in an appropriate intermediate microtiter plate. Aliquots of the fractions are removed as needed from the intermediate microtiter plate and placed in an end-user biological assay microtiter plate in a normalized predetermined amount based on mass so as e.g. to achieve an initial screening concentration of 1 to 20 micromolar. Hundreds to thousands of fractions are screened in parallel for biological 5 activity using such plates as is known to a person of ordinary skill.

EXAMPLE 2

A single plant sample, the leaves and stems of *Baptisia alba*, was fractionated to produce a library according to the invention. Table 1 contains the weights of the extracts and fractions of the drug-like and non-drug-like compounds of *Baptisia alba*.

TABLE 1

Approximate Weights of Extracts and Fractions of the Leaves and Stems of *Baptisia alba* prior to Parallel Preparative HPLC.

| Sample | Weight (grams) |
|---|---|
| Extract 1 | 4.1 |
| Extract 2 | 7.1 |
| E1-F2 | 0.045 |
| E1-F3 | 0.035 |
| E1-F4 | 0.216 |
| E1-F5 | 0.104 |
| E2-F2 | 0.039 |
| Discarded compounds from 1.0 gram of Extract 1 with log Ps greater than 6 or less than −1, Tetramers or greater of Polyphenolics, and molecular weights greater than 3000 Daltons | 0.628 |
| Discarded compounds from 2.0 grams of Extract 2 with log Ps greater than 6 or less than −1, Tetramers or greater of Polyphenolics, and molecular weights greater than 3000 Daltons | 1.966 |

Because approximately 87% of the extracts of the leaves and stems of *Baptisia alba* consisted of discarded non-drug-like compounds, testing crude extracts or pre-fractionated of the leaves and stems of *Baptisia alba* would have resulted in screening approximately 99% or 80%, respectively, of the drug-like compounds below optimal screening concentrations. (One of the unexpected advantages of the inventive method is that the same physico-chemical characteristics

| Compound# | Well# | File name | No of components | Rt | Molecular ion + significant ions | ELSD Peak area | Dereplication hits |
|---|---|---|---|---|---|---|---|
| | | | | | | | |

Storage of Chromatographic Fractions of Chemical Compounds

Chromatographic fractions of chemical compounds consist of less than one microgram of material to greater than used for fractionation also eliminate non-drug-like compounds, typically those with log Ps greater than 6 or less than −1, tetramers or greater of polyphenolics, and molecular weights greater than 3000 5 Daltons.)

Table 2 contains the molecular ions, evaporative light scattering areas, retention times, and calculated weights of the chemical compounds in the wells of the microtiter plates analyzed by HPLC/MS/ELSD. Table 2 contains greater than 200 distinct chemical compounds from the leaves and stems of *Baptisia alba*. Because the library was produced according to the invention, all of these chemical compounds may be tested at optimal screening concentrations. Information is automatically extracted from the raw data of chromatograms and placed into a database.

In Table 2:

MS RT: Retention time using Mass spectral detector

M+H ion: Molecular weight of M+H ion

ELSD PKS: Peaks detected by evaporative light scattering detector

ELSD RT: Retention time using evaporative light scattering detector

ELSD area: Relative area of peaks from evaporative light scattering detector

Weight ELSD: Calculated weights of peaks

Table 2 shows data obtained from the wells of the intermediate plate prepared from the mother plate. The filename identifies the plate number and position. Table 2 presents data for the library of compounds from one plant, in about 125 wells, on about 6 different intermediate plates.

There are about 500 lines of data, reflecting about 200 compounds. The MS data and the ELSD data are obtained for each well, and are somewhat independent of each other. The ELSD is used as the universal detector for normalization purposes. For the first well, CP0280 well 2, there is an ELSD weight of 47 (micrograms), indicating at least one compound is present. However, in this well the compound apparently did not ionize in the standard conditions being used, and gave no MS or M+H ion data. For well 3, there is at least one compound having an ELSD weight of 41, and MS shows three different compounds with MW in the range of about 300 to 900 daltons. Well 6 shows one MS peak, but four ELSD peaks. In well 10, the MS data for three peaks is shown, but the ELSD weight is shown as zero, meaning the mass is below the calibrated threshold, and so this well would be considered a blank.

To prepare a final plate for high throughput screening, a normalized mass of material is removed from the intermediate plate. For example, from CP0280 well 6, 10 micrograms of material out of the total of about 1900 micrograms is loaded on a well of the final plate for one particular end user (who may run the material through several assays). Another plate may be prepared with 20 micrograms for each well. Wells from the intermediate plates which do not have enough mass are not loaded on the final assay plates.

TABLE 2

HPLC/MS/ELSD Data on the Chromatographic Fractions of the Leaves and Stems of Baptisia alba according to the Invention.

| FILENAME | MS RT | M + H Ion | ELSD RT | ELSD Area | Weight ELSD |
| --- | --- | --- | --- | --- | --- |
| CP0280-pos-well 2 | 0.0 | 0.00 | | | |
| CP0280-pos-well 2 | | | 10.3 | 2552 | 47 |
| CP0280-pos-well 3 | 2.5 | 286.99 | | | |
| CP0280-pos-well 3 | 7.7 | 904.40 | | | |
| CP0280-pos-well 3 | 8.3 | 903.39 | | | |
| CP0280-pos-well 3 | | | 2.6 | 8469 | 41 |
| CP0280-pos-well 4 | 3.6 | 285.00 | | | |
| CP0280-pos-well 4 | 5.5 | 277.15 | | | |
| CP0280-pos-well 4 | 8.1 | 297.20 | | | |
| CP0280-pos-well 4 | 8.6 | 903.34 | | | |
| CP0280-pos-well 4 | | | 3.3 | 67530 | 144 |
| CP0280-pos-well 4 | | | 3.6 | 75988 | 155 |
| CP0280-pos-well 5 | 3.7 | 409.07 | | | |
| CP0280-pos-well 5 | 8.3 | 889.37 | | | |
| CP0280-pos-well 5 | | | 3.9 | 6057 | 43 |
| CP0280-pos-well 5 | | | 8.1 | 43056 | 134 |
| CP0280-pos-well 5 | | | 8.4 | 28297 | 106 |
| CP0280-pos-well 5 | | | 8.8 | 46210 | 139 |
| CP0280-pos-well 6 | 0.0 | 0.00 | | | |
| CP0280-pos-well 6 | | | 4.4 | 1056 | 18 |
| CP0280-pos-well 6 | | | 4.5 | 1210 | 20 |
| CP0280-pos-well 6 | | | 6.9 | 1500 | 24 |
| CP0280-pos-well 6 | | | 8.5 | 352791 | 1824 |
| CP0280-pos-well 7 | 8.0 | 901.36 | | | |
| CP0280-pos-well 7 | | | 8.8 | 638395 | 302 |
| CP0280-pos-well 8 | 0.0 | 0.00 | | | |
| CP0280-pos-well 8 | | | 9.8 | 843586 | 792 |
| CP0280-pos-well 8 | | | 10.6 | 15345 | 64 |
| CP0280-pos-well 8 | | | 10.8 | 2720 | 3 |
| CP0280-pos-well 10 | 7.3 | 411.25 | | | |
| CP0280-pos-well 10 | 8.2 | 887.32 | | | |
| CP0280-pos-well 10 | 8.4 | 887.32 | | | |
| CP0280-pos-well 10 | | | 0.0 | 0 | |
| CP0280-pos-well 11 | 7.2 | 599.19 | | | |
| CP0280-pos-well 11 | 8.2 | 887.42 | | | |
| CP0280-pos-well 11 | | | 0.0 | 0 | |
| CP0280-pos-well 12 | 7.3 | 887.52 | | | |
| CP0280-pos-well 12 | 8.3 | 889.32 | | | |
| CP0280-pos-well 12 | | | 9.4 | 1838 | 17 |
| CP0280-pos-well 13 | 7.9 | 381.29 | | | |
| CP0280-pos-well 13 | 8.4 | 871.34 | | | |
| CP0280-pos-well 13 | | | 6.7 | 4096 | 34 |

TABLE 2-continued

HPLC/MS/ELSD Data on the Chromatographic Fractions of the
Leaves and Stems of Baptisia alba according to the Invention.

| FILENAME | MS RT | M + H Ion | ELSD RT | ELSD Area | Weight ELSD |
|---|---|---|---|---|---|
| CP0280-pos-well 13 | | | 9.1 | 5968 | 43 |
| CP0280-pos-well 14 | 0.0 | 0.00 | | | |
| CP0280-pos-well 14 | | | 8.8 | 8046 | 110 |
| CP0280-pos-well 16 | 0.0 | 0.00 | | | |
| CP0280-pos-well 16 | | | 9.8 | 1916 | −3 |
| CP0280-pos-well 16 | | | 9.8 | 1115 | −10 |
| CP0280-pos-well 17 | 7.6 | 683.35 | | | |
| CP0280-pos-well 17 | | | 7.4 | 414816 | 277 |
| CP0280-pos-well 18 | 7.5 | 427.14 | | | |
| CP0280-pos-well 18 | 7.6 | 799.38 | | | |
| CP0280-pos-well 18 | | | 0.0 | 0 | |
| CP0280-pos-well 19 | 7.7 | 554.36 | | | |
| CP0280-pos-well 19 | 7.7 | 263.18 | | | |
| CP0280-pos-well 19 | 8.5 | 871.34 | | | |
| CP0280-pos-well 19 | 10.8 | 871.29 | | | |
| CP0280-pos-well 19 | | | 0.0 | 0 | |
| CP0280-pos-well 20 | 7.8 | 566.23 | | | |
| CP0280-pos-well 20 | 8.1 | 609.16 | | | |
| CP0280-pos-well 20 | 8.2 | 871.34 | | | |
| CP0280-pos-well 20 | 8.6 | 887.32 | | | |
| CP0280-pos-well 20 | 10.5 | 887.32 | | | |
| CP0280-pos-well 20 | | | 0.0 | 0 | |
| CP0280-pos-well 21 | 7.8 | 609.12 | | | |
| CP0280-pos-well 21 | 8.0 | 887.32 | | | |
| CP0280-pos-well 21 | 8.5 | 887.32 | | | |
| CP028b-pos-well 21 | | | 7.7 | 1078 | 17 |
| CP0280-pos-well 21 | | | 7.9 | 214442 | 320 |
| CP0280-pos-well 22 | 8.2 | 593.15 | | | |
| CP0280-pos-well 22 | | | 9.4 | 11919 | 155 |
| CP0280-pos-well 23 | 8.2 | 871.34 | | | |
| CP0280-pos-well 23 | | | 8.6 | 17910 | 26 |
| CP0280-pos-well 23 | | | 10.2 | 2121 | 14 |
| CP0280-pos-well 24 | 0.0 | 0.00 | | | |
| CP0280-pos-well 24 | | | 10.5 | 6622 | 27 |
| CP0280-pos-well 25 | 8.6 | 887.32 | | | |
| CP0280-pos-well 25 | | | 9.3 | 283863 | 216 |
| CP0280-pos-well 26 | 8.0 | 887.27 | | | |
| CP0280-pos-well 26 | 8.2 | 871.34 | | | |
| CP0280-pos-well 26 | 8.5 | 871.34 | | | |
| CP0280-pos-well 26 | | | 6.4 | 1087 | 39 |
| CP0280-pos-well 26 | | | 8.9 | 1350 | 41 |
| CP0280-pos-well 26 | | | 8.9 | 4990 | 54 |
| CP0280-pos-well 26 | | | 9.4 | 1255 | 40 |
| CP0280-pos-well 26 | | | 9.7 | 14074 | 71 |
| CP0280-pos-well 26 | | | 9.9 | 17711 | 76 |
| CP0280-pos-well 27 | 8.3 | 871.29 | | | |
| CP0280-pos-well 27 | | | 8.8 | 2867 | 25 |
| CP0280-pos-well 27 | | | 8.9 | 4912 | 31 |
| CP0280-pos-well 28 | 7.7 | 887.42 | | | |
| CP0280-pos-well 28 | 8.3 | 887.27 | | | |
| CP0280-pos-well 28 | 8.4 | 887.27 | | | |
| CP0280-pos-well 28 | | | 8.9 | 20461 | 65 |
| CP0280-pos-well 28 | | | 9.0 | 10197 | 41 |
| CP0280-pos-well 28 | | | 9.1 | 16919 | 57 |
| CP0280-pos-well 28 | | | 9.3 | 10653 | 42 |
| CP0280-pos-well 28 | | | 10.2 | 10535 | 42 |
| CP0280-pos-well 28 | | | 10.4 | 12477 | 47 |
| CP0280-pos-well 29 | 7.9 | 537.25 | | | |
| CP0280-pos-well 29 | 8.4 | 871.34 | | | |
| CP0280-pos-well 29 | 9.8 | 567.27 | | | |
| CP0280-pos-well 29 | | | 9.8 | 26171 | 101 |
| CP0280-pos-well 30 | 0.0 | 0.00 | | | |
| CP0280-pos-well 30 | | | 9.4 | 3657 | 54 |
| CP0280-pos-well 30 | | | 9.7 | 100841 | 815 |
| CP0280-pos-well 30 | | | 10.1 | 4013 | 59 |
| CP0280-pos-well 31 | 0.0 | 0.00 | | | |
| CP0280-pos-well 31 | | | 10.3 | 2605 | 15 |
| CP0280-pos-well 32 | 0.0 | 0.00 | | | |
| CP0280-pos-well 32 | | | 9.8 | 1651 | −5 |
| CP0280-pos-well 32 | | | 10.2 | 61537 | 177 |
| CP0280-pos-well 32 | | | 10.5 | 20734 | 82 |
| CP0280-pos-well 33 | 0.0 | 0.00 | | | |
| CP0280-pos-well 33 | | | 9.4 | 1144 | 14 |
| CP0280-pos-well 33 | | | 10.6 | 4051 | 18 |

TABLE 2-continued

HPLC/MS/ELSD Data on the Chromatographic Fractions of the
Leaves and Stems of Baptisia alba according to the Invention.

| FILENAME | MS RT | M + H Ion | ELSD RT | ELSD Area | Weight ELSD |
|---|---|---|---|---|---|
| CP0280-pos-well 33 | | | 10.6 | 1445 | 15 |
| CP0280-pos-well 34 | 8.1 | 871.34 | | | |
| CP0280-pos-well 34 | 8.2 | 871.34 | | | |
| CP0280-pos-well 34 | 8.3 | 871.34 | | | |
| CP0280-pos-well 34 | 8.4 | 871.29 | | | |
| CP0280-pos-well 34 | | | 10.8 | 2058 | 45 |
| CP0280-pos-well 36 | 8.2 | 871.34 | | | |
| CP0280-pos-well 36 | 8.5 | 871.34 | | | |
| CP0280-pos-well 36 | | | 9.3 | 1758 | 17 |
| CP0280-pos-well 36 | | | 9.4 | 1121 | 15 |
| CP0280-pos-well 36 | | | 9.7 | 1182 | 15 |
| CP0280-pos-well 37 | 8.0 | 1158.98 | | | |
| CP0280-pos-well 37 | 8.7 | 901.36 | | | |
| CP0280-pos-well 37 | 10.4 | 901.31 | | | |
| CP0280-pos-well 37 | | | 0.0 | 0 | |
| CP0280-pos-well 38 | 0.0 | 0.00 | | | |
| CP0280-pos-well 38 | | | 8.3 | 3221 | 48 |
| CP0280-pos-well 38 | | | 8.5 | 1586 | 26 |
| CP0280-pos-well 39 | 7.9 | 871.34 | | | |
| CP0280-pos-well 39 | 8.2 | 901.36 | | | |
| CP0280-pos-well 39 | 8.7 | 901.31 | | | |
| CP0280-pos-well 39 | | | 10.4 | 5352 | 17 |
| CP0280-pos-well 40 | 0.0 | 0.00 | | | |
| CP0280-pos-well 40 | | | 8.7 | 3366 | 8 |
| CP0280-pos-well 40 | | | 9.3 | 15515 | 65 |
| CP0280-pos-well 40 | | | 9.5 | 2419 | 1 |
| CP0280-pos-well 40 | | | 9.7 | 7411 | 31 |
| CP0280-pos-well 40 | | | 9.9 | 2738 | 3 |
| CP0280-pos-well 40 | | | 10.1 | 2915 | 5 |
| S390E 1 F3-pos-061501-well6 | 0.0 | 0.00 | | | |
| S390E 1 F3-pos-061501-well6 | | | 5.9 | 1647 | 35 |
| S39OE1 F3-pos-061501-weII7 | 0.0 | 0.00 | | | |
| S39OE1 F3-pos-061501-weII7 | | | 6.0 | 176993 | 250 |
| S390E 1 F3-pos-061501-well8 | 0.0 | 0.00 | | | |
| S390E 1 F3-pos-061501-well8 | | | 5.7 | 5585 | 29 |
| S390E 1 F3-pos-061501-well8 | | | 5.8 | 18067 | 98 |
| S390E 1 F3-pos-061501-well20 | 8.0 | 437.28 | | | |
| S39OE1 F3-pos-061501-well20 | | | 0.0 | 0 | |
| S390E 1 F3-pos-061501-well22 | 8.1 | 705.59 | | | |
| S390E1 F3-pos-061501-weII22 | 8.3 | 553.48 | | | |
| S390E1 F3-pos-061501-weII22 | | | 8.2 | 3589 | 71 |
| S390E1 F3-pos-061501-weII22 | | | 8.3 | 1545 | 33 |
| S390E 1 F3-pos-061501-well23 | 0.0 | 0.00 | | | |
| S390E 1 F3-pos-061501-we[23 | | | 8.4 | 7938 | 145 |
| S390E 1 F3-pos-061501-well23 | | | 8.6 | 139135 | 228 |
| S390E 1 F3-pos-061501-well23 | | | 9.1 | 13241 | 149 |
| S390E 1 F3-pos-061501-well25 | 0.0 | 0.00 | | | |
| S390E 1 F3-pos-061501-well25 | | | 9.3 | 3760 | 23 |
| S390E 1 F3-pos-061501-well27 | 9.0 | 557.51 | | | |
| S390E 1 F3-pos-061501-well27 | | | 9.0 | 2536 | 32 |
| CP0084-pos-071401-well 42 | 9.2 | 297.27 | | | |
| CP0084-pos-071401-well 42 | | | 0.0 | 0 | |
| CP0084-pos-071401-well 44 | 3.9 | 611.12 | | | |
| CP0084-pos-071401-well 44 | 4.0 | 465.06 | | | |
| CP0084-pos-071401-well 44 | 4.3 | 449.08 | | | |
| CP0084-pos-071401-well 44 | 4.6 | 609.14 | | | |
| CP0084-pos-071401-well 44 | 4.7 | 609.14 | | | |
| CP0084-pos-071401-well 44 | 4.8 | 609.14 | | | |

TABLE 2-continued

HPLC/MS/ELSD Data on the Chromatographic Fractions of the
Leaves and Stems of Baptisia alba according to the Invention.

| FILENAME | MS RT | M + H Ion | ELSD RT | ELSD Area | Weight ELSD |
|---|---|---|---|---|---|
| CP0084-pos-071401-well 44 | | | 3.2 | 31400 | 87 |
| CP0084-pos-071401-well 44 | | | 3.4 | 27533 | 79 |
| CP0084-pos-071401-well 44 | | | 3.7 | 97219 | 182 |
| CP0084-pos-071401-well 44 | | | 3.8 | 258754 | 331 |
| CP0084-pos-071401-well 44 | | | 4.0 | 381435 | 415 |
| CP0084-pos-071401-well 44 | | | 4.3 | 255354 | 328 |
| CP0084-pos-071401-well 44 | | | 4.6 | 360258 | 401 |
| CP0084-pos-071401-well 45 | 4.0 | 449.08 | | | |
| CP0084-pos-071401-well 45 | 4.6 | 609.14 | | | |
| CP0084-pos-071401-well 45 | 6.0 | 284.06 | | | |
| CP0084-pos-071401-well 45 | | | 3.7 | 39613 | 128 |
| CP0084-pos-071401-well 45 | | | 3.8 | 84079 | 194 |
| CP0084-pos-071401-well 45 | | | 3.9 | 22269 | 92 |
| CP0084-pos-071401-well 45 | | | 4.0 | 89048 | 200 |
| CP0084-pos-071401-well 45 | | | 4.6 | 12875 | 67 |
| CP0084-pos-071401-well 46 | 4.4 | 465.06 | | | |
| CP0084-pos-071401-well 46 | 4.7 | 449.08 | | | |
| CP0084-pos-071401-well 46 | 5.3 | 609.14 | | | |
| CP0084-pos-071401-well 46 | 6.4 | 505.11 | | | |
| CP0084-pos-071401-well 46 | | | 4.5 | 309388 | 1684 |
| CP0084-pos-071401-well 46 | | | 4.8 | 214596 | 1341 |
| CP0084-pos-071401-well 46 | | | 5.2 | 188751 | 1236 |
| CP0084-pos-071401-well 46 | | | 6.6 | 1372 | 23 |
| CP0084-pos-071401-well 47 | 4.6 | 449.08 | | | |
| CP0084-pos-071401-well 47 | 5.2 | 609.14 | | | |
| CP0084-pos-071401-well 47 | 7.4 | 315.06 | | | |
| CP0084-pos-071401-well 47 | | | 4.3 | 65914 | 138 |
| CP0084-pos-071401-well 47 | | | 4.5 | 3500 | 106 |
| CP0084-pos-071401-well 47 | | | 4.8 | 401700 | 272 |
| CP0084-pos-071401-well 47 | | | 5.3 | 358997 | 257 |
| CP0084-pos-071401-well 48 | 0.0 | 0.00 | | | |
| CP0084-pos-071401-well 48 | | | 3.6 | 53484 | 161 |
| CP0084-pos-071401-well 48 | | | 3.8 | 101001 | 240 |
| CP0084-pos-071401-well 48 | | | 4.1 | 8331 | 36 |
| CP0084-pos-071401-well 48 | | | 4.2 | 8163 | 35 |
| CP0084-pos-071401-well 48 | | | 4.3 | 97080 | 235 |
| CP0084-pos-071401-well 48 | | | 4.4 | 7306 | 31 |
| CP0084-pos-071401-well 49 | 4.6 | 609.14 | | | |
| CP0084-pos-071401-well 49 | 6.4 | 301.06 | | | |
| CP0084-pos-071401-well 49 | | | 4.2 | 63588 | 75 |
| CP0084-pos-071401-well 49 | | | 4.3 | 171295 | 152 |
| CP0084-pos-071401-well 49 | | | 4.6 | 135488 | 129 |
| CP0084-pos-071401-well 49 | | | 4.7 | 239959 | 192 |
| CP0084-pos-071401-well 49 | | | 4.8 | 446792 | 291 |
| CP0084-pos-071401-well 50 | 4.3 | 449.08 | | | |
| CP0084-pos-071401-well 50 | 4.6 | 609.14 | | | |
| CP0084-pos-071401-well 50 | 6.4 | 301.06 | | | |
| CP0084-pos-071401-well 50 | 6.9 | 315.06 | | | |
| CP0084-pos-071401-well 50 | 9.2 | 297.27 | | | |
| CP0084-pos-071401-well 50 | | | 4.2 | 2769 | 47 |
| CP0084-pos-071401-well 50 | | | 4.3 | 182613 | 174 |
| CP0084-pos-071401-well 50 | | | 4.7 | 347900 | 229 |
| CP0084-pos-071401-well 50 | | | 4.8 | 438416 | 253 |
| CP0084-pos-071401-well 50 | | | 6.4 | 2520 | 47 |
| CP0084-pos-071401-well 51 | 4.7 | 639.15 | | | |
| CP0084-pos-071401-well 51 | 4.8 | 609.14 | | | |
| CP0084-pos-071401-well 51 | 5.1 | 609.14 | | | |
| CP0084-pos-071401-well 51 | 6.6 | 301.06 | | | |
| CP0084-pos-071401-well 51 | 7.2 | 315.06 | | | |
| CP0084-pos-071401-well 51 | | | 4.4 | 7673 | 39 |
| CP0084-pos-071401-well 51 | | | 4.5 | 3917 | 28 |
| CP0084-pos-071401-well 51 | | | 4.6 | 4726 | 30 |
| CP0084-pos-071401-well 51 | | | 4.9 | 1100704 | 810 |
| CP0084-pos-071401-well 52 | 4.5 | 609.14 | | | |
| CP0084-pos-071401-well 52 | 4.9 | 609.14 | | | |
| CP0084-pos-071401-well 52 | 5.0 | 609.14 | | | |
| CP0084-pos-071401-well 52 | 6.3 | 301.06 | | | |
| CP0084-pos-071401-well 52 | 6.9 | 315.06 | | | |
| CP0084-pos-071401-well 52 | | | 4.1 | 15611 | 54 |
| CP0084-pos-071401-well 52 | | | 4.3 | 18267 | 60 |
| CP0084-pos-071401-well 52 | | | 4.5 | 1123962 | 760 |
| CP0084-pos-071401-well 52 | | | 5.3 | 9109 | 38 |
| CP0084-pos-071401-well 52 | | | 6.3 | 7879 | 35 |
| CP0084-pos-071401-well 53 | 4.3 | 609.14 | | | |

TABLE 2-continued

HPLC/MS/ELSD Data on the Chromatographic Fractions of the
Leaves and Stems of Baptisia alba according to the Invention.

| FILENAME | MS RT | M + H Ion | ELSD RT | ELSD Area | Weight ELSD |
|---|---|---|---|---|---|
| CP0084-pos-071401-well 53 | 4.5 | 609.14 | | | |
| CP0084-pos-071401-well 53 | 4.7 | 609.14 | | | |
| CP0084-pos-071401-well 53 | 5.9 | 301.06 | | | |
| CP0084-pos-071401-well 53 | 6.5 | 315.06 | | | |
| CP0084-pos-071401-well 53 | | | 3.7 | 1107 | 17 |
| CP0084-pos-071401-well 53 | | | 3.9 | 5572 | 41 |
| CP0084-pos-071401-well 53 | | | 4.1 | 9365 | 56 |
| CP0084-pos-071401-well 53 | | | 4.4 | 743714 | 611 |
| CP0084-pos-071401-well 53 | | | 4.7 | 166860 | 280 |
| CP0084-pos-071401-well 54 | 5.2 | 609.14 | | | |
| CP0084-pos-071401-well 54 | 5.3 | 609.14 | | | |
| CP0084-pos-071401-well 54 | 5.7 | 463.08 | | | |
| CP0084-pos-071401-well 54 | 6.8 | 301.06 | | | |
| CP0084-pos-071401-well 54 | | | 5.1 | 3860 | 57 |
| CP0084-pos-071401-well 54 | | | 5.4 | 54396 | 525 |
| CP0084-pos-071401-well 54 | | | 5.8 | 5941 | 84 |
| CP0084-pos-071401-well 55 | 5.4 | 593.14 | | | |
| CP0084-pos-071401-well 55 | 5.8 | 463.08 | | | |
| CP0084-pos-071401-well 55 | | | 5.5 | 303221 | 237 |
| CP0084-pos-071401-well 55 | | | 5.9 | 88108 | 148 |
| CP0084-pos-071401-well 56 | 0.0 | 0.00 | | | |
| CP0084-pos-071401-well 56 | | | 4.8 | 13550 | 58 |
| CP0084-pos-071401-well 57 | 5.3 | 463.08 | | | |
| CP0084-pos-071401-well 57 | | | 5.4 | 7767 | 22 |
| CP0084-pos-071401-well 58 | 5.4 | 427.23 | | | |
| CP0084-pos-071401-well 58 | 9.2 | 297.27 | | | |
| CP0084-pos-071401-well 58 | | | 0.0 | 0 | |
| CP0084-pos-071401-well 60 | 8.9 | 323.31 | | | |
| CP0084-pos-071401-well 60 | | | 0.0 | 0 | |
| CP0084-pos-071401-well 66 | 9.4 | 297.27 | | | |
| CP0084-pos-071401-well 66 | | | 0.0 | 0 | |
| CP0084-pos-071401-well 68 | 9.2 | 297.27 | | | |
| CP0084-pos-071401-well 68 | | | 0.0 | 0 | |
| CP0084-pos-071401-well 76 | 8.5 | 537.27 | | | |
| CP0084-pos-071401-well 76 | 9.3 | 297.27 | | | |
| CP0084-pos-071401-well 76 | | | 8.5 | 7987 | 35 |
| CP0084-pos-071401-well 77 | 7.9 | 537.27 | | | |
| CP0084-pos-071401-well 77 | 8.1 | 515.28 | | | |
| CP0084-pos-071401-well 77 | 8.7 | 539.29 | | | |
| CP0084-pos-071401-well 77 | 9.0 | 449.25 | | | |
| CP0084-pos-071401-well 77 | | | 8.0 | 1615 | 20 |
| CP0084-pos-071401-well 77 | | | 8.1 | 36550 | 122 |
| CP0084-pos-071401-well 77 | | | 8.8 | 5194 | 39 |
| CP0084-pos-071401-well 80 | 8.9 | 595.34 | | | |
| CP0084-pos-071401-well 80 | 9.1 | 507.26 | | | |
| CP0084-pos-071401-well 80 | | | 0.0 | 0 | |
| CP0074-pos-071301-well 44 | 2.3 | 1316.59 | | | |
| CP0074-pos-071301-well 44 | 9.0 | 323.28 | | | |
| CP0074-pos-071301-well 44 | | | 2.3 | 5063 | 27 |
| CP0074-pos-071301-well 44 | | | 2.8 | 15384 | 54 |
| CP0074-pos-071301-well 44 | | | 3.0 | 18253 | 60 |
| CP0074-pos-071301-well 44 | | | 3.2 | 89786 | 173 |
| CP0074-pos-071301-well 44 | | | 3.5 | 42091 | 105 |
| CP0074-pos-071301-well 45 | 6.0 | 284.06 | | | |
| CP0074-pos-071301-well 45 | | | 3.2 | 1624 | 20 |
| CP0074-pos-071301-well 46 | 2.9 | 219.11 | | | |
| CP0074-pos-071301-well 46 | 4.0 | 218.10 | | | |
| CP0074-pos-071301-well 46 | 54 | 407.17 | | | |
| CP0074-pos-071301-well 46 | 6.1 | 217.08 | | | |
| CP0074-pos-071301-well 46 | 6.8 | 284.06 | | | |
| CP0074-pos-071301-well 46 | | | 1.1 | 19258 | 232 |
| CP0074-pos-071301-well 46 | | | 4.5 | 3175 | 47 |
| CP0074-pos-071301-well 46 | | | 5.4 | 3414 | 51 |
| CP0074-pos-071301-well 46 | | | 5.6 | 1261 | 21 |
| CP0074-pos-071301-well 46 | | | 6.9 | 10297 | 136 |
| CP0074-pos-071301-well 49 | 4.3 | 449.08 | | | |
| CP0074-pos-071301-well 49 | 6.1 | 505.11 | | | |
| CP0074-pos-071301-well 49 | | | 4.1 | 25263 | 40 |
| CP0074-pos-071301-well 49 | | | 4.4 | 63256 | 75 |
| CP0074-pos-071301-well 49 | | | 5.4 | 8915 | 23 |
| CP0074-pos-071301-well 49 | | | 5.5 | 5862 | 20 |
| CP0074-pos-071301-well 49 | | | 5.9 | 14723 | 29 |
| CP0074-pos-071301-well 49 | | | 6.1 | 29956 | 45 |
| CP0074-pos-071301-well 50 | 4.6 | 449.08 | | | |

TABLE 2-continued

HPLC/MS/ELSD Data on the Chromatographic Fractions of the
Leaves and Stems of Baptisia alba according to the Invention.

| FILENAME | MS RT | M + H Ion | ELSD RT | ELSD Area | Weight ELSD |
|---|---|---|---|---|---|
| CP0074-pos-071301-well 50 | 5.2 | 609.14 | | | |
| CP0074-pos-071301-well 50 | 5.7 | 463.08 | | | |
| CP0074-pos-071301-well 50 | | | 4.4 | 1559 | 42 |
| CP0074-pos-071301-well 50 | | | 4.6 | 22816 | 82 |
| CP0074-pos-071301-well 50 | | | 5.3 | 3572 | 50 |
| CP0074-pos-071301-well 50 | | | 5.7 | 41999 | 100 |
| CP0074-pos-071301-well 51 | 4.7 | 449.08 | | | |
| CP0074-pos-071301-well 51 | 5.4 | 609.18 | | | |
| CP0074-pos-071301-well 51 | 5.8 | 463.08 | | | |
| CP0074-pos-071301-well 51 | | | 4.7 | 6529 | 36 |
| CP0074-pos-071301-well 51 | | | 5.8 | 23113 | 76 |
| CP0074-pos-071301-well 52 | 4.5 | 625.14 | | | |
| CP0074-pos-071301-well 52 | 5.4 | 463.08 | | | |
| CP0074-pos-071301-well 52 | 6.9 | 315.06 | | | |
| CP0074-pos-071301-well 52 | 8.8 | 297.27 | | | |
| CP0074-pos-071301-well 52 | | | 4.5 | 42312 | 106 |
| CP0074-pos-071301-well 52 | | | 4.7 | 3209 | 22 |
| CP0074-pos-071301-well 52 | | | 4.9 | 3995 | 24 |
| CP0074-pos-071301-well 52 | | | 5.4 | 38681 | 100 |
| CP0074-pos-071301-well 53 | 4.4 | 609.14 | | | |
| CP0074-pos-071301-well 53 | 4.6 | 609.14 | | | |
| CP0074-pos-071301-well 53 | 4.8 | 609.14 | | | |
| CP0074-pos-071301-well 53 | 5.1 | 463.12 | | | |
| CP0074-pos-071301-well 53 | 6.6 | 315.06 | | | |
| CP0074-pos-071301-well 53 | | | 4.3 | 22471 | 93 |
| CP0074-pos-071301-well 53 | | | 4.4 | 56644 | 156 |
| CP0074-pos-071301-well 53 | | | 4.5 | 183171 | 294 |
| CP0074-pos-071301-well 53 | | | 4.6 | 239990 | 339 |
| CP0074-pos-071301-well 53 | | | 4.8 | 34417 | 118 |
| CP0074-pos-071301-well 54 | 4.1 | 625.14 | | | |
| CP0074-pos-071301-well 54 | 4.6 | 640.16 | | | |
| CP0074-pos-071301-well 54 | 4.9 | 609.14 | | | |
| CP0074-pos-071301-well 54 | 5.3 | 609.14 | | | |
| CP0074-pos-071301-well 54 | 6.7 | 301.06 | | | |
| CP0074-pos-071301-well 54 | | | 4.2 | 7689 | 105 |
| CP0074-pos-071301-well 54 | | | 4.7 | 16326 | 202 |
| CP0074-pos-071301-well 54 | | | 5.0 | 84774 | 3050 |
| CP0074-pos-071301-well 54 | | | 5.8 | 2281 | 35 |
| CP0074-pos-071301-well 54 | | | 6.5 | 1490 | 24 |
| CP0074-pos-071301-well 55 | 4.7 | 640.16 | | | |
| CP0074-pos-071301-well 55 | 5.0 | 609.14 | | | |
| CP0074-pos-071301-well 55 | 5.3 | 609.14 | | | |
| CP0074-pos-071301-well 55 | 5.8 | 463.08 | | | |
| CP0074-pos-071301-well 55 | 7.4 | 315.06 | | | |
| CP0074-pos-071301-well 55 | | | 4.3 | 38220 | 124 |
| CP0074-pos-071301-well 55 | | | 4.6 | 35784 | 123 |
| CP0074-pos-071301-well 55 | | | 4.8 | 117214 | 162 |
| CP0074-pos-071301-well 55 | | | 5.0 | 1625216 | 586 |
| CP0074-pos-071301-well 55 | | | 5.9 | 113698 | 160 |
| CP0074-pos-071301-well 57 | 5.5 | 463.12 | | | |
| CP0074-pos-071301-well 57 | 7.0 | 315.06 | | | |
| CP0074-pos-071301-well 57 | | | 4.8 | 84974 | 93 |
| CP0074-pos-071301-well 57 | | | 5.0 | 77894 | 87 |
| CP0074-pos-071301-well 57 | | | 5.1 | 18199 | 33 |
| CP0074-pos-071301-well 57 | | | 5.3 | 12286 | 27 |
| CP0074-pos-071301-well 57 | | | 5.5 | 58311 | 71 |
| CP0074-pos-071301-well 58 | 5.4 | 447.09 | | | |
| CP0074-pos-071301-well 58 | 5.6 | 463.12 | | | |
| CP0074-pos-071301-well 58 | 7.3 | 315.06 | | | |
| CP0074-pos-071301-well 58 | | | 5.0 | 9741 | 64 |
| CP0074-pos-071301-well 58 | | | 5.1 | 6228 | 57 |
| CP0074-pos-071301-well 58 | | | 5.3 | 2204 | 45 |
| CP0074-pos-071301-well 58 | | | 5.4 | 23691 | 83 |
| CP0074-pos-071301-well 58 | | | 5.7 | 16324 | 74 |
| CP0074-pos-071301-well 59 | 5.8 | 463.12 | | | |
| CP0074-pos-071301-well 59 | 7.5 | 315.06 | | | |
| CP0074-pos-071301-well 59 | | | 5.1 | 3218 | 26 |
| CP0074-pos-071301-well 59 | | | 5.3 | 1925 | 22 |
| CP0074-pos-071301-well 59 | | | 5.8 | 3736 | 28 |
| CP0074-pos-071301-well 59 | | | 7.5 | 1397 | 20 |
| CP0074-pos-071301-well 60 | 5.4 | 463.12 | | | |
| CP0074-pos-071301-well 60 | 5.5 | 345.21 | | | |
| CP0074-pos-071301-well 60 | 6.9 | 315.06 | | | |
| CP0074-pos-071301-well 60 | 8.7 | 323.28 | | | |

TABLE 2-continued

HPLC/MS/ELSD Data on the Chromatographic Fractions of the
Leaves and Stems of Baptisia alba according to the Invention.

| FILENAME | MS RT | M + H Ion | ELSD RT | ELSD Area | Weight ELSD |
|---|---|---|---|---|---|
| CP0074-pos-071301-well 60 | | | 4.7 | 3037 | 21 |
| CP0074-pos-071301-well 60 | | | 5.4 | 1639 | 17 |
| CP0074-pos-071301-well 60 | | | 6.9 | 4304 | 25 |
| CP0074-pos-071301-well 61 | 5.5 | 274.17 | | | |
| CP0074-pos-071301-well 61 | 6.6 | 315.06 | | | |
| CP0074-pos-071301-well 61 | | | 4.5 | 2946 | 28 |
| CP0074-pos-071301-well 61 | | | 6.6 | 1247 | 18 |
| CP0074-pos-071301-well 62 | 5.0 | 609.14 | | | |
| CP0074-pos-071301-well 62 | 7.2 | 315.06 | | | |
| CP0074-pos-071301-well 62 | | | 5.1 | 4548 | 66 |
| CP0074-pos-071301-well 63 | 6.8 | 338.07 | | | |
| CP0074-pos-071301-well 63 | 7.4 | 315.06 | | | |
| CP0074-pos-071301-well 63 | | | 5.2 | 4206 | 107 |
| CP0074-pos-071301-well 63 | | | 7.6 | 1478 | 105 |
| CP0074-pos-071301-well 67 | 8.1 | 478.29 | | | |
| CP0074-pos-071301-well 67 | | | 0.0 | 0 | |
| CP0074-pos-071301-well 68 | 6.9 | 315.06 | | | |
| CP0074-pos-071301-well 68 | 8.8 | 297.27 | | | |
| CP0074-pos-071301-well 68 | | | 0.0 | 0 | |
| CP0074-pos-071301-well 69 | 6.6 | 315.06 | | | |
| CP0074-pos-071301-well 69 | | | 0.0 | 0 | |
| CP0074-pos-071301-well 75 | 8.1 | 677.30 | | | |
| CP0074-pos-071301-well 75 | | | 8.1 | 1599 | 21 |
| CP0074-pos-071301-well 76 | 7.5 | 677.35 | | | |
| CP0074-pos-071301-well 76 | 9.0 | 297.27 | | | |
| CP0074-pos-071301-well 76 | | | 7.4 | 2124 | 18 |
| CP0074-pos-071301-well 76 | | | 7.6 | 44841 | 110 |
| CP0074-pos-071301-well 77 | 7.3 | 677.35 | | | |
| CP0074-pos-071301-well 77 | 7.8 | 517.29 | | | |
| CP0074-pos-071301-well 77 | | | 7.3 | 21262 | 90 |
| CP0074-pos-071301-well 77 | | | 7.8 | 8918 | 54 |
| CP0074-pos-071301-well 78 | 9.0 | 331.27 | | | |
| CP0074-pos-071301-well 78 | | | 0.0 | 0 | |
| CP0490-well 3 | 1.4 | 235.63 | | | |
| CP0490-well 3 | 3.4 | 325.57 | | | |
| CP0490-well 3 | | | 2.6 | 4130 | 19 |
| CP0490-well 3 | | | 2.7 | 2367 | 16 |
| CP0490-well 3 | | | 2.9 | 3532 | 18 |
| CP0490-well 3 | | | 2.9 | 3528 | 18 |
| CP0490-well 3 | | | 3.0 | 4137 | 19 |
| CP0490-well 3 | | | 3.4 | 11487 | 32 |
| CP0490-well 4 | 1.4 | 235.63 | | | |
| CP0490-well 4 | 2.2 | 251.61 | | | |
| CP0490-well 4 | 2.8 | 251.61 | | | |
| CP0490-well 4 | | | 1.9 | 1436 | 11 |
| CP0490-well 4 | | | 2.8 | 2858 | 14 |
| CP0490-well 4 | | | 3.0 | 4833 | 18 |
| CP0490-well 4 | | | 3.3 | 1222 | 10 |
| CP0490-well 5 | 1.4 | 235.63 | | | |
| CP0490-well 5 | 2.8 | 188.47 | | | |
| CP0490-well 5 | | | 2.5 | 1836 | 15 |
| CP0490-well 5 | | | 2.9 | 18201 | 55 |
| CP0490-well 5 | | | 3.3 | 4614 | 24 |
| CP0490-well 6 | 1.3 | 235.63 | | | |
| CP0490-well 6 | 2.8 | 188.47 | | | |
| CP0490-well 6 | | | 2.6 | 1099 | 12 |
| CP0490-well 6 | | | 2.6 | 1689 | 18 |
| CP0490-well 6 | | | 2.7 | 1764 | 19 |
| CP0490-well 6 | | | 2.8 | 2439 | 25 |
| CP0490-well 6 | | | 2.9 | 4971 | 47 |
| CP0490-well 7 | 1.1 | 235.60 | | | |
| CP0490-well 7 | | | 2.9 | 38531 | 27 |
| CP0490-well 7 | | | 3.4 | 11926 | 15 |
| CP0490-well 7 | | | 3.4 | 8896 | 13 |
| CP0490-well 8 | 1.2 | 235.60 | | | |
| CP0490-well 8 | | | 2.6 | 3726 | 7 |
| CP0490-well 8 | | | 2.9 | 2184 | −1 |
| CP0490-well 8 | | | 3.1 | 6001 | 16 |
| CP0490-well 8 | | | 3.2 | 2479 | 1 |
| CP0490-well 8 | | | 3.2 | 2038 | −1 |
| CP0490-well 8 | | | 3.5 | 13949 | 39 |
| CP0490-well 9 | 1.1 | 235.63 | | | |
| CP0490-well 9 | | | 3.4 | 3586 | 11 |
| CP0490-well 10 | 1.4 | 235.63 | | | |

TABLE 2-continued

HPLC/MS/ELSD Data on the Chromatographic Fractions of the
Leaves and Stems of Baptisia alba according to the Invention.

| FILENAME | MS RT | M + H Ion | ELSD RT | ELSD Area | Weight ELSD |
|---|---|---|---|---|---|
| CP0490-well 10 | | | 3.5 | 1466 | 28 |
| CP0490-well 11 | 1.5 | 235.63 | | | |
| CP0490-well 11 | | | 4.0 | 1819 | 14 |
| CP0490-well 12 | 1.4 | 235.63 | | | |
| CP0490-well 12 | | | 3.8 | 7450 | 23 |
| CP0490-well 12 | | | 4.0 | 43248 | 72 |
| CP0490-well 12 | | | 4.1 | 34152 | 61 |
| CP0490-well 14 | 1.3 | 235.63 | | | |
| CP0490-well 14 | | | 3.9 | 34804 | 250 |
| CP0490-well 14 | | | 4.1 | 188525 | 823 |
| CP0490-well 14 | | | 4.3 | 21972 | 173 |
| CP0490-well 15 | 1.2 | 235.63 | | | |
| CP0490-well 15 | 4.2 | 287.44 | | | |
| CP0490-well 15 | | | 4.0 | 1229 | 9 |
| CP0490-well 15 | | | 4.2 | 238118 | 100 |
| CP0490-well 15 | | | 4.4 | 359411 | 135 |
| CP0490-well 16 | 1.4 | 235.63 | | | |
| CP0490-well 16 | 4.3 | 287.44 | | | |
| CP0490-well 16 | | | 4.5 | 38689 | 87 |
| CP0490-well 17 | 1.2 | 235.63 | | | |
| CP0490-well 17 | | | 4.8 | 6709 | 14 |
| CP0490-well 18 | 1.4 | 235.63 | | | |
| CP0490-well 18 | 4.8 | 609.41 | | | |
| CP0490-well 18 | 5.7 | 549.39 | | | |
| CP0490-well 18 | | | 4.8 | 236312 | 129 |
| CP0490-well 18 | | | 5.0 | 1654 | 28 |
| CP0490-well 18 | | | 5.7 | 13676 | 47 |
| CP0490-well 19 | 1.4 | 235.63 | | | |
| CP0490-well 19 | 4.7 | 609.41 | | | |
| CP0490-well 19 | 7.0 | 315.49 | | | |
| CP0490-well 19 | | | 4.7 | 271230 | 243 |
| CP0490-well 19 | | | 5.0 | 4392 | 20 |
| CP0490-well 19 | | | 5.7 | 3995 | 19 |
| CP0490-well 19 | | | 7.0 | 6414 | 23 |
| CP0490-well 20 | 1.4 | 235.63 | | | |
| CP0490-well 20 | 4.7 | 609.41 | | | |
| CP0490-well 20 | | | 4.8 | 151322 | 160 |
| CP0490-well 20 | | | 5.0 | 1980 | 12 |
| CP0490-well 20 | | | 5.1 | 4917 | 18 |
| CP0490-well 21 | 0.0 | 0.00 | | | |
| CP0490-well 21 | | | 4.8 | 1968 | 15 |
| CP0490-well 21 | | | 5.1 | 14686 | 48 |
| CP0490-well 21 | | | 5.2 | 1910 | 15 |
| CP0490-well 22 | 5.4 | 463.43 | | | |
| CP0490-well 22 | | | 5.0 | 1305 | 14 |
| CP0490-well 22 | | | 5.1 | 2619 | 27 |
| CP0490-well 22 | | | 5.4 | 22542 | 176 |
| CP0490-well 22 | | | 7.2 | 1089 | 12 |
| CP0490-well 24 | 5.7 | 311.66 | | | |
| CP0490-well 24 | | | 5.8 | 2782 | 3 |
| CP0490-well 25 | 5.6 | 311.66 | | | |
| CP0490-well 25 | | | 6.0 | 2203 | 10 |
| CP0490-well 28 | 0.0 | 0.00 | | | |
| CP0490-well 28 | | | 4.8 | 1029 | 10 |
| CP0490-well 28 | | | 6.5 | 21523 | 45 |
| CP0490-well 29 | 6.4 | 301.48 | | | |
| CP0490-well 29 | | | 6.4 | 3457 | 21 |
| CP0490-well 34 | 1.4 | 235.65 | | | |
| CP0490-well 34 | 7.4 | 285.49 | | | |
| CP0490-well 34 | 7.8 | 518.60 | | | |
| CP0490-well 34 | | | 7.5 | 1278 | 27 |
| CP0490-well 36 | 1.4 | 235.65 | | | |
| CP0490-well 36 | | | 0.0 | 0 | |
| CP0490-well 37 | 1.4 | 235.65 | | | |

EXAMPLE 3

This example describes a high-throughput method for the production, analysis, and characterization of large libraries of small-molecules from natural resources, which accelerates the natural product drug discovery process for pharmaceutical and biotech industries. The library production process integrates automated flash chromatography, solid phase extraction, filtration, and parallel four-channel preparative high-performance liquid chromatography (HPLC) to produce the libraries in 96- or 384-well plates. The libraries consist of purified fractions with approximately one to five compounds per well. The libraries are analyzed prior to biological screening by a parallel eight channel LC-ELSD-MS system that determines the molecular weight and the number and quantity of compounds in a fraction. After biological screening of the libraries, active compounds are rapidly purified and activities are confirmed. The structures of active compounds discovered in the libraries are elucidated using a combination of NMR data, acquired on about 50 micrograms of material using a Bruker Avance 600 MHz NMR spectrometer equipped with a novel capillary (5 µL) microcoil flow probe and MS data from the LC-MS database. Using these high-throughput methods, a natural product library containing 36,000 fractions from diverse plant collections were produced and analyzed, and screened in various drug discovery programs. As a demonstration, a small-molecule library was made from the stem bark of *Taxus brevifolia*. Biological screening in the NCI in vitro panel of 3 cancer cell lines demonstrates that the library enables the discovery of highly active anticancer compounds, whose activities are not detected in the flash fractions from which the library originates.

According to this example, high-throughput technologies may be applied to generate large libraries of purified fractions of small-molecule natural products rapidly for HTS. The production process begins with the fractionation of polar and non-polar plant extracts using automated flash chromatography. The resulting flash fractions are subjected to solid-phase extraction to remove tannins and to molecular weight cut-off filters to remove high molecular weight components in flash fractions from polar extracts. Flash fractions are further separated using a parallel four-channel reversed-phase preparative HPLC system resulting in fractions, which contain a mixture of about 5 compounds/well. The fractions are analyzed by a parallel eight-channel analytical LC-ELSD-MS system. The fractions containing detectable compounds are collectively called "the library", from which more focused libraries are drawn for biological screening. After biological screening, the individual compounds of the active fractions are rapidly purified and the activities of the compounds are confirmed. Using a Bruker Avance 600 MHz NMR spectrometer equipped with a new capillary (5 µL) microcoil flow probe with an active volume of only 1.5 µL, 5-10 µg of a pure compound is sufficient for 1H and COSY experiments to characterize and dereplicate known structures. To characterize novel structures, approximately 50 µg pure compound is needed to acquire additional experiments such as a gHMQC and a gHMBC.

The high-throughput method described herein was used in the production process of large libraries of small-molecule natural products and to illustrate the process a library was prepared from an extract of *Taxus brevifolia*, the pacific yew tree containing paclitaxel (Taxol) and many of its derivatives. The resulting *Taxus* library was analyzed by parallel eight-channel LC-ELSD-MS. Library fractions were screened by the National Cancer Institute (NCI) in 3 cancer cell lines. Screening results indicate that the presentation of natural products to biological screening in the form of libraries produced as described here, enables the discovery of highly active, minor metabolites whose activities would otherwise go undetected. Several flash fractions obtained during the production of the *Taxus* library did not show activity in the assays, whereas several library fractions resulting from these flash fractions did. The active compounds, 7-(β-xylosyl)-taxol, 7-(β-xylosyl)-taxol C, and 7-(β-xylosyl)-10-deacetyltaxol C, were quickly dereplicated using their molecular weights determined during LC-ELSD-MS analysis of the library and the structures were characterized using 1H and COSY experiments. These compounds were previously reported from the stem bark of *Taxus baccata* and possess potent activity against B16 melanoma.

The instrumentation used in the method of this example was as follows. Flash chromatography separations were performed on 50 gram Si and C18 flash columns (International Sorbent Technology Ltd., Mid Glamorgan, UK) using a Flash Master II automated chromatographic system (Jones Chromatography Inc., Lakewood, Colo.). The removal of tannins was performed using a 500 mg or a 2.5 g polyamide-filled cartridge (Jones Chromatography Inc.). Preparative HPLC separations were performed on Betasil C18 columns (20×100 mm, 5 µm, Keystone Scientific Inc., Bellefonte, Pa.). A parallel four-channel preparative HPLC system was assembled and consisted of 4 Beckman System Gold 126 gradient HPLC pumps (Beckman Coulter Inc., Fullerton, Calif.) with system controllers and four-way solvent delivery modules, 4 Beckman System Gold 166 single wavelength UV detectors with preparative flow cells, a Gilson 215/849 multiple probe autosampler (Gilson Inc., Middleton, Wis.), and 4 Gilson 204 fraction collectors. The system was controlled by Beckman 32 Karat chromatography software. A Mega 1200 evaporator (Genevac Technologies, Suffolk, UK) was used to remove solvents from the preparative HPLC fractions. The preparative HPLC fractions were transferred from tubes to 96-deep-well plates by a Packard MultiProbe II liquid handling system (Packard BioScience Company, Meriden, Conn.). Focused libraries for screening were prepared in either 96- or 384-well plates using the same liquid handling system. A Genevac HT-12 evaporator was used to remove solvents from the 96- and 384-well plates. A parallel eight-channel LC-ELSD-MS system was assembled and consisted of a LCT time-of-flight mass spectrometer with an eight-way MUX electrospray interface (Micromass Ltd, Manchester, UK), a Waters 600E Multisolvent Delivery System (Wasters Corporation, Milford, Mass.) to pump solvents through an eight-way manifold which splits the flow to 8 HPLC columns (4.6×50 mm, 3 µm, Keystone Betasil C-18), a Gilson 215/889 multiple probe autosampler, and 8 Alltech 500 ELSD detectors (Alltech Associates Inc., Deerfield, Ill.). The system was controlled by MicroMass MassLynx software. Data analysis was performed using the OpenLynx Software followed by Extractor, a customized software package developed for Sequoia Sciences by Koch Associates, La Jolla, Calif. The isolation of individual compounds was performed using semi-preparative Keystone Betasil C18 or C8 columns (8×250 mm I.D., 5 µm) on a single channel Beckman HPLC system consisting of a Beckman 168 diode array UV detector, Sedex ELSD detector (Richard Scientific Inc., Novato, Calif.), and Gilson 204 fraction collector (a splitter is used to split the flow in 10:90 to ELSD and fraction collector). Size exclusion chromatographic analyses were conducted on a single channel analytical Beckman HPLC system using Macrosphere GPC column (4.6×250 mm, 7 µm, Alltech Associates, Inc.) and Sedex ELSD detector. NMR data for the structure elucidation of compounds were acquired utilizing a Bruker Avance 600 MHz NMR system (Bruker, Rheinstetten, Germany) and a 5 µL capillary microcoil NMR flow probe with 1.5 µL active volume (Magnetic Resonance Microsensors, Savoy, Ill.), a Harvard 22 syringe pump (Harvard Apparatus Inc., Holliston, Mass.) and a Valco 6 port injection valve (Valco Instruments Co. Inc., Houston, Tex.) and 3 µL loop as the sample loading device.

Plant samples consisted of whole plant material or separated plant parts such as roots, stems, leafs, flowers and fruits, or various combinations of parts. Plant samples from Gabon were dried immediately after collection above a gas-powered plant drier. Plant samples from the USA were shipped frozen. Frozen plants samples were lyophilized upon arrival. Low purity Taxol (extract of the stem bark of *Taxus brevifolia* adsorbed onto silica) was purchased from Hauser Chemical Research Inc. (Boulder, Colo.).

Dried plant material (150 g) was ground to a homogenous powder. The powder was sonicated for 30 minutes in an organic solvent mixture of EtOH:EtOAc (50:50) followed by igorous shaking for exhaustive extractions (two times, 4 and 8 hours each). After filtration and removing the organic solvents by rotary evaporation the organic extract was obtained. The remaining residue was exhaustively extracted using an aqueous solvent mixture of H2O:MeOH (30:70) (two times, 4 and 8 hours each). The aqueous extract was obtained after removing the solvents by rotary evaporation. The low purity taxol powder was exhaustively extracted with EtOH:EtOAc (50:50). After filtration the taxol preparation was dried by rotary evaporation. This taxol extract (TX001) was treated as an organic extract.

Organic extract material (1 g) was dissolved in 5 mL MeOH:EtOAc (50:50) and adsorbed onto 5 g of silica powder. The dried powder was brought onto a 50 g silica column and eluted on the flash chromatography system using a step gradient of 1) 75% hexanes, 25% EtOAc, 2) 50% hexanes, 50% EtOAc, 3) 100% EtOAc, 4) 75% EtOAc, 25% MeOH, 5) 50% EtOAc, 50% MeOH. The Flash Master II was modified to collect large fractions of 250 mL of solvent per gradient step. The system was set up to perform automated separations of 10 samples per loading. Flash fraction 1 was discarded, whereas fractions 2 to 5 were dried by rotary evaporation. Flash fractions 4 and 5 were screened for the presence of tannins by LC-MS and passed over a 2.5 g polyamide column if results were positive. Flash fractions produced from the *Taxus* organic extract were named TX002 to TX005. Aqueous extract (2 g) was dissolved into 10 mL of water and the resulting suspension was centrifuged: The aqueous layer was brought onto a 50 g C18 column (pre-rinsed with 1 column volume methanol and 5 column volumes water). Any insoluble material was again dissolved into 10 mL water using sonication. The suspension was centrifuged again. The aqueous layer was also brought onto the column. The column was then rinsed with 5 column volumes water and the effluent was discarded. The remaining insoluble material was subsequently taken into 10 mL methanol. The methanol layer was brought onto the column. The column was eluted with one column volume methanol to remove water from the column and a 500 mg polyamide cartridge in methanol was attached to the bottom of the column. The column was eluted with 5 column volumes methanol. The resulting fraction (flash fraction 6, 100 mg) was dissolved in MeOH:H2O (60:40, 15 mL) and filtered at 3000 g for 8 hours using Centricon filter units with a molecular weight cut-off of 3000 amu. The retentate, typically 1-2 mL was discarded. Analytical size exclusion chromatography showed that the content of high molecular weight constituents (>3000 amu) in the filtrate was reduced significantly from up to 75% to less than 10% of the total amount of material using ELSD detection.

Flash fraction material (50 mg) was dissolved into either 1000 μL of MeOH:EtOAc (70:30) (for flash fractions 2 and 3 of organic extracts) or 100% MeOH (for flash fractions 4 and 5 of the organic extracts and flash fraction 6 of the aqueous fraction) and filtered where necessary. The fractions were separated into 40 fractions (20 mL/min, 1 min per collection per tube) using the parallel four-channel preparative HPLC system. A different 35 min gradient was applied to each flash fraction for adequate separation: flash fraction 2: 40-80% acetonitrile in water, flash fraction 3: 30-70% acetonitrile in water, flash fraction 4: 20-60% acetonitrile in water, flash fractions 5 and 6: 10-50% acetonitrile in water. The 40 tubes containing HPLC fractions were dried in the Mega 1200 Evaporator. The HPLC fractions were transferred to 96-deep-well plates using the liquid handling system (Packard MultiProbe II). A *Taxus* library was made from *Taxus* flash fractions (TX002 to TX005) consisting of a total of 160 samples named TX002-1 to 40 to TX005-1 to 40, respectively.

All samples were analyzed by a parallel eight channel LC-ELSD-MS system with chromatographic conditions of 5% acetonitrile in water for the first 1.0 minutes, a linear gradient of acetonitrile from 5% to 95% in 8.0 minutes, followed by 95% acetonitrile in water for 1.0 minutes. After each analysis the column was equilibrated at 5% acetonitrile in water for 2.5 minutes. Data processing was performed automatically starting with OpenLynx, followed by a customized software package, Extractor, to automatically extract all graphic information, such as retention times, mass spectra, and peak integrations, and convert it to text to allow it to be transferred to a database for storage and analysis.

In vitro cytotoxicity tests were conducted at the NCI using an in vitro 3-cell-line panel consisting of MCF7 breast cancer, NCI-H460 lung cancer, and SF-268 CNS cancer. Each cell line was inoculated and incubated in microtiter plates. After 24 hours test samples were added to a final assay concentration of 2 μg/mL and the culture was incubated for 48 hours. Results for each test sample were reported as the percentage of growth of the treated cells when compared to untreated controls. Compounds which reduced the growth of any one of the cell lines by 32% or less against standard were considered to be active.

The constituents of active library fractions were purified using a single channel HPLC system. The gradient applied to the separations was based on the elution profile observed during the preparative HPLC separation that created the fraction and was optimized for base line separation of the compounds. The purification required approximately 100 μg per separation and the yield per compound was typically in the range of 5 to 50 μg per compound. Pure compounds were dissolved into 3 μL CD3OD and loaded onto the microcoil NMR flow probe using a syringe pump equipped with a sample injection valve and capillary tubing. A sample of 5 to 50 μg was used to run a 1D 1H spectrum (64 scans, 8 or 16 increments) and a gCOSY spectrum (256 scans, 16 increments). The probe was operated at a temperature of 293K. Pulse widths were 5.5 μs at a power of 23 dB for the 1H spectra. This information together with the molecular ions from the LC-ELSD-MS analysis was used to verify the structure of previously reported molecules. Novel structures for which 50 μg could be obtained were identified using additional experiments such as gHMQC and gHMBC and high-resolution mass spectra were generated by TOF mass spectrometry for the determination of molecular formula.

Figure 14:
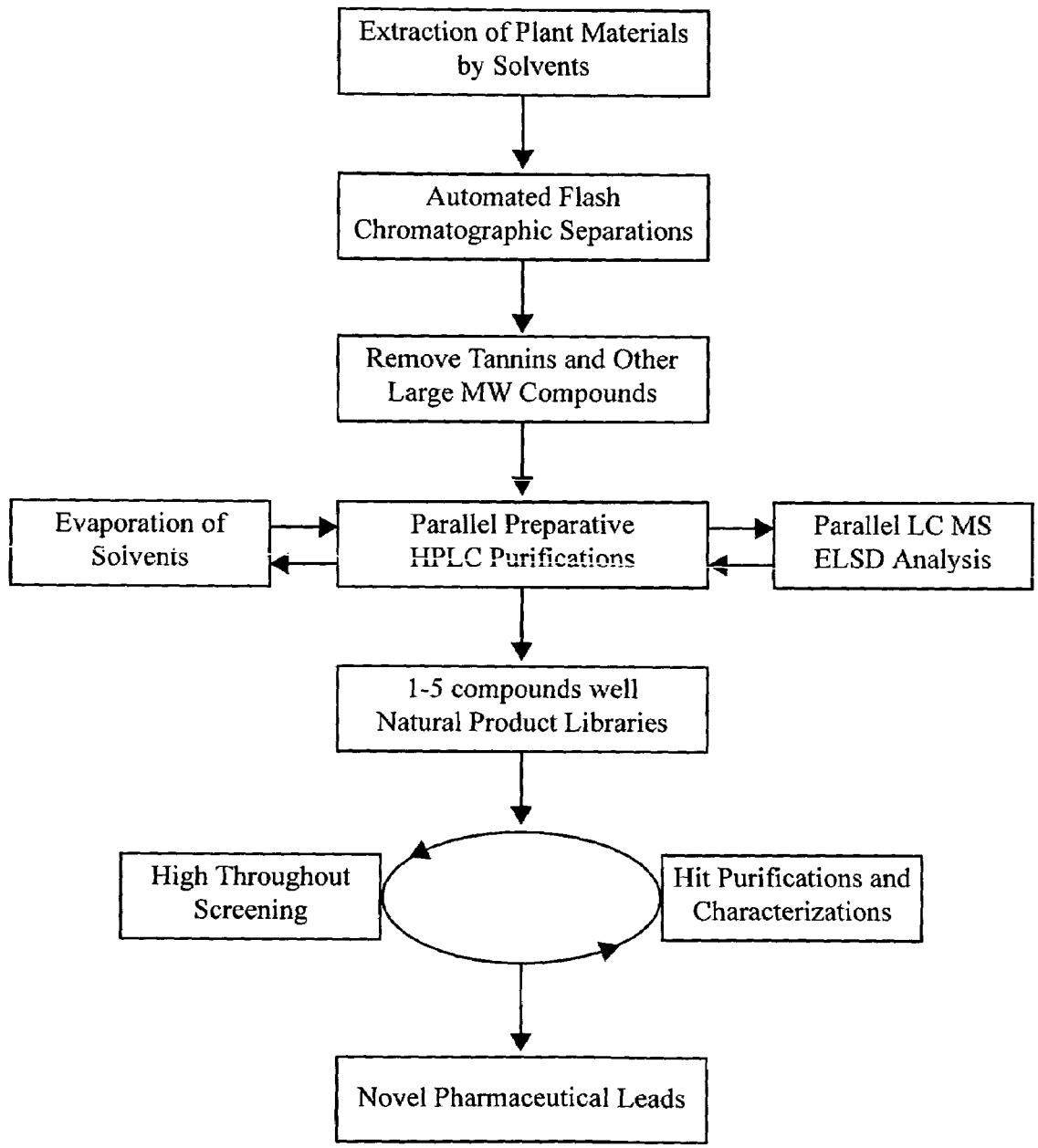
FIG. 14 is a schematic presentation of the method for high-throughput natural product drug discovery.
Figure 15:
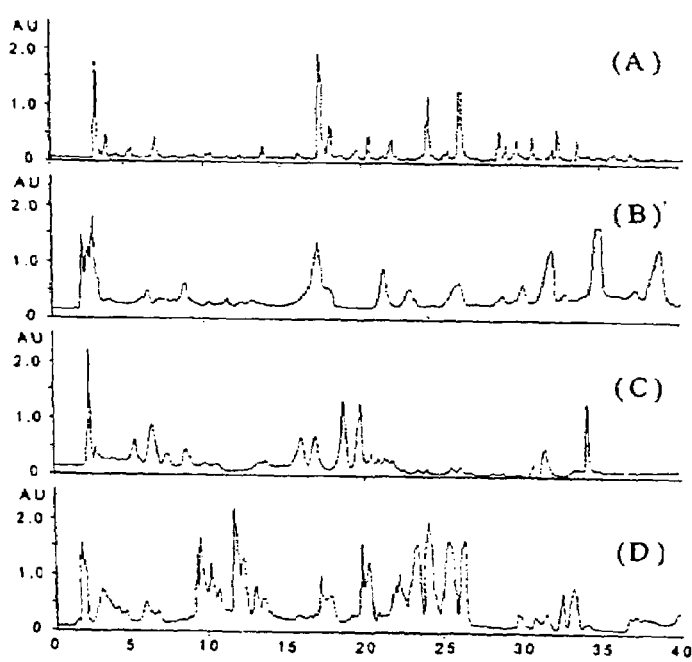
FIG. 15 is a group of chromatograms each yielding 40 natural product library fractions; (A) to (D) showing the channels 1 to 4 in one parallel four-channel preparative HPLC run.

Most drug discovery programs today are capable of screening large numbers of compounds against multiple targets using micro-gram quantities of material. To meet the demand for large numbers of structurally diverse compound libraries, a high-throughput method to accelerate the natural product drug discovery process was developed. FIG. 14 is a schematic presentation that depicts the strategy by which the natural product libraries were produced and screened, active hits were purified, and biologically active compounds were characterized for pharmaceutical discovery programs. Reversed-phase, preparative HPLC is automated, parallel four-channel preparative system has increased the efficiency of this technique four-fold. A four-channel preparative HPLC system was customized in the laboratory. It operates 4 gradient pumping systems independently but simultaneously, permitting 10 parallel separations of 4 samples per run. Since the systems are delivering the effluents independently to each preparative column the separations for each channel have the same efficiency. Because of the complexity of natural product extracts, the separation of naturally occurring drug-like compounds with acceptable resolution and yield requires several steps of cleanup and pre-separation procedures before loading samples onto a preparative column. The purification of plant extracts using normal-phase or reversed-phase flash chromatography, solid phase extraction using polyamide, and filtration through molecular weight cut-off filters, removes highly lipophilic and hydrophilic compounds, pigments, large molecular weight tannins, polysaccharides, and other non-drug-like molecules. The optimized gradient chromatography separates 50 mg of flash fractions and collected at 1 minute per tube with a total of 40 tubes per collection. Based on one sample per hour per channel, a parallel four-channel system can purify 32 samples in a working day, which generates 1280 fractions (32×40). The preparative HPLC fractions containing quantifiable compounds make up the library. These fractions consist of approximately 1-5 compounds per well and primarily from 0.1 to 1 mg of material. FIG. 15 is a typical example of chromatograms obtained from one run of a parallel four-channel preparative HPLC purification of library fractions. The production process was validated by processing a single sample repeatedly and comparing the resulting LC-ELSD-MS data of the preparative HPLC fractions. The LC-ELSD-MS information for plant samples processed repeatedly proved to be very reproducible and accurate. So far a library with 36,000 fractions containing 1-5 compounds per well has been produced.

Figure 16:
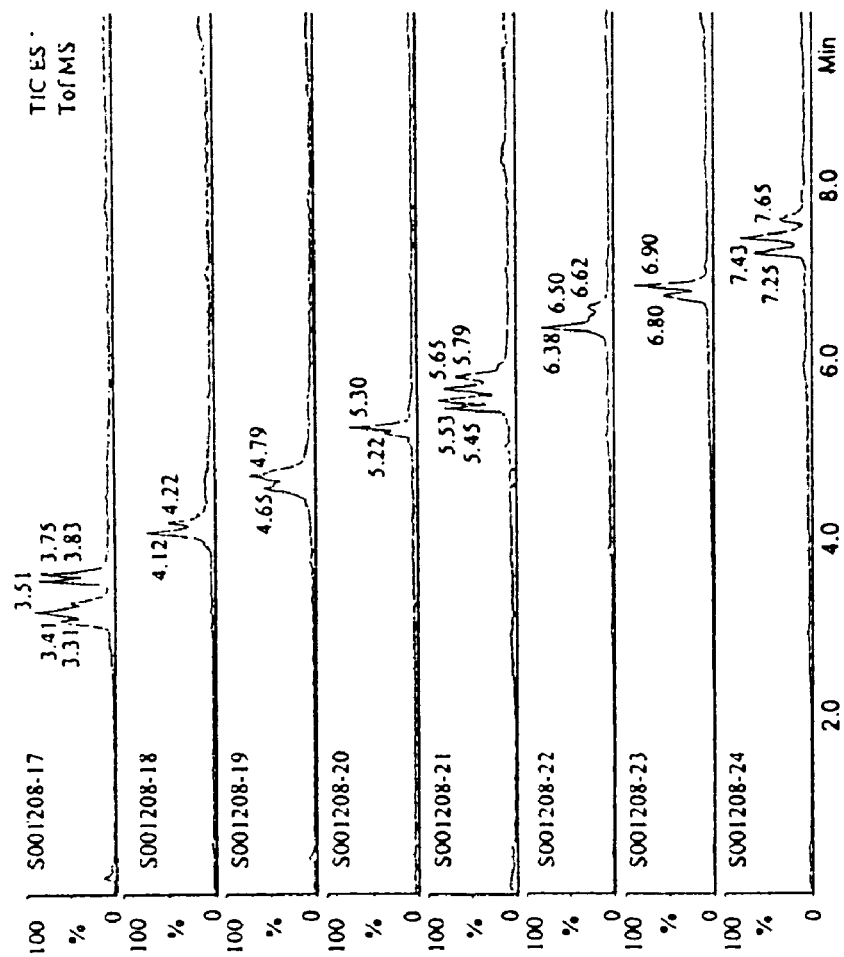
FIG. 16 is a series of spectra of eight LC-MS chromatograms of samples (S001208-17 to 24) by a single parallel LC-MS run from eight natural product library fractions.

To enable the analysis of large numbers of natural products, a method was developed using a parallel eight-channel LC-ELSD-MS system. Parallel LC-MS technology has recently been introduced to combinatorial chemistry and originated from U.S. Pat. No. 6,066,848, May 23, 2000. The methods employ a multiple sampling mass spectrometry interface now referred to as MUX technology. In addition to a parallel LC-MS interface, the system incorporates ELSD as a quantitative tool to determine the quantity of compounds in each fraction. ELSD is considered a universal detector with relatively good sensitivity and accuracy. After fractions were produced by parallel preparative HPLC, the fractions were transferred to 96-deep-well plates (rows 2-11). Prior to analysis of a plate, row 1 containing a mixture of 3 standards was injected to ensure acceptable system performance. The system operated at 10 minutes per run with 8 samples per run, one plate per 2.5 hours, 8 plates per day, and 40 plates per week. After large numbers of samples were analyzed, the retention time of the standard compounds shifted slightly. The standard compounds always served as points of reference and retention times were normalized to the standards. Data processing by the workstation of the parallel eight-channel LC-ELSD-MS was quite a challenge because each file contained large amounts of information. Software (Extractor) was developed to process these data to get information such as the molecular weights of the compounds, number of compounds per well, retention time and the integration of each peak in the chromatogram. At the same time the automated data processing software compares the standards with the samples to make corrections for retention time shifts from different channels of the chromatogram. All data in text format are exported to a database for characterization and dereplication of the compounds. FIG. 16 shows a series of typical parallel eight-channel LC-MS data from the natural product library. The mass spectra of relevant peaks for sample S001208 fraction 17 are as follows: Rt 3.31, m/z 491.4, Rt 3.41, m/z 404.5, Rt 3.51, m/z 238.5, Rt 3.75, m/z 597.2, Rt 3.83, m/z 475.5; S001208 fraction 18: Rt 4.12, m/z 371.2, Rt 4.22, m/z 497.5; S001208 fraction 19: Rt 4.65, m/z 509.4, Rt 4.79, m/z 509.4; S001208 fraction 20: Rt 5.22, m/z 509.4, Rt 5.30, m/z 799.5; S001208 fraction 21: Rt 5.45, m/z 922.2, Rt 5.53, m/z 1207.3, Rt 5.65, m/z 936.3, Rt 5.79, m/z 813.2; S001208 fraction 22: Rt 6.38, m/z 904.5, Rt 6.50, m/z 537.4, Rt 6.62, m/z 537.2; S001208 fraction 23: Rt 6.80, m/z 1052.2, Rt 6.90, m/z 918.4; S001208 fraction 24: Rt 7.25, m/z 1066.3, Rt 7.43, m/z 1066.2, Rt 7.65, m/z 1062.4.

Sample tracking and archiving of data are important when producing large natural product libraries. The taxonomic identity of each plant sample was determined after collection by plant taxonomists at the Missouri Botanical Garden. If the various plant parts were separated, a single species of plant yielded multiple samples. Plants samples were numbered and assigned a unique barcode after collection. The plant samples were weighed and the weights were recorded electronically into a relational database together with their taxonomic information, collection location (GPS coordinates), and any other ecological information. As a plant or a sample was further fractionated, the resulting extracts or fractions were assigned new barcodes at every step of the process. The use of barcodes and computerized balances ensured electronic data entry into the database. The database was used at every step of the process in the selection of samples for purification and to review information on previously purified samples.

Figure 17:
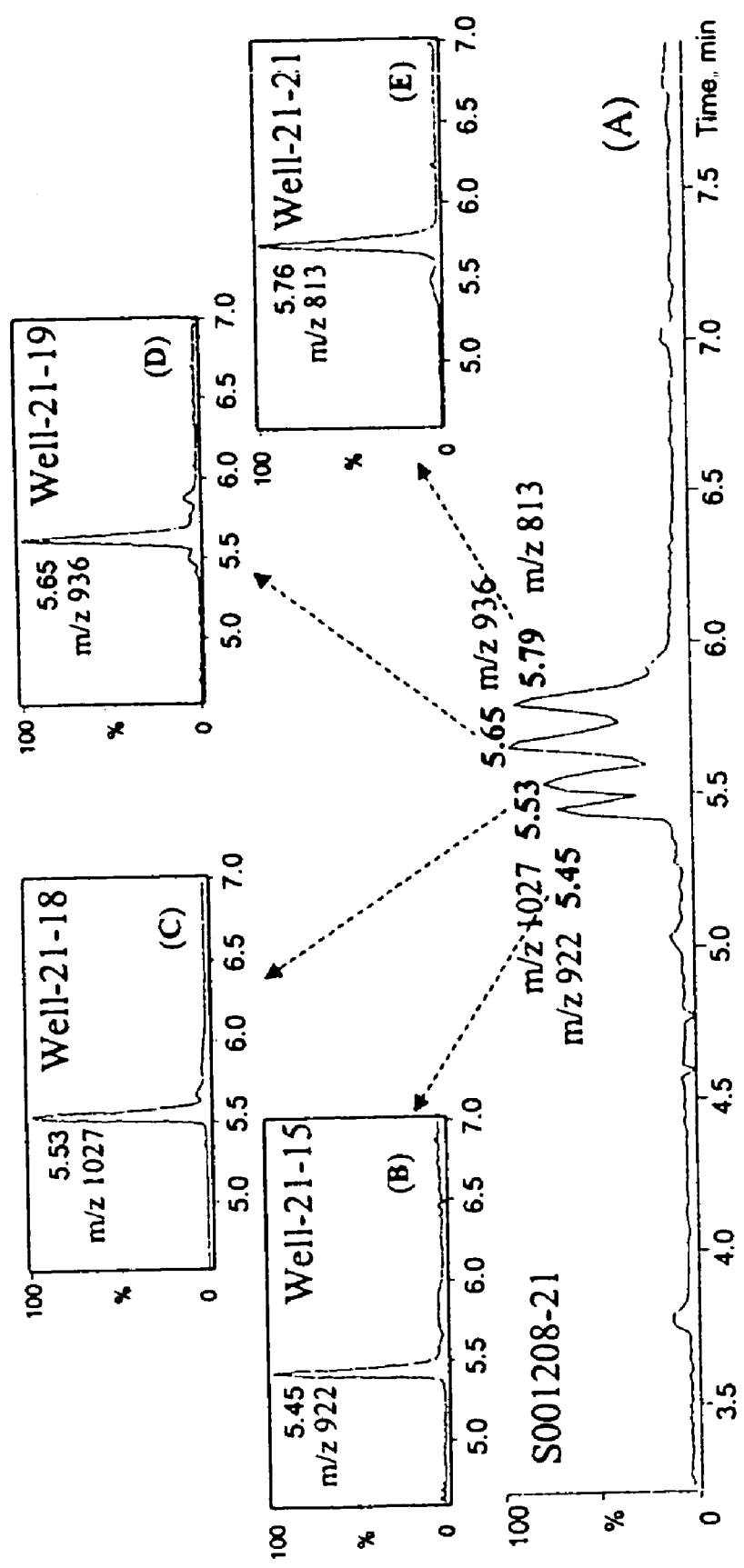
FIG. 17 is a spectrum showing that a bioactive library fraction containing 4 components was separated into pure compounds by adopting the preparative HPLC condition as described in Example 3, below; 4A: partial TIC chromatogram of 4 components; 4B-E: partial LC-ELDS chromatograms of each single compound after purification.

By this method, 36,000 samples of a natural product library were made. The library has been screened in various drug discovery programs against different biological targets. The hit rates have been 0.5% or lower depending upon the biological assay. Active compounds were isolated in quantities of 5 to 50 µg from approximately 100 µg of a preparative HPLC fraction. Since elution conditions, quantities, and molecular ions of the compounds in the library are known, the isolation of single compounds with purities greater than 85% has become a process amenable to standardization. After a single compound is obtained the biological activities of the compound are confirmed. The structures of active compounds were elucidated within a fraction of the time and with a fraction of the amount needed when compared to conventional natural products chemistry strategies. The standardization of the high-throughput library production and compound isolation process as described in this paper significantly reduced the time needed to identify active materials. In addition, the combination of the library production process and the high sensitivities of the latest NMR and LC-MS technologies, greatly reduced the amount of material needed for structure elucidation and dereplication, and consistent with the small amounts of material currently needed for HTS assays. FIG. 17 is an example of the purification of a bioactive library fraction containing 4 peaks into a total of 4 single components using a shallow-gradient, semi-preparative HPLC separation. The sample loading onto the column was about 100 µg and the recovery of each peak was approximately 5 to 50 µg. The possibility to work with such small quantities is an important step forward in natural product drug discovery.

Figure 18:
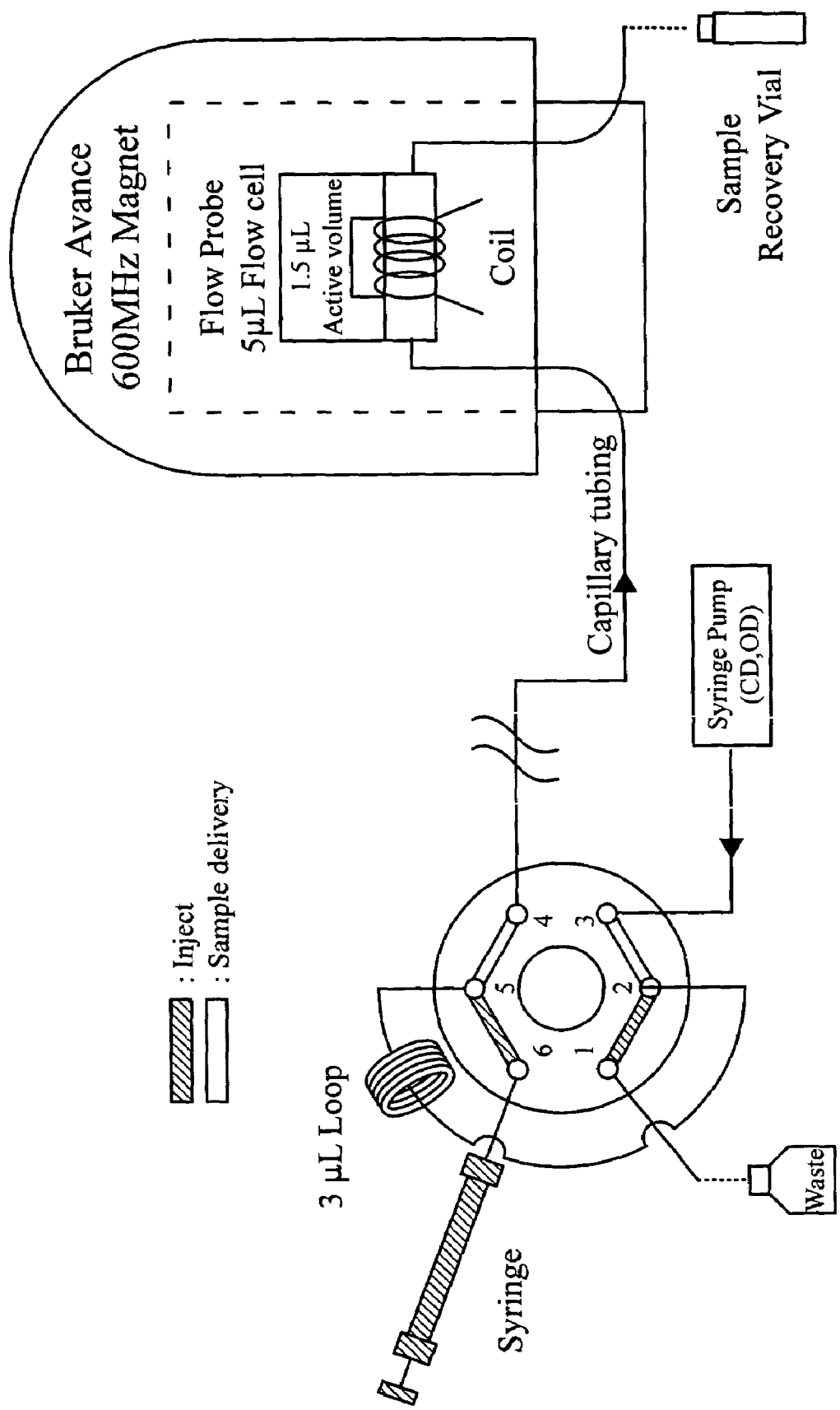
FIG. 18 is a schematic representation of the 5 μL microcoil flow probe NMR configuration with syringe pump and injection valve for low microgram sample handling.

High-resolution NMR is a routine tool used by chemists to elucidate the structures of compounds. Since conventional NMR employs either 5 or 3 mm tubes, most laboratories need low milligram quantities of sample to acquire all homo- and hetero-nuclear correlations for structure determination. If compounds are mass limited, as in the case of natural products drug discovery, obtaining low milligram quantities of sample requires multiple steps of separations and weeks or even months of time. With the advanced NMR technologies, in particular the microcoil flow probe (capillary-based microliter-volume flow probe) developed by Dean Olson and Jonathan Sweedler and now commercialized by MRM (Magnetic Resonance Microsystems, also called µFlowProbe™), it dramatically improves the acquisition of NMR spectra on samples in trace quantities. The new 5 µL microcoil flow probe reduces the active volume inside the coil to 1.5 µL, when compared to the conventional microliter-volume flow probes (40-200 µL) currently on the market, and the placement of the coil directly around the capillary results in further enhancement of mass sensitivity (signal to noise per mass unit). This characterization laboratory has implemented a system that permits one to work routinely with mass limited samples at the low microgram levels. As shown in FIG. 18, a syringe pump operating at 5 µL per minute pushed the sample to the microcoil probe in 2.5 minutes and parked the sample inside the probe. After the acquisition is completed the sample was collected in recovery vials. Sample loading was typically done in 3 µL with 5 to 50 µg quantities. 1D 1H NMR spectra and high-resolution mass spectra can be generated on isolated compounds of 5 to 50 µg in quantity providing the necessary data for characterization and dereplication. Working at the low microgram level, instead of the low milligram level, appears to be a tremendous advancement in natural products chemistry. These techniques should open doors enabling chemists to readily discover bioactive components among the minor constituents of natural resources.

Figure 19:
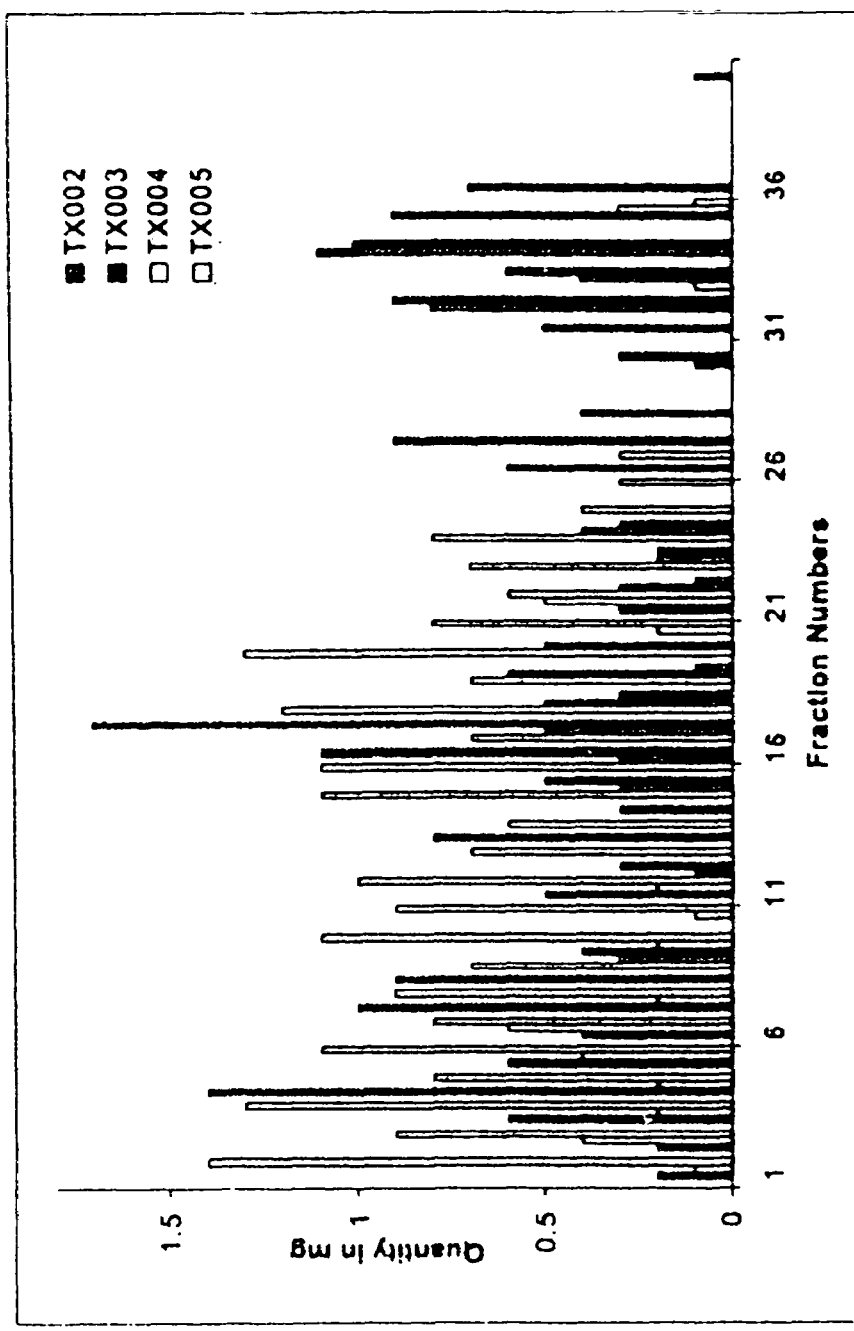
FIG. 19 is a graph of the *Taxus* library that was made using a high-throughput method of the present invention showing weights of each well in mg.
Figure 20:
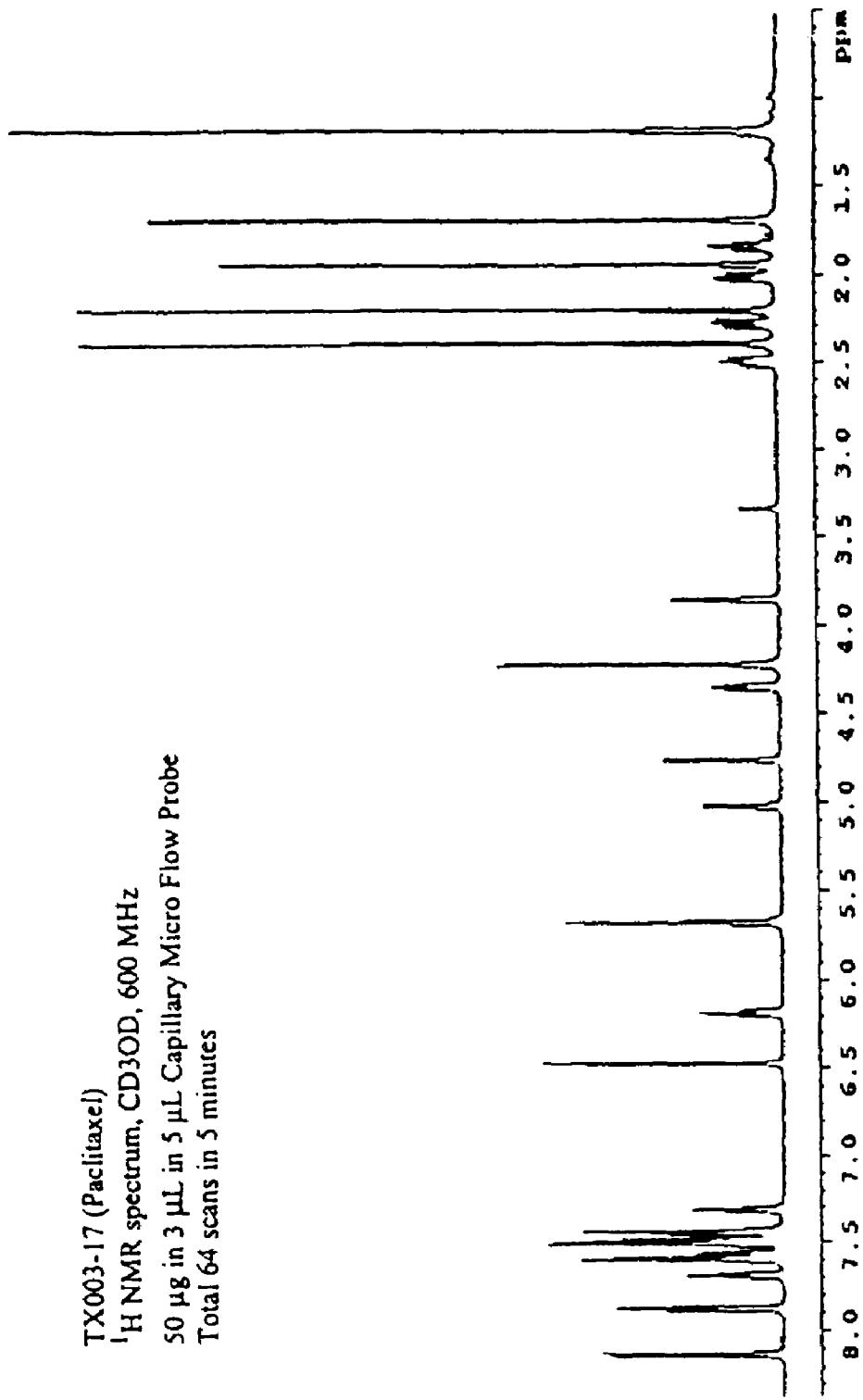
FIG. 20 is a 1H NMR spectrum of 50 μg paclitaxel in 3 μL CD3OD acquired by 5 μL microcoil flow probe on a 600 MHz NMR spectrometer.

Flash fractions (TX002 to TX005) were produced by processing 1 gram of organic extract (TX001) from *Taxus brevifolia*. As previously described, above, a *Taxus* library was produced from these flash fractions utilizing a parallel four-channel preparative HPLC system. A total of 160 preparative HPLC 14 fractions were collected. Analysis of the fractions by parallel LC-ELSD-MS showed that the fractions primarily contained 1-5 components. The quantities of the fractions in the library were from 100 µg to 1.7 mg as determined by ELSD (see FIG. 19). A total of 147 compounds from this library were detected by (+) ESI mass spectrometry. Among those samples, paclitaxel was identified in sample TX003-17 (flash fraction TX003, fraction 17) at the purity greater than 95%. All samples, including the original organic extract (TX001), flash fractions (TX002-005), and the *Taxus* library consisting of 160 preparative HPLC fractions were delivered to the NCI to be screened in vitro in the 3-cell-line anticancer panel. The results are presented in Table 3 and show that the organic extract and flash fractions TX003 and TX004 exhibited anticancer activities. Sample TX0003-17, which proved to be pure paclitaxel, exhibited activity in all three cell lines. Samples TX005-28 and 30-32 also exhibited activity on the MCF7 breast cancer cell line, in which the original TX005 did not show the activities among those cell lines (see Table 3). The NMR data needed to identify the known taxanes (1D 1H and COSY) were acquired using samples containing 5-50 µg of pure compound in 3 µL of CD3OD in the microcoil flow probe. The samples were parked in the coil after two calibration runs using strychnine as a standard. A 1H NMR spectrum of paclitaxel is shown in FIG. 20 (50 µg of sample in 3 µL of CD3OD). 1D 1H and 2D (COSY) NMR spectra as well as mass spectra allowed characterization of the major peaks from TX005-28, 30, and 31 to be 7-(β-xylosyl)-taxol, 7-(β-xylosyl)-taxol C, and 7-(β-xylosyl)-10-deacetyltaxol C, respectively.

On average 60% of the analyzed fractions contained detectable compounds with one to five compounds per fraction. A total of 36,000 fractions were made and these fractions were collectively called "the library" from which smaller, more focused libraries are drawn for screening. Screening results indicate that hit rates are 0.5% or less and the library facilitates the discovery of minor metabolites whose activity may go undetected upon the screening of crude extracts or even flash fractions. Since libraries are drawn using equal amounts from each fraction, the concentration of minor metabolites in a screening assay is comparable to that of major metabolites. Active compounds are rapidly purified from the fractions and the bioactivities of pure compounds are then confirmed. Characterization and structure determination of hit compounds has been done using the LC-ELSD-MS data and 1H and COSY NMR experiments on as little as 5 µg using a Bruker Avance 600 MHz NMR spectrometer equipped with a new 5 µL microcoil flow probe. The structures of novel compounds can be elucidated using as little as 50 µg with reasonable experiment times. Any naturally occurring active compounds can be quickly identified using the LC-ELSD-MS data and purified for structure activity relationship (SAR) studies during the screening process.

TABLE 3

Results of One Dose Primary Anticancer Assays[a]

| Samples | MCF-7 | Breast cancer | H-460 Lung cancer | SF-268 CNS cancer |
|---|---|---|---|---|
| TX001-1 | (2 µg/mL) | 31 | 91 | 75 |
| TX001-2 | (5 µg/mL) | 23 | 27 | 55 |
| TX001-3 | (10 µg/mL) | 17 | 25 | 43 |
| TX002 | (2 µg/mL) | 94 | 117 | 110 |
| TX003 | (2 µg/mL) | 19 | 23 | 29 |
| TX004 | (2 µg/mL) | 23 | 61 | 60 |
| TX005 | (2 µg/mL) | 85 | 107 | 105 |
| TX003-17 | (2 µg/mL) | 21 | 30 | 29 |
| TX005-28 | (2 µg/mL) | 21 | 71 | 49 |
| TX005-30 | (2 µg/mL) | 30 | 93 | 55 |
| TX005-31 | (2 µg/mL) | 14 | 43 | 38 |
| TX005-32 | (2 µg/mL) | 15 | 45 | 52 |
| Paclitaxel | (2 µg/mL)[b] | 23 | 13 | 30 |
| Cephalomanine | (2 µg/mL)[c] | 15 | 19 | 30 |

[a] The numbers presented in the table showed the percentage of the reduced growth of the cell lines. Samples have less than 32% are active.
[b], [c] These are the standard compounds for positive control.

What is claimed is:

1. A method of producing a chemical compound library comprising the steps of:
   (a) extracting at least one extract from at least one species of plant;
   (b) processing at least one of the at least one extract from step (a) to remove at least one type of chemical interference to produce a processed extract;
   (c) chromatographically separating the processed extract from step (b) into a plurality of chromatographic fractions, each containing an amount of chemical compounds;
   (d) determining the amount of chemical compounds in at least one of the chromatographic fractions from step (c); and
   (e) normalizing the chromatographic fractions in which the amounts were determined in step (d) to produce normalized chromatographic fractions, each such fraction comprising from about 1 microgram to about 500 micrograms of each of from one to seven chemical compounds that were present in lower concentrations in the extract and that each have a log P of from about −1 to about 5 and a molecular weight less than about 1000 Daltons;

(f) thereby to produce a chemical compound library from at least one species of plant.

2. The method of claim 1, wherein the at least one extract in step (a) is extracted from a plurality of species of plant.

3. The method of claim 2, wherein the at least one extract in step (a) is extracted from the plurality of species of plant in an extraction with an organic solvent.

4. The method of claim 2, the at least one extract in step (a) is extracted from the plurality of species of plant in a multiple step extraction comprising a first extraction step carried out with a first organic solvent and thereafter a second extraction step whereby insoluble material is extracted by use of a mixture of a second organic solvent, which may or may not be the same as the first organic solvent, and water.

5. The method of claim 4, wherein the first organic solvent is about 50% by weight ethanol and about 50% weight ethyl acetate and wherein the mixture of the second organic solvent and water is about 70% by weight methanol and about 30% by weight water.

6. The method of claim 1, wherein in step (b), the at least one of the at least one extract from step (a) is processed to remove a tetramer or greater of a polyphenolic compound.

7. The method of claim 1, wherein in step (b), the at least one of the at least one extract from step (a) is processed to remove a compound with a molecular weight of greater than 1000 daltons.

8. The method of claim 1, wherein the at least one extract is processed in step (b) by flash chromatography to remove the at least one type of chemical interference.

9. The method of claim 1, wherein the at least one extract is processed in step (b) by use of a size exclusion filter to remove the at least one type of chemical interference.

10. The method of claim 1, wherein the at least one extract is processed in step (b) by use of a polyamide column to remove the at least one type of chemical interference.

11. The method of claim 1, wherein in step (b), the at least one of the at least one extract from step (a) is processed to remove a compound with a with a log P of greater than about 5 or less than −1.

12. The method of claim 1, further comprising the step of providing pre-determined analytical data comprising molecular ions and chromatographic elution conditions for the at least one chromatographic fraction.

13. The method of claim 1, further comprising the step of providing NMR spectra for the at least one chromatographic fraction.

14. The method of claim 1, further comprising the step of providing MS/MS fragmentation patterns for the at least one chromatographic fraction.

15. The method of claim 1, further comprising the step of providing LC-ELSD-MS data sufficient to identify the amounts of each of said chemical compounds for the at least one chromatographic fraction.

16. The method of claim 1, wherein said chromatographic fractions are produced by eluting one to five chemical compounds with related physical properties from a reverse phase chromatography column with a flow rate of more than 0.48 and less than 0.80 column volumes per minute of a solvent system and where an acetonitrile concentration in the solvent system increases by more than 0.008% per second and less than 0.035% per second.

17. The method of claim 1, wherein each of the normalized chromatographic fractions of step (e) has associated therewith a retention time, molecular weight, mass and number of compounds which are recorded in a database.

18. The method of claim 1, further comprising the step of preparing a sublibrary of chemical compounds in the library in which the chemical compounds in the sublibrary have similar predetermined molecular ions.

19. The method of claim 1, further comprising the step of preparing a sublibrary of chemical compounds in the library in which the chemical compounds in the sublibrary have similar predetermined log Ps.

20. The method of claim 1, wherein step (c) of said method is carried out with a reverse phase chromatography column having a flow rate of more than 0.48 and less than 0.80 column volumes per minute of a solvent system, wherein an acetonitrile concentration in said solvent system increases at more than 0.008% per second and less than 0.035% per second; and wherein at least fifteen chromatographic fractions are collected.

21. The method of claim 1 wherein the chemical compound library comprises at least about 100 compounds from one plant species and containing at least one triterpene compound, one lignan compound, one flavonoid compound and one alkaloid compound.

22. The method of claim 1 wherein the chemical compound library comprises at or more isomeric forms of a chemical compound.

* * * * *

UNITED STATES PATENT AND TRADEMARK OFFICE
CERTIFICATE OF CORRECTION

PATENT NO. : 7,367,933 B2 Page 1 of 1
APPLICATION NO. : 11/358815
DATED : May 6, 2008
INVENTOR(S) : Eldridge et al.

It is certified that error appears in the above-identified patent and that said Letters Patent is hereby corrected as shown below:

Claim 4 Col. 51 Line 15-22, should read
    4. The method of claim 2, [[the]] wherein at least one extract in step (a) is extracted from the plurality of species of plant in a multiple step extraction comprising a first extraction step carried out with a first organic solvent and thereafter a second extraction step whereby insoluble material is extracted by use of a mixture of a second organic solvent, which may or may not be the same as the first organic solvent, and water.

Claim 22 Col. 52 Line 47-49, should read
    22. The method of claim 1 wherein the chemical compound library comprises [[at]] two or more isomeric forms of a chemical compound.

Signed and Sealed this

Twenty-second Day of July, 2008

JON W. DUDAS
*Director of the United States Patent and Trademark Office*